United States Patent [19]
Wank

[11] Patent Number: 5,319,073
[45] Date of Patent: Jun. 7, 1994

[54] METHOD OF PURIFYING CHOLECYSTOKININ RECEPTOR PROTEIN

[75] Inventor: Stephen A. Wank, Bethesda, Md.

[73] Assignee: The United States of America, as represented by the Department of Health & Human Services, Washington, D.C.

[21] Appl. No.: 937,609

[22] Filed: Sep. 2, 1992

Related U.S. Application Data

[63] Continuation-in-part of Ser. No. 928,033, Aug. 11, 1992, and a continuation-in-part of Ser. No. 861,769, Apr. 1, 1992, abandoned, which is a continuation-in-part of Ser. No. 831,248, Feb. 7, 1992, abandoned.

[51] Int. Cl.$^5$ ............................................. C07K 3/02
[52] U.S. Cl. ................................... 530/412; 530/350; 435/69.1
[58] Field of Search ............... 530/412, 350; 435/69.1; 536/23.5

[56] References Cited

FOREIGN PATENT DOCUMENTS

WO92/20814 11/1992 PCT Int'l Appl. ............ C12Q 1/00

OTHER PUBLICATIONS

Meth. in Ehly, 104: 97–113 (1984) Lowe et al., Affinity Chromatography on Immobilized Dyes.

A. A. Dufresne, et al., "Purification of A-subtype pancreatic cholecystokin receptor by immunoaffinity chromatography", *Biochimie* (1992) 74, 149–151.

A. B. Wank, et al., "Brain and gastrointestinal cholecystokinin receptor family: Structure and functional expression", *Proc. Natl. Acad. Sci., U.S.A.*, vol. 89, pp. 8691–8695, Sep. 1992.

A. C. Pisegna, et al., "Molecular Cloning of the Human Brain and Gastric Cholecystokinin Receptor: Structure, Functional Expression and Chromosomal Localization", *Biochemical and Biophysical Research Communications*, vol. 189, No. 1, Nov. 30, 1992, pp. 296–303.

Kopin et al., "Expression cloning anc characterization of the canine parietal cell gastrin receptor", PNAS USA 89:3605 (1992).

Duong et al., "Purification and Characterization of the Rat Pancreatic Cholecystokinin Receptor", J. Biol. Chem. 264(30): 17990 (1989).

Szecowka et al., "Purification of the pancreatic cholecystokinin receptor", Regulatory Peptides 24:215 (1989).

Knapp et al., "A New, Highly Selective CCK-B Receptor Radioligand ([$^3$H][N-methyl-Nle$^{28,31}$]CCK-$_{26-33}$):Evidence for CCK-B Receptor Heterogeneity", J. Pharm. Exp. Ther. 255(3): 1278 (1990).

Grider et al., "Distinct receptors for cholecystokinin and gastrin on muscle cells of stomach and gallbladder", Gastrointest. Liver Physiol. 22: G184 (1990).

Roche et al.l, "Characterization of a gastrin-type receptor on rabbit gastric parietal cells using L365, 260 an L364, 718", Gastrointest. Liver Physiol. 23: G182 (1991).

Wank et al., "Purification, molecular cloning, and functional expression of the cholecystokinin receptor from rat pancreas", PNAS USA 89: 3125 (Apr., 1992).

Roche et al., "Gastrin and CCK" Receptors on Histamine-and Somatostatin-Containing Cells from Rabbit Fundic Mucosa-II, Biochem. Pharmacol. 42(4): 771 (1991).

Chemer et al., "Functionally distinct receptors for cholecystokinin and gastrin on dispersed chief cells from guinea pig stomach", Gastrointest. Liver Physiol. 17: G151 (1988).

*Primary Examiner*—Robert J. Hill, Jr.
*Assistant Examiner*—John D. Ulm
*Attorney, Agent, or Firm*—Foley & Lardner

[57] ABSTRACT

An unconventional approach to purifying CCK receptor protein to sequenceable-grade homogeneity has been discovered. By this approach, CCK receptor protein can be obtained and sequenced routinely from a variety sources, and from the sequence information thus obtained it is possible to prepare oligonucleotides suitable for cloning CCK receptor genes. "CCK receptor" in this context denotes any from a group of proteins that displays a characteristic CCK binding affinity and that is encoded by a nucleotide sequence which hybridizes a oligonucleotide probe designed in accordance with the criteria elaborated herein.

3 Claims, 36 Drawing Sheets

FIG. IA

```
CCGCAATGCT TGCCCAGATG CTCTGAGAAT GGCGAACTCA AGTTGCCTTT AGGAATGGCT            60

GCAAAGCCCA CACCTGGAAA TCTCCCCCTC CCTGCTCCTC CACGGCAGT TGCATTTGGG           120

AGACCCTGTG ATCATTAGAG GAGAGAGACA GGA ATG AGC CAT TCA CCA GCT CGC           174
                                  Met Ser His Ser Pro Ala Arg
                                   1                       5

CAG CAC TTG GTA GAA AGC AGC AGG ATG GAC GTG GTC GAC AGC CTT CTT            222
Gln His Leu Val Glu Ser Ser Arg Met Asp Val Val Asp Ser Leu Leu
            10                      15                      20

ATG AAT GGG AGC AAC ATC ACT CCC CCC TGT GAA CTC GGA CTG GAA AAT            270
Met Asn Gly Ser Asn Ile Thr Pro Pro Cys Glu Leu Gly Leu Glu Asn
            25                      30                      35

GAG ACG CTT TTC TGC TTG GAT CAA CCT CAA CCT TCA AAA GAG TGG CAG            318
Glu Thr Leu Phe Cys Leu Asp Gln Pro Gln Pro Ser Lys Glu Trp Gln
40                      45                      50                  55
```

FIG. 1B

```
     TCT GCA CTG CAG ATT CTC CTG TAC TCC ATC ATA TTC CTT CTC AGT GTG    366
     Ser Ala Leu Gln Ile Leu Leu Tyr Ser Ile Ile Phe Leu Leu Ser Val
                          60                  65                  70

CTG GGG AAC ACG CTG GTT ATA ACG GTG CTG ATT CGA AAC AAG AGG ATG    414
     Leu Gly Asn Thr Leu Val Ile Thr Val Leu Ile Arg Asn Lys Arg Met
                  75                  80                  85

CGG ACG GTC ACC AAC ATC TTC CTG CTG TCC CTG GCT GTC AGT GAC CTC    462
     Arg Thr Val Thr Asn Ile Phe Leu Leu Ser Leu Ala Val Ser Asp Leu
              90                  95                 100

ATG CTC TGC CTC TTC TGC ATG CCG CCC TTC AAC CTC ATC CCC AAC CTG CTC    510
     Met Leu Cys Leu Phe Cys Met Pro Phe Asn Leu Ile Pro Asn Leu Leu
             105                 110                 115

AAG GAT TTC ATC TTC GGA AGT GCC GTG TGC AAG ACT ACC ACC TAC TTC    558
     Lys Asp Phe Ile Phe Gly Ser Ala Val Cys Lys Thr Thr Thr Tyr Phe
         120                 125                 130                 135

ATG GGC ACT TCC GTG AGC GTT TCC ACC TTC AAC CTG GTA GCC ATC TCT    606
     Met Gly Thr Ser Val Ser Val Ser Thr Phe Asn Leu Val Ala Ile Ser
         140                 145                 150
```

FIG. IC

```
CTG GAG AGA TAT GGC GCC ATC TGC AGA CCC CTA CAG TCC CGC GTC TGG          654
Leu Glu Arg Tyr Gly Ala Ile Cys Arg Pro Leu Gln Ser Arg Val Trp
            155                 160                 165
                                    ┌──────IV
CAA ACA AAG TCC CAT GCT TTG AAG GTC ATC GCT GCC ACC TGG TGC CTC          702
Gln Thr Lys Ser His Ala Leu Lys Val Ile Ala Ala Thr Trp Cys Leu
            170                 175                 180

TCC TTT ACC ATC ATG ACT CCG TAC CCC ATT TAC AGC AAC TTG GTG CCT          750
Ser Phe Thr Ile Met Thr Pro Tyr Pro Ile Tyr Ser Asn Leu Val Pro
            185                 190                 195

TTT ACT AAA AAT AAC CAG ACG GCG AAC ATG TGC CGC TTC CTG TTG              798
Phe Thr Lys Asn Asn Gln Thr Ala Asn Met Cys Arg Phe Leu Leu
200                 205                 210                 215
                     ▲                                  ┌─────V
CCA AGT GAC GCT ATG CAG CAG TCC TGG CAA ACA TTC CTA CTC ATC              846
Pro Ser Asp Ala Met Gln Gln Ser Trp Gln Thr Phe Leu Leu Ile
            220                 225                 230
```

FIG. ID

| | | | | | | | | | | | | | | | | |
|---|---|---|---|---|---|---|---|---|---|---|---|---|---|---|---|---|
| CTC | TTT | CTC | CCT | GGG | ATT | GTG | ATG | GTG | GTG | GCC | TAC | GGG | TTG | ATC | | 894 |
| Leu | Phe | Leu | Pro | Gly | Ile | Val | Met | Val | Val | Ala | Tyr | Gly | Leu | Ile | | |
| 235 | | | | | | | 240 | | | | | | | 245 | | |
| TCT | CTG | GAA | CTC | TAC | CAA | GGA | ATC | ATC | GAT | GCC | AGC | CAG | AAG | AAA | | 942 |
| Ser | Leu | Glu | Leu | Tyr | Gln | Gly | Ile | Ile | Asp | Ala | Ser | Gln | Lys | Lys | | |
| Ser | Leu | Glu | Leu | Tyr | Gln | Gly | Ile | Phe | Asp | Ala | Ser | Gln | Lys | Lys | | |
| 250 | | | | | 255 | | | | | 260 | | | | | | |
| TCT | GCC | AAA | GAG | AAG | AAG | CCG | AGC | ACT | GGC | AGC | AGC | ACC | CGA | TAT | GAG | 990 |
| Ser | Ala | Lys | Glu | Lys | Lys | Pro | Ser | Thr | Gly | Ser | Ser | Thr | Arg | Tyr | Glu | |
| 265 | | | | | 270 | | | | 275 | | | | | | | |
| GAT | AGT | GAT | GGC | TGT | TAC | TTG | CAG | AAG | TCC | CGG | CCC | AGG | AAG | CTG | | 1038 |
| Asp | Ser | Asp | Gly | Cys | Tyr | Leu | Gln | Lys | Ser | Arg | Pro | Arg | Lys | Leu | | |
| 280 | | | | | 285 | | | | 290 | | | | | 295 | | |
| GAG | CTT | CAG | CAG | CTG | TCT | AGC | GGT | GGC | AGC | AGA | CTC | AAC | CGG | | | 1086 |
| Glu | Leu | Gln | Gln | Leu | Ser | Ser | Gly | Gly | Ser | Arg | Leu | Asn | Arg | | | |
| | | | | 300 | | | | 305 | | | | | 310 | | | |
| ATC | AGG | AGC | AGT | TCA | GCT | GCC | AAC | CTG | ATA | GCC | AAG | AAG | CGC | GTG | | 1134 |
| Ile | Arg | Ser | Ser | Ser | Ala | Ala | Asn | Leu | Ile | Ala | Lys | Lys | Arg | Val | | |
| | | 315 | | | | | 320 | | | | | 325 | | | | |
| ATC | CGC | ATG | CTC | ATT | GTC | ATC | GTG | CTC | TTC | TTC | CTG | TGC | TGG | ATG | | 1182 |
| Ile | Arg | Met | Leu | Ile | Val | Ile | Val | Leu | Phe | Phe | Leu | Cys | Trp | Met | | |
| 330 | | | | | 335 | | | | | 340 | | | | | | |

FIG. 1E

```
CCC ATC TTC AGC GCC AAC GCC TGG CGG GCA TAT GAC ACG GTT TCT GCC    1230
Pro Ile Phe Ser Ala Asn Ala Trp Arg Ala Tyr Asp Thr Val Ser Ala
345                     350                 355

GAG AAG CAC CTC TCA GGG ACT CCC ATC TCC TTC ATC CTC CTC TCC        1278
Glu Lys His Leu Ser Gly Thr Pro Ile Ser Phe Ile Leu Leu Ser
360                 365                 370             375
                                         VII

TAC ACC TCC TGT GTT AAC CCC ATC TAT TGC TTC ATG AAC AAA            1326
Tyr Thr Ser Cys Val Asn Pro Ile Tyr Cys Phe Met Asn Lys
380                 385                 390

CGC TTT CGC CTG GGC TTC ATG GCC ACC TTC CCT TGT TGC CCG AAT CCC    1374
Arg Phe Arg Leu Gly Phe Met Ala Thr Phe Pro Cys Cys Pro Asn Pro
395                 400                 405

GGT CCC CCA GGG GTG AGA GGA GAG GTG GGA GAG GAG GAT GGG AGG        1422
Gly Pro Pro Gly Val Arg Gly Glu Val Gly Glu Glu Asp Gly Arg
410                 415                 420

ACC ATA AGG GCA TTG CTG TCC AGG TAT TCC TAC AGC CAC ATG AGC ACC    1470
Thr Ile Arg Ala Leu Leu Ser Arg Tyr Ser Tyr Ser His Met Ser Thr
425                 430                 435

TCT GCT CCA CCC CCC TGAACTCCAC CTGGTCCACT G                        1506
Ser Ala Pro Pro Pro End
440             445
```

FIG. 2A

```
TGACCCTGCT TGCTCAACTC TACGTCTTGT TTCGTTTCT GTTCTGCGCC GTTACAGATC      60
CAAGCTCCTC GAGCCCGGGC TGCAGGAATT CTGCGGCCGC CGCTTAGCAG AGCTAAGTGG    120
GACTTCACTG GAGCC ATG GAG CTG CTC AAG CTG AAC CGC AGC GTG CAG GGA    171
              Met Glu Leu Leu Lys Leu Asn Arg Ser Val Gln Gly
               1                  5                         10

CCA GGA CCC GGG TCG GGG TCT TCT TTG TGC CGC CCG GGT GTC TCC CTT      219
Pro Gly Pro Gly Ser Gly Ser Ser Leu Cys Arg Pro Gly Val Ser Leu
           15                       20                      25

CTC AAC AGT AGT AGT GCC GGG AAC CTC AGC TGT GAC CCC CCT CGT ATC      267
Leu Asn Ser Ser Ser Ala Gly Asn Leu Ser Cys Asp Pro Pro Arg Ile
       30                       35                      40

CGC GGA ACC GGG ACC AGA GAA TTG GAG ATG GCG ATT AGA ATC ACC CTT      315
Arg Gly Thr Gly Thr Arg Glu Leu Glu Met Ala Ile Arg Ile Thr Leu
 45                      50                      55             60

TAT GCA GTG ATC TTT CTG ATG AGT GTT GGC GGA AAC GTG CTC ATC ATC      363
Tyr Ala Val Ile Phe Leu Met Ser Val Gly Gly Asn Val Leu Ile Ile
           65                       70                      75

GTG GTC CTG GGA CTG AGC CGA CGC CTA AGA ACG GTC ACC AAC GCC TTC      411
Val Val Leu Gly Leu Ser Arg Arg Leu Arg Thr Val Thr Asn Ala Phe
       80                       85                      90
```

FIG. 2B

```
                                                                                        459
CTG CTC TCC CTG GCA GTC AGC GAC CTC CTG GCC GTG GCT TGC ATG
Leu Leu Ser Leu Ala Val Ser Asp Leu Leu Ala Val Ala Cys Met
         95                      100                     105
                              ⊢——II——
                                                                                        507
CCC TTC ACA CTC CTG CCC AAC CTC ATG GGC ACA TTC ATC TTC GGC ACA
Pro Phe Thr Leu Leu Pro Asn Leu Met Gly Thr Phe Ile Phe Gly Thr
         110                     115                     120
                                                                                        555
GTC ATC TGC AAG GCC ATT TCC TAC CTC ATG GGG GTA TCA GTG AGT GTA
Val Ile Cys Lys Ala Ile Ser Tyr Leu Met Gly Val Ser Val Ser Val
         125 ●                   130                     135                     140
                                                      ⊢——III——
                                                                                        603
TCC ACT CTA AAT CTC GTG GCC ATA GCC CTG GAG CGA TAC AGC GCC ATC
Ser Thr Leu Asn Leu Val Ala Ile Ala Leu Glu Arg Tyr Ser Ala Ile
         145                     150                     155
                                                                                        651
TGC CGA CCA CTG CAA GCA CGA TGG CTG TGG CTG CTG TCC CAC GCA GCT
Cys Arg Pro Leu Gln Ala Arg Trp Gln Thr Arg Ser His Ala Ala
         160                     165                     170
            ⊢——IV——
                                                                                        699
CGG GTG ATC TTA GCC ACG TGG CTG CTG TCT GGA CTG CTT ATG GTA CCC
Arg Val Ile Leu Ala Thr Trp Leu Leu Ser Gly Leu Leu Met Val Pro
         175                     180                     185
```

FIG. 2C

```
TAC CCT GTG TAC ACC ATG GTA CAG CCA GTG GGA CCT CGA GTG CTG CAG    747
Tyr Pro Val Tyr Thr Met Val Gln Pro Val Gly Pro Arg Val Leu Gln
        190                 195                 200

TGC ATG CAT CGC TGG CCC AGT GCA CGT GTC CAA CAA ACC TGG TCC GTG    795
Cys Met His Arg Trp Pro Ser Ala Arg Val Gln Gln Thr Trp Ser Val
205●        210                 215                         220

CTA CTG CTG CTT TTG TTC ATC CCG GGT GTG GTT ATT GCG GTG            843
Leu Leu Leu Leu Leu Phe Ile Pro Gly Val Val Ile Ala Val
            225                 230                 235

GCC TAT GGA CTC CGC GAA CTC TAC CTA GAG CTC CAC TTT GAT            891
Ala Tyr Gly Leu Arg Glu Leu Tyr Leu Gly Leu His Phe Asp
        240                 245                 250

GGT GAA AAT GAC AGC GAG ACC CAA AGC CGG GCC CGA AAC CAA GGG GGC    939
Gly Glu Asn Asp Ser Glu Thr Gln Ser Arg Ala Arg Asn Gln Gly Gly
        255▲                260                 265

CTG CCG GGT GGG GCA GCA CCA GGG CCT GTC CAC CAG AAC GGG GGC TGC    987
Leu Pro Gly Gly Ala Ala Pro Gly Pro Val His Gln Asn Gly Gly Cys
        270                 275                 280
```

FIG. 2D

```
CGG CCT GTA ACC AGC GTA GCT GGG GAA GAC AGT GAT GGC TGT GTG         1035
Arg Pro Val Thr Ser Val Ala Gly Glu Asp Ser Asp Gly Cys Val
285                 290                 295                 300

CAA CTT CCG CGT TCC CGA CTG GAG ATG ACA CTA ACC ACA CCC ACT         1083
Gln Leu Pro Arg Ser Arg Leu Glu Met Thr Leu Thr Thr Pro Thr
        305                 310                 315

CCT GGG CCA GTC CCT GGC CCT CGG CCC AAC CAG GCC AAG CTG GCT         1131
Pro Gly Pro Val Pro Gly Pro Arg Pro Asn Gln Ala Lys Leu Ala
            320                 325                 330
                                                    ├──VI
AAG CGG GTG GTG CGA ATG CTG CTA GTG ATT GTT TTG CTT TTC TTC         1179
Lys Arg Val Val Arg Met Leu Leu Val Ile Val Leu Leu Phe Phe
        335                 340                 345

CTG TGT TGG CTG CCA GTG TAC AGC GTC AAC ACG TGG CGC GCC TTC GAT     1227
Leu Cys Trp Leu Pro Val Tyr Ser Val Asn Thr Trp Arg Ala Phe Asp
350                 355                 360
```

FIG. 2E

```
GGC CCA GGC GCA CAA CGA GCA CTC TCA GGG GCC CCT ATC TCT TTC ATC    1275
Gly Pro Gly Ala Gln Arg Ala Leu Ser Gly Ala Pro Ile Ser Phe Ile
365                 370                 375                 380
                                    |——————VII——————————————————
CAC TTG CTG AGC TAC GTC TCT GCT TGT GTC AAC CCC CTG GTC TAC TGT    1323
His Leu Leu Ser Tyr Val Ser Ala Cys Val Asn Pro Leu Val Tyr Cys
            385                 390                 395

TTC ATG CAC CGC TTC CGC CAG GCC TGC CTG GAC ACA TGT GCC CGC        1371
Phe Met His Arg Arg Phe Arg Gln Ala Cys Leu Asp Thr Cys Ala Arg
        400                 405                 410

TGT TGC CCA CGC CCT CCA CGA GCT CGC CCA CAG CCT CTT CCA GAT GAG    1419
Cys Cys Pro Arg Pro Pro Arg Ala Arg Pro Gln Pro Leu Pro Asp Glu
•       415                 420                 425

GAT CCT ACC CCC TCC ATC GCT TCG CTG TCC AGG CTA AGC TAT ACC        1467
Asp Pro Thr Pro Ser Ile Ala Ser Leu Ser Arg Leu Ser Tyr Thr
    430                 435                 440

ACC ATC AGC ACA CTG GGG CCT GGC TGAGGGGGTG GGAGATTGGA GAAAGAGACA   1521
Thr Ile Ser Thr Leu Gly Pro Gly End
445                 450
```

FIG. 2F

```
AGATACATAA TTACTATCAA ATGACCCATC CAAACACATA AGAAACAAAA TTCAGAATTA  1581
ATCAGGTGAA CACCCAACAC CATGGACAGA CCCCTACACA CAGAAAATAG TATCTTTGCT  1641
GCCCTACCTG AAACAGATAG GAGTCTCATA GGAAAGGAGG CTCACTTCTG ATAAGGGGCT  1701
GAGTCCCTTC CTAGACATCT TGCACTGACC CCATTACATG GACAGACACA AGGTCCGTAG  1761
CAGTAAACTT TACCTATAAA GGGGAACTCT GACAAGGGCT GATTGGCTCC TCATATGAAC  1821
ATATTACTGA CACTATTCTG TAGTGCCCAT AGCCTAGTGC AGAAGTGACT TAGGACATTG  1881
TGGCTGTTCC CGTTTGACTT CATTATTGCC TTCCTCATCC AGCACTGAAA TTATCAACCA  1941
CACGCCTTTC ACCTTTCGGA GCTGCCGATC GTTCAGCACT GAAAAGTCCC CCCCCCCAC   2001
TCCTTTCCAT TGGAGACTGT GGAAAGTCCT CTTCCCTCCT GCCTCTCCTC CCTCACCAGA  2061
CCACATCATA AAAGGATAAG TGACTTAGTG TCCTCCTGGA CTTCTTGAGG TAGGTGAACA  2121
GGTGTGGTTT ATGGGAAGCT TCTTCATTTA TGGCTCCCA  TGACTAATCT ACCCCATATC  2181
CAACCTTGTG CAAAAAGGCC AGGGTATGAA GATAGGGATG AGCGTACCCT CTCTTGGTTG  2241
TC                                                                2243
```

FIG. 3A

```
RCCKBR  ............MELLKLNRSVQGPGPGSGSSECRPGVSELNSS...SAGNESCDPPRE....RGTGTRELEMAIRITEYAVIFLMGVGGNMLVIVGLS         82
RCCKAR  ............MSHSPARQHLVESSRMDVVDSLLMNGSNITPPCELGLENETLFCLDQPQPSKEWQSALQILEYSIEFELSVLGNTLVITVEIRN         84
MGRPR   ............MAPNMCSHLNLDVDPFES...CNDTFNQSLSPPKMDMVFHPGFEY..............VIPAVVGLEIVIGLIGNTLVIKIFCTV        69
RNMBR   ............MPPRSLPNLSLPTEASESELEPEWNENDFLPDSGTTAELVIRC...............VIPSEYLIEISVGLLGNMLVKIFLTN          71
RSKR    ....................................MGTRAIVSDANILSGLESNATGVTAFSMPGNQLALMATAYAVLALVEVAVTGNATVIMIILAH        61
RSPR    ....................................MDNVLPMDSDEFPNISTNTSESNQFVQPTWQIVLNAAAYTVIVVTSVVGNVVVIMIILAH         60
RNMKR   MASVPRGEMTDGTVEVGTHTGNLSSALGVTEWLALQAGNFSSALGLPATTQAPSQVRANLTNQFVQPSWRIALWSLAYGLVAVAVFGNLIVIWIILAH        100

RCCKBR  RRLRTVTNAFEESSLAVSDLLLAVACMPFTELPNLMGTFIFGTVICKAISYLMGVSVSVSTLNLVAIALEERYSAICRPLQARVMQTRSHAARVILATMELS       182
RCCKAR  KRMRTVTNIFLLSSLAVSDLMLCLFCMFNLIPNLLKDFIFGSAVGKTTTYFPKGTSVSVSTFNLVAISLERYGAICRPLQSRVWQTKSHALKVIAATMCLS       184
MGRPR   KSWRNVPNLFISSLALGDLLLLVTCAPVDASKYLADRWLFGRIGCKLIPFIQLTSVGVSVFTLTALSADRYKAIVRPMDIQASHALMKICLKAALIWIVS       169
RNMBR   STMRSVPNIFEISNEAAGDLELLLTCVPVDASRYFFDEMWPFGKLGCKLIPAIQLTSVGVSVFTLTALSADRYRAIVNPMDMQTSGVVLWTSLKAVGIWVVS      171
RSKR    ERMRTVTNYFIINLALADLQMVMFCMFGRAFCYIYAHSNIMYFGRAFCYFQNLFPITAMFVSIYSMTAIAADRYMAIVHPFQPRLSAPSTKA..IIAGIMEVA     159
RSPR    KRMRTVTNYFLVNLAFAEAQMAAFNTVVNFTYAVHNVMYYGLFYCKFHNFPPIAALFASIYSMTAVAFDRYMAIIHPIQPRLSATATKV..VIFVIWVLA       158
RNMKR   KRMRTVTNYFLVNLAFSDASVAAFNTLINFIYGEHSEMYFGANYCRFQMFFPITAVFASIYSMTAIAVDRYMAIIDPLKPRLSATATKI..VIGSIMTIA       198

RCCKBR  GLHFDGENDSETQSRARNQGGLPGGAA.................SVEEEELEEFFIPGVVIAVAYGLISRELYL.GLHFDGENDSETQSRARNQGGLPGGAA        274
RCCKAR  FIEHTPYPYIYSNLVPFTKNNMNQTANMKCRFLLPSDAMQQ.SW..QTFLLILELLLFFLLLPGIVMVAYGLISLELYQ.GIKFDASQKKSAKEKKPSTGS....    274
MGRPR   MLELAIPEAVFSDLHPFHVKDTNQTFISCAPYHSNELH.PKIHSWASFLVFYVIPLAIISVMYYFIARNLIQSAYNLPVEGNIHVKK............         255
RNMBR   VLLAVPEAVFSEVARIGSSD.NSSFTACIPYPQTDELH.PKIHSVFIFVFLIPLFLVISIYYHIAKTLIRSAHNLPGEYNEHTKK............           256
RSKR    LALASPQCFYSTI.....TVDEGATKCVVAHPNDNGGKQMILLYHLVVFYLIPLVLMFGAYSVIGLTEMKRAVPRHQAHGA............              237
RSPR    LLEAFPQGYYSTT......ETMESRVVGMIEWPEHPNRTYEKAYHICVTVLIYFLPLLVIGYAYIVVGITLWASEIP.GDSSDR............           235
RNMKR   KVMPGRTLCYVQWPEGPKQHF..TYHIIVIILEYCFPLLLIMGVTYTIVGITLWGGEIP.GDTCDK............                             273
```

```
CGCAGGATGC GTGCCCAGCT GGACGGAGGG TAGTGAACTC CAGGTGCCTT TAGGAATGGC         60
TGCAAAAGCC CACACCTGGC AATCACTCTC TGCCTGCCTC TCCCCGGCAG GTTGCATTTG        120
GGAGGCGCTC TGGTCATCAG AGGAATGAGC GTGGAGAGAG CTGTTTGCCA GCCCGCCAGC        180
CCCTGGGTGG AAGCAGAGGC GAGG ATG GAC GTG GTA GAC AGC CTT TTT GTG          231
                            Met Asp Val Val Asp Ser Leu Phe Val
                             1                   5

AAT GGG AGC AAC ATC ACT TCT GCC TGC GAG CTC GGC TTT GAA AAT GAG          279
Asn Gly Ser Asn Ile Thr Ser Ala Cys Glu Leu Gly Phe Glu Asn Glu
 10    ▲           15                        20                25   ▲

ACA CTT TTC TGC TTG GAT CGG CCC CGG CCT TCC AAA GAG TGG CAG CCG          327
Thr Leu Phe Cys Leu Asp Arg Pro Arg Pro Ser Lys Glu Trp Gln Pro
                30                        35                   40

GCG GTG CAG ATT CTC TTG TAT TCC TTG ATA TTC CTG CTC AGC GTG CTG          375
Ala Val Gln Ile Leu Leu Tyr Ser Leu Ile Phe Leu Leu Ser Val Leu
          45                        50                   55
```

FIG. 6B

```
GGA AAC ACG CTG GTA ATC ACG GTG CTG ATT CGG AAC AAG AGG ATG AGG
Gly Asn Thr Leu Val Ile Thr Val Leu Ile Arg Asn Lys Arg Met Arg
        60                  65                  70
                                                    ├──II──
ACG GTC ACT AAC ATC TTC CTG CTC TCA CTG GCT GTC AGT GAC CTC ATG    423
Thr Val Thr Asn Ile Phe Leu Leu Ser Leu Ala Val Ser Asp Leu Met
        75                  80                  85

CTC TGC CTC TTC TGC ATG CCC TTC AAC CTC ATC CCC AGC CTG AAG        471
Leu Cys Leu Phe Cys Met Pro Phe Asn Leu Ile Pro Ser Leu Lys
    90                  95                  100                 105

GAT TTC ATC TTC GGG AGT GCC GTG TGC AAG ACC ACC TAC TTC ATG        519
Asp Phe Ile Phe Gly Ser Ala Val Cys Lys Thr Thr Tyr Phe Met
        110                 115                 120
     ──III──┤
GGC ACC TCT GTG AGT GTA TCC ACC TTT AAT CTG GTG GCC ATA TCG CTG    567
Gly Thr Ser Val Ser Val Ser Thr Phe Asn Leu Val Ala Ile Ser Leu
        125                 130                 135

GAG AGA TAC GGA GCA ATT TGC AAA CCC TTA CAG TCC CGC GTC TGG CAA    615
Glu Arg Tyr Gly Ala Ile Cys Lys Pro Leu Gln Ser Arg Val Trp Gln
        140                 145                 150
                                                                   663
```

FIG. 6C

```
ACA AAG TCG CAT GCT TTG AAG GTG ATT GCT GCT ACC TGG TGC CTC TCC   711
Thr Lys Ser His Ala Leu Lys Val Ile Ala Ala Thr Trp Cys Leu Ser
155                 160                 165
                                    |—————— IV ——————

TTT ACC ATC ATG ACC CCC TAC CCC ATC TAC AGC AAC CTG GTG CCT TTT   759
Phe Thr Ile Met Thr Pro Tyr Pro Ile Tyr Ser Asn Leu Val Pro Phe
170                 175                 180                 185

ACC AAA AAT AAC CAG ACC GGG AAC ATG TGC CGC TTC CTA CTG CCA       807
Thr Lys Asn Asn Gln Thr Gly Asn Met Cys Arg Phe Leu Leu Pro
            190                 195                 200

AAC GAT GTT ATG CAG CAG ACC TGG CAC ACT TTC CTG TTA CTC ATC CTC   855
Asn Asp Val Met Gln Gln Thr Trp His Thr Phe Leu Leu Leu Ile Leu
            205                 210                 215
                                            |—————— V ——————

TTT CTT ATT CCC GGA ATT GTG ATG ATG GTG GCA TAT GGA CTG ATT TCT   903
Phe Leu Ile Pro Gly Ile Val Met Met Val Ala Tyr Gly Leu Ile Ser
            220                 225                 230
```

FIG. 6D

```
CTG GAA CTT TAC CAA GGA ATA AAA TTC GAT GCT ATC CAG AAG AAA TCT          951
Leu Glu Leu Tyr Gln Gly Ile Lys Phe Asp Ala Ile Gln Lys Lys Ser
235                     240                 245

GCT AAA GAA AGG AAG ACA AGC ACT GGC AGC AGT GGC CCG ATG GAG GAC          999
Ala Lys Glu Arg Lys Thr Ser Thr Gly Ser Ser Gly Pro Met Glu Asp
250                 255                 260                 265

AGT GAT GGG TGT TAC TGT CTG CAG AAG TCC AGG CAC CCC AGA AAG CTG GAG     1047
Ser Asp Gly Cys Tyr Cys Leu Gln Lys Ser Arg His Pro Arg Lys Leu Glu
        270                 275                 280

CTT CGG CAG CTG TCC CCC AGC AGT GGC AGC AAC AGG ATC AAT CGT             1095
Leu Arg Gln Leu Ser Pro Ser Ser Gly Ser Asn Arg Ile Asn Arg
285                 290                 295
```

FIG. 6E

```
ATC CGG AGC AGC TCC ACC GCC AAC TTG ATG GCC AAA AAG CGG GTG     1143
Ile Arg Ser Ser Ser Thr Ala Asn Leu Met Ala Lys Lys Arg Val
        300                 305                 310
                                    ├──────VI──────
ATC CGC ATG CTC ATC GTC ATT GTG GTC CTC TTC TTC CTG TGC TGG ATG 1191
Ile Arg Met Leu Ile Val Ile Val Val Leu Phe Phe Leu Cys Trp Met
        315                 320                 325

CCC ATC TTC AGC GCC AAT GCC TGG CGG GCA TAC GAC ACC GTC TCT GCC 1239
Pro Ile Phe Ser Ala Asn Ala Trp Arg Ala Tyr Asp Thr Val Ser Ala
        330                 335                 340         345
                                                    ├──VII──
GAG CGC CAC CTC TCT GGG ACA CCT ATC TCC TTC ATC CTG CTC CTC TCT 1287
Glu Arg His Leu Ser Gly Thr Pro Ile Ser Phe Ile Leu Leu Leu Ser
            350                 355                 360

TAC ACC TCC TGC GTC AAC CCC ATC ATC TAC TGC TTC ATG AAC AAA     1335
Tyr Thr Ser Cys Val Asn Pro Ile Ile Tyr Cys Phe Met Asn Lys
        365                 370                 375
```

FIG. 6F

```
CGA TTC CGT CTT GGC TTC ATG GCC ACC TTC CCC TGC TGT CCC AAC CCA    1383
Arg Phe Arg Leu Gly Phe Met Ala Thr Phe Pro Cys Cys Pro Asn Pro
380                         385                         390

GGT ACC CCT GGG GTG AGA GGA GAG ATG GGA GAG GAG GAA GGC AGG        1431
Gly Thr Pro Gly Val Arg Gly Glu Met Gly Glu Glu Glu Gly Arg
        395                         400                         405

ACC ACA GGG GCG TCT TTG TCC AGA TAC TCC TAC AGC CAC ATG AGC ACC    1479
Thr Thr Gly Ala Ser Leu Ser Arg Tyr Ser Tyr Ser His Met Ser Thr
410                         415                         420                         425

TCT GCT CCG CCC CCG TGAGCTGGGC CCGGGGCTAC ACAGTACAGC AGGAAGGAGG    1534
Ser Ala Pro Pro Pro End
                    430

CCACGGGAGG AGGAGGAGAA AAGAAAGGAA AGGAGAAAGC AGGAGAAGCA GGAGGAGGCA  1594

GAAGCAAAAG AGAAGGAAGG CCCAGGT                                      1621
```

FIG. 7

```
GPCCK_AR   1 MSVERAVCQPASPWWEAEARMDVVDSLFVNGSNITSACELGFENETLFCL  50
               ||..  :  ...||||||||::||||||.:||||:||||||||
RTCCK_AR   1 .....MSHSPARQHLVESSRMDVVDSLLMNGSNITPPCELGLENETLFCL  45

51 DRPRPSKEWQPAVQILLYSLIFLLSVLGNTLVITVLIRNKRMRTVTNIFL 100
             |.|.||||||.|:||||||:|||||||||||||||||||||||||||||
          46 DQPQPSKEWQSALQILLYSIIFLLSVLGNTLVITVLIRNKRMRTVTNIFL  95

. II              .           . III .
         101 LSLAVSDLMLCLFCMPFNLIPSLLKDFIFGSAVCKTTTYFMGTSVSVSTF 150
             ||||||||||||||||||||||.||||||||||||||||||||||||||
          96 LSLAVSDLMLCLFCMPFNLIPNLLKDFIFGSAVCKTTTYFMGTSVSVSTF 145

IV .
         151 NLVAISLERYGAICKPLQSRVWQTKSHALKVIAATWCLSFTIMTPYPIYS 200
             |||||||||||||:|||||||||||||||||||||||||||||||||||
         146 NLVAISLERYGAICRPLQSRVWQTKSHALKVIAATWCLSFTIMTPYPIYS 195

.           .           . V
         201 NLVPFTKNNNQTGNMCRFLLPNDVMQQTWHTFLLLILFLIPGIVMMVAYG 250
             |||||||||||:|||||||||.|.|||.|:|||||||:|||||:||||
         196 NLVPFTKNNNQTANMCRFLLPSDAMQQSWQTFLLLILFLLPGIVMVVAYG 245

251 LISLELYQGIKFDAIQKKSAKERKTSTGSSGPMEDSDGCYLQKSRHPRKL 300
             ||||||||||||| |||||||:|.|||||.. ||||||||||.||||
         246 LISLELYQGIKFDASQKKSAKEKKPSTGSSTRYEDSDGCYLQKSRPPRKL 295

. VI .
         301 ELRQLSPSSSGSNRINRIRSSSSTANLMAKKRVIRMLIVIVVLFFLCWMP 350
             ||.|||.:|:||  |:||||||||.|||:||||||||||||||||||||
         296 ELQQLSSGSGGS.RLNRIRSSSSAANLIAKKRVIRMLIVIVVLFFLCWMP 344

. VII
         351 IFSANAWRAYDTVSAERHLSGTPISFILLLSYTSSCVNPIIYCFMNKRFR 400
             ||||||||||||||:|||||||||||||||||||||||||||||||||
         345 IFSANAWRAYDTVSAEKHLSGTPISFILLLSYTSSCVNPIIYCFMNKRFR 394

401 LGFMATFPCCPNPGTPGVRGEMGEEEEGRTTGASLSRYSYSHMSTSAPPP 450
             ||||||||||||.||||||:||||:|||. | |||||||||||||||||
         395 LGFMATFPCCPNPGPPGVRGEVGEEEDGRTIRALLSRYSYSHMSTSAPPP 444
```

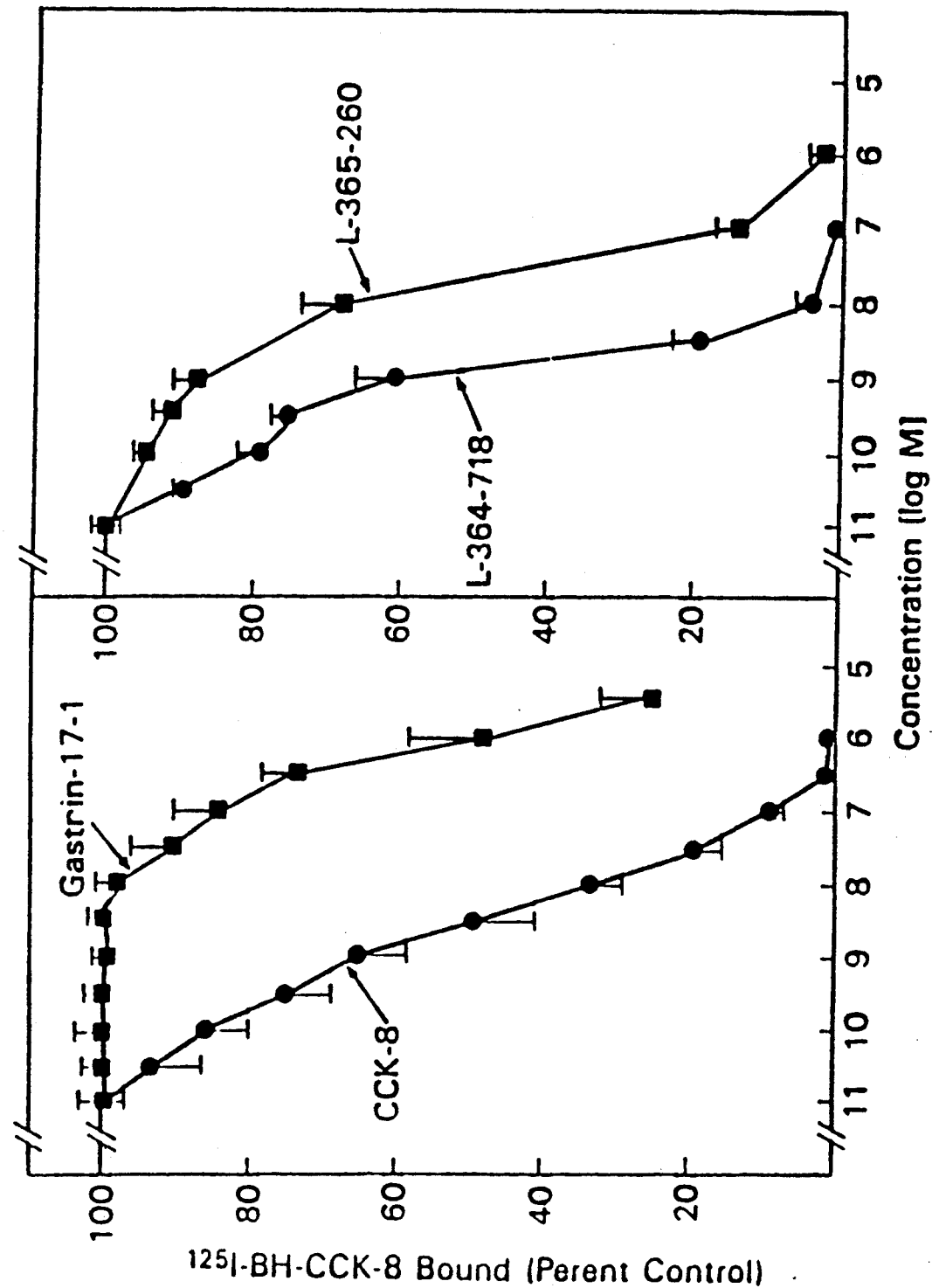

FIG. 9A

```
CTCGGAGGGG CC ATG GAG CTG CTC AAG CTG AAC CGG AGC CTC CAG GGA      48
           Met Glu Leu Leu Lys Leu Asn Arg Ser Leu Gln Gly
            1                  5        ▲              10

CCC GGG CCT GGG CCG GGG GCT CCC CTG TGC CGC CCG GCT GGC CCG CTT    96
Pro Gly Pro Gly Pro Gly Ala Pro Leu Cys Arg Pro Ala Gly Pro Leu
         15                  20                  25

CTC AAC AGC AGT GGT GCA GGC AAC GTC AGC TGC GAA ACC CCT CGC ATC    144
Leu Asn Ser Ser Gly Ala Gly Asn Val Ser Cys Glu Thr Pro Arg Ile
         30             ▲   35                  40

CGA GGC GCC GGG ACG AGA GAA TTG GAG CTG GCC ATC AGA GTC ACC CTT    192
Arg Gly Ala Gly Thr Arg Glu Leu Glu Leu Ala Ile Arg Val Thr Leu
 45                  50                  55                  60

TAC GCA GTG ATC TTT CTG ATG AGC GTT GGA GGA AAT GTG CTC ATC ATT    240
Tyr Ala Val Ile Phe Leu Met Ser Val Gly Gly Asn Val Leu Ile Ile
                 65                  70                  75
```

FIG. 9B

```
GTG GTC CTG GGA CTG AGC CGC CGC CTG AGA ACT GTG ACC AAT GCT TTC    288
Val Val Leu Gly Leu Ser Arg Arg Leu Arg Thr Val Thr Asn Ala Phe
         80                    85                    90

CTG CTC TCC CTG GCA GTC AGT GAC CTC CTG CTG GCT GTG GCT TGC ATG    336
Leu Leu Ser Leu Ala Val Ser Asp Leu Leu Leu Ala Val Ala Cys Met
         95                   100                   105

CCC TTC ACA CTC CTG CCC AAT CTT ATG GGC ACA TTC ATC TTT GGC ACC    384
Pro Phe Thr Leu Leu Pro Asn Leu Met Gly Thr Phe Ile Phe Gly Thr
    110                   115                   120

GTC ATC TGC AAG GCT GTT TCC TAC CTC ATG GGG GTG TCT GTG AGC GTG    432
Val Ile Cys Lys Ala Val Ser Tyr Leu Met Gly Val Ser Val Ser Val
    125                   130                   135             140

TCC ACG CTC AGC CTT GTG GCC ATC GCC CTG GAG CGG TAC AGC GCC ATC    480
Ser Thr Leu Ser Leu Val Ala Ile Ala Leu Glu Arg Tyr Ser Ala Ile
         145                   150                   155

TGC CGA CCA CTG CAG GCT CGA GTG TGG CAG ACC CGC TCC CAC GCT GCT    528
Cys Arg Pro Leu Gln Ala Arg Val Trp Gln Thr Arg Ser His Ala Ala
         160                   165                   170
```

FIG. 9C

```
                                                                              ─IV─
CGC GTG ATT TTA GCC ACT TGG CTG CTC TCC GGA TTG CTC ATG GTC CCC              576
Arg Val Ile Leu Ala Thr Trp Leu Leu Ser Gly Leu Leu Met Val Pro
            175                         180                 185

TAC CCT GTG TAC ACT GCT GTG CAG CCG GTA GGG CCT CGT GTG CTG CAG              624
Tyr Pro Val Tyr Thr Ala Val Gln Pro Val Gly Pro Arg Val Leu Gln
            190                         195                 200

TGC GTG CAT CGC TGG CCC AAC GCA CGG GTC CGC CAG ACC TGG TCA GTA              672
Cys Val His Arg Trp Pro Asn Ala Arg Val Arg Gln Thr Trp Ser Val
205                         210                         215         220
                                                                     ─V─
CTG CTC CTG CTC TTG TTC TTC GTC CCC GGA GTG GTT ATG GCA GTG                  720
Leu Leu Leu Leu Leu Phe Phe Val Pro Gly Val Val Met Ala Val
                225                         230                 235

GCC TAC GGG CTC TAC ATC TCC CGC GAG CTC TAC TTA GGG CTT CGC TTT GAC          768
Ala Tyr Gly Leu Tyr Ile Ser Arg Glu Leu Tyr Leu Gly Leu Arg Phe Asp
            240                         245                         250
```

FIG. 9D

| | | | | | | | | |
|---|---|---|---|---|---|---|---|---|
| GGT Gly | GAC Asp | GCC Ala | GAC Asp | AGT Ser | GAG Glu | AGC Ser 260 | CAG Gln | AGG Arg | GTC Val | CGA Arg | GGC Gly 265 | CCG Pro | GGA Gly | GGT Gly | 816 |

Gly Asp Ala Asp Ser Glu Ser Gln Arg Val Arg Gly Pro Gly Gly
255                 260                     265

CTG TCC GGT TCC GCG CCA GGT CCT GCT CAC CAG AAT GGG CGT TGC CGG   864
Leu Ser Gly Ser Ala Pro Gly Pro Ala His Gln Asn Gly Arg Cys Arg
270                 275                     280

CCT GAA TCT GGC CTG TCA GGC GAG GAC AGC GAC GGC TGC TAT GTG CAA   912
Pro Glu Ser Gly Leu Ser Gly Glu Asp Ser Asp Gly Cys Tyr Val Gln
285                 290                     295                 300

CTG CCA CGG TCT CGG GCC CTG GAG CTG TCG GCC CTG GCG GCG TCC   960
Leu Pro Arg Ser Arg Pro Ala Leu Glu Leu Ser Ala Leu Ala Ala Ser
305                 310                     315

ACC CCT GCA GGA CCT GCA CCC CGG CCC ACC CAG GCC AAG CTG CTG   1008
Thr Pro Ala Gly Pro Ala Pro Arg Pro Thr Gln Ala Lys Leu Leu
320                 325                     330

GCT AAG AAG CGC GTG GTG CGG ATG TTG CTG GTC ATC GTT GTG CTC TTT   1056
Ala Lys Lys Arg Val Val Arg Met Leu Leu Val Ile Val Val Leu Phe
335                 340                     345

```
TTC CTG TGT TGG TTG CCG GTG TAC AGC GCC AAC ACG TGG CGT GCC TTC      1104
Phe Leu Cys Trp Leu Pro Val Tyr Ser Ala Asn Thr Trp Arg Ala Phe
350                 355                 360

GAC GGC CCG GGT GCG CAT CGG GCC CTC TCG GGA GCT GGG ATC TCT TTC      1152
Asp Gly Pro Gly Ala His Arg Ala Leu Ser Gly Ala Pro Ile Ser Phe
365                 370                 375                 380
                                        ├── VII

ATC CAT TTG CTG AGC TAC GCC TCC GCC TGT GTC AAC CCA CTG GTC TAC      1200
Ile His Leu Leu Ser Tyr Ala Ser Ala Cys Val Asn Pro Leu Val Tyr
                385                 390                 395

TGC TTC ATG CAC CGT CCG TTT CGC CAG GCC CTG GAC ACT TGC GCC          1248
Cys Phe Met His Arg Pro Phe Arg Gln Ala Leu Asp Thr Cys Ala
                400                 405                 410

CGC TGC TGC CCT AGG CCT CGA GCT CGT CCC AGG CCT CTC CCA GAG          1296
Arg Cys Cys Pro Arg Pro Arg Ala Arg Pro Arg Pro Leu Pro Glu
            415                 420                 425

GAG GAC CCT CCC ACC CCC ATT CGT TCC AGG CTG TCC AGG CTG AGC TAC      1344
Glu Asp Pro Pro Thr Pro Ile Arg Ser Ile Arg Leu Ser Arg Leu Ser Tyr
430                 435                 440

ACC ATC AGC ACG CTG GGG CCC GGC TGATGGGGGT GGTGGGGGCG                1391
Thr Ile Ser Thr Leu Gly Pro Gly End
445                 450
```

FIG. 9F

```
CTGAGGCAGC ACAGGCATCC TGTAAGCACA AATACATCCA GACACACAAG AAACACAAAC      1451
CACACTTGAC AGAGAGACTA ACACTCAACA GCATCGACTA ACCCAACACT CAGGAAACGG      1511
TGGCATAGTA CACACACACA CACACACACC AGAGCTTTAC ACAGAAAGGA GGCTCCCTGA      1571
GGGCCTTCCT AGAGACAGGG CACTGATCTT GACAGGCAAA CATAGCATCC TTAGCAGCAT      1631
CCTTATGCAC TGGGAACTCT GACAGCTGAC CGGTCCTCAT GCCCACATGC ATTAATCACA      1691
CTGATTCTCT AAGGGCAGCA GACCGTGGCA CAGGACTGAT TTGGGTTATT CCAGGCTGTC      1751
TTTAGTTTGA CATCACAAGA CACTTCTCCC CACCAGCACT GCCCCTACAA CAGGCCTGAT      1811
ACCTTCCTGA CCAACAGGCT CTTTAGGACT AAAAACTCTC TCTTCGTCCC TTTCCAGTTA      1871
AGGACTGCAG CCCTGCCCCC TCATCTTCAC CAGACCTCTT CAAAACACAA TAAATGACTT      1931
GCTCTCAAAA AAAAAAAAA AAAAAAAAGC GGNNGCAGAA TTCGAGCTCG GTACCCGGGG      1991
ATCCCTCTAGA GTCGACCTGC AGGC                                           2015
```

FIG. 10

| | | | | | | | | | |
|---|---|---|---|---|---|---|---|---|---|
| GPCCKBR | MELLKLNRSL | QGPGPGPGAP | LCRPAGPLLN | SSGAGNVSCE | TPRIRGAGTR | ELELAIRVTL | YAVIFLMSVG | GNVLIIVVLG | LSRRLRTVTN | AFLLSLAVSD 100 |
| RTCCKBR | MELLKLNRSV | QGPGPGPGSS | LCRPGVS..LN | SSSAGNLSCE | PPRIRQTGTR | ELEMAIRHTL | YAVIFLMSVG | GNVLIIVVLG | LSRRLRTVTN | AFLLSLAVSD 100 |
| CANGASR | MELLKLNRSA | QGGGAGPGAS | LCRAGALLN | SSEAGNLSCE | PPRLRGAGTR | ELELAIRVTL | YAVIFLMSVG | GNVLIIVVLG | LSRRLRTVTN | AFLLSLAVSD 100 |

| | | | | | | | | | |
|---|---|---|---|---|---|---|---|---|---|
| GPCCKBR | LLLAVACMPF | TLLPNLMGTF | IFGTVICKAV | SYLMGVSVSV | STLSLVAIAL | ERYSAICRPL | QARVWQTRSH | AARVILATWL | LSGLLMVPYP | VYTAVQP.VG 199 |
| RTCCKBR | LLLAVACMPF | TLLPNLMGTF | IFGTVICKAL | SYLMGVSVSV | STLNVAIAL | ERYSAICRPL | QARVWQTRSH | AARVILATWL | LSGLLMVPYP | VYTMVQP.VG 199 |
| CANGASR | LLLAVACMPF | TLLPNLMGTF | IFGTVVCKAV | SYLMGVSVSV | STLSLVAIAL | ERYSAICRPL | QARVWQTRSH | AARVIIATMM | LSGLLMVPYP | VYTAVQPAGG 200 |

| | | | | | | | | | |
|---|---|---|---|---|---|---|---|---|---|
| GPCCKBR | PRVLQCVHRW | PNARVRQTWS | VLLLLLLFFV | PGVWMAVAYG | LISRELYLGL | RFDGDADSES | QSRVRGPGGL | SGSA.PGPAH | QNGRCRPESG | LSGEDSDGCY 298 |
| RTCCKBR | PRVLQCVHRW | PSARVRQTWS | VLLLLLLFFI | PGVMAVAYG | LISRELYLGL | HDGENDSET | QSRARNQGGL | PGGAAPGRM | QNGGCRPVTS | VAGEDSDGCC 299 |
| CANGASR | ARALQCVHRW | PSARVRQTWS | VLLLLLLFFV | PGVMAVAYG | LISRELYLGL | RFDEDSE. | .SRVRSQGGL | RGGAGPGPAP | PNGSCRPEGG | LAGEDDGCY 298 |

| | | | | | | | | | |
|---|---|---|---|---|---|---|---|---|---|
| GPCCKBR | VQLPRSRPAL | ELSALAASTP | APGPGPRPTQ | AKLLAKKRVV | RMLLVIVVLF | FLCWLPVYSA | NTWRAFDGPG | AHRALSGAPI | SFIHLLSYAS | ACVNPLVYCF 398 |
| RTCCKBR | VQLPRSR..L | EMTL.TPTP | GPMPGPRPNQ | AKLLAKKRVV | RMLLVIVLLF | FLCWLPVYSV | NTWRAFDGPG | AQRALSGAPI | SFIHLLSYTS | ACVNPLVYCF 397 |
| CANGASR | VQLPRSRQTL | ELSALTAPTP | GPGGPRPYM | AKLLAKKRVV | RMLLVIVVLF | FLCWLPLYSA | NTWRAFDESS | AHRALSGAPI | SFIHLLSYAS | ACVNPLVYCF 398 |

| | | | | |
|---|---|---|---|---|
| GPCCKBR | MHRPFRQACL | DTCARCCPRP | PRARPRPLPE | EDPPTPSIRS | LSRLSYTTIS | TLGPG* 453 |
| RTCCKBR | MHRRFRQACL | DTCARCCPRP | PRARPPLPD | EDPPTPSTAS | LSRLSYTTIS | TLGPG* 452 |
| CANGASR | MHRRFRQACL | ETCARCCPRP | PRARPRPLPD | EDPPTPSTAS | LSRLSYTTIS | TLGPG* 453 |

FIG. 12A human CCKB receptor

| ATG | GAG | CTG | CTC | AAG | CTG | AAC | CGG | AAC | GTG | CAG | GGA | ACC | GGA | CCC | GGG | | 48 |
|---|---|---|---|---|---|---|---|---|---|---|---|---|---|---|---|---|---|
| Met | Glu | Leu | Leu | Lys | Leu | Asn | Arg | Asn | Val | Gln | Gly | Thr | Gly | Pro | Gly | | |
| 1 | | | | 5 | | | | | 10 | | | | | 15 | | | |

| CCG | GGG | GCT | TCC | CTG | TGC | CGC | CCG | GGG | GCG | CCT | CTC | AAC | AGC | AGC | | 96 |
|---|---|---|---|---|---|---|---|---|---|---|---|---|---|---|---|---|
| Pro | Gly | Ala | Ser | Leu | Cys | Arg | Pro | Gly | Ala | Pro | Leu | Leu | Asn | Ser | Ser | |
| | | | 20 | | | | | 25 | | | | | 30 | | | |

| AGT | GTG | GGC | AAC | CTC | AGC | TGC | GAG | CCC | CCT | CGC | ATT | CGC | GGA | GCC | GGG | 144 |
|---|---|---|---|---|---|---|---|---|---|---|---|---|---|---|---|---|
| Ser | Val | Gly | Asn | Leu | Ser | Cys | Glu | Pro | Pro | Arg | Ile | Arg | Gly | Ala | Gly | |
| | | 35 | | | | | 40 | | | | | 45 | | | | |

| ACA | CGA | GAA | TTG | GAG | CTG | GCC | ATT | AGA | ATC | ACT | CTT | TAC | GCA | GTG | ATC | 192 |
|---|---|---|---|---|---|---|---|---|---|---|---|---|---|---|---|---|
| Thr | Arg | Glu | Leu | Glu | Leu | Ala | Ile | Arg | Ile | Thr | Leu | Tyr | Ala | Val | Ile | |
| 50 | | | | | 55 | | | | | 60 | | | | | | |

| TTC | CTG | ATG | AGC | GTT | GGA | GGA | AAT | ATG | CTC | ATC | ATC | GTG | GTC | CTG | GGA | 240 |
|---|---|---|---|---|---|---|---|---|---|---|---|---|---|---|---|---|
| Phe | Leu | Met | Ser | Val | Gly | Gly | Asn | Met | Leu | Ile | Ile | Val | Val | Leu | Gly | |
| 65 | | | | 70 | | | | | 75 | | | | | 80 | | |

| CTG | AGC | CGC | CGC | CTG | AGG | ACT | GTC | ACC | AAT | GCC | TTC | CTC | CTC | TCA | CTG | 288 |
|---|---|---|---|---|---|---|---|---|---|---|---|---|---|---|---|---|
| Leu | Ser | Arg | Arg | Leu | Arg | Thr | Val | Thr | Asn | Ala | Phe | Leu | Leu | Ser | Leu | |
| | 85 | | | | | 90 | | | | | 95 | | | | | |

FIG. 12B

```
GCA GTC AGC GAC CTC CTG CTG GCT TGC ATG CCC TTC ACC CTC         336
Ala Val Ser Asp Leu Leu Leu Ala Cys Met Pro Phe Thr Leu
            100                 105                 110

CTG CCC AAT CTC ATG GGC ACA TTC ATC TTT GGC ACC GTC ATC TGC AAG 384
Leu Pro Asn Leu Met Gly Thr Phe Ile Phe Gly Thr Val Ile Cys Lys
            115                 120                 125

GCG GTT TCC TAC CTC ATG GGG GTG TCT GTG AGT GTG TCC ACG CTA AGC 432
Ala Val Ser Tyr Leu Met Gly Val Ser Val Ser Val Ser Thr Leu Ser
        130                 135                 140

CTC GTG GCC ATC GCA CTG GAG CGG TAC AGC GCC ATC TGC CGA CCA CTG 480
Leu Val Ala Ile Ala Leu Glu Arg Tyr Ser Ala Ile Cys Arg Pro Leu
145                 150                 155                 160

CAG GCA CGA GTG TGG CAG ACG CGC TCC CAC GCG GCT CGC GTG ATT GTA 528
Gln Ala Arg Val Trp Gln Thr Arg Ser His Ala Ala Arg Val Ile Val
            165                 170                 175

GCC ACG TGG CTG CTG TCC GGA CTA CTC ATG GTG CCC TAC CCC GTG TAC 576
Ala Thr Trp Leu Leu Ser Gly Leu Leu Met Val Pro Tyr Pro Val Tyr
        180                 185                 190

ACT GTC GTG CAA CCA GTG GGG CCT CGT GTG CTG CAG TGC GTG CAT CGC 624
Thr Val Val Gln Pro Val Gly Pro Arg Val Leu Gln Cys Val His Arg
        195                 200                 205

TGG CCC AGT GCG CGG GTC CGC CAG ACC TGG TCC GTA CTG CTT CTG CTG 672
Trp Pro Ser Ala Arg Val Arg Gln Thr Trp Ser Val Leu Leu Leu Leu
210                 215                 220
```

FIG. 12C

```
CTC TTG TTC ATC CCG AGT GTG GTT ATG GCC GTG TAC GGG CTT             720
Leu Leu Phe Ile Pro Ser Val Val Met Ala Val Tyr Gly Leu
225           230           235           240

ATC TCT CGC GAG CTC TAC TTA GGG CTT CGC TTT GAC GGC GAC AGT GAC     768
Ile Ser Arg Glu Leu Tyr Leu Gly Leu Arg Phe Asp Gly Asp Ser Asp
          245              250              255

AGC GAC AGC CAA AGG GTC CGA AAC CAA GGC TTT GAC GGC CTG CCA GGG GCT 816
Ser Asp Ser Gln Arg Val Arg Asn Gln Gly Phe Asp Gly Leu Pro Gly Ala
        260              265              270

GTT CAC CAG AAC GGG CGT TGC CGG CCT GAG ACT GGC GCG GTT GGC GAA     864
Val His Gln Asn Gly Arg Cys Arg Pro Glu Thr Gly Ala Val Gly Glu
        275              280              285

GAC AGC GAT GGC TGC TAC GTG CAA CTT CCA CGT TCC CGG CCT GCC CTG     912
Asp Ser Asp Gly Cys Tyr Val Gln Leu Pro Arg Ser Arg Pro Ala Leu
        290              295              300

GAG CTG ACG GCG CTG ACG GCT CCA GGG CCG GGA TCC GGC TCC CGG CCC     960
Glu Leu Thr Ala Leu Thr Ala Pro Gly Pro Gly Ser Gly Ser Arg Pro
        305              310              315              320
```

FIG. 12D

| ACC | CAG | GCC | AAG | CTG | GCT | AAG | AAG | CGC | GTG | GTG | CGA | ATG | TTG | CTG | 1008 |
|---|---|---|---|---|---|---|---|---|---|---|---|---|---|---|---|
| Thr | Gln | Ala | Lys | Leu | Ala | Lys | Lys | Arg | Val | Val | Arg | Met | Leu | Leu | |
| | | | | 325 | | | | 330 | | | | | | 335 | |

| GTG | ATC | GTT | GTG | CTT | TTT | TTT | CTG | TGT | TGG | TTG | CCA | GTT | TAT | AGT | GCC | 1056 |
|---|---|---|---|---|---|---|---|---|---|---|---|---|---|---|---|---|
| Val | Ile | Val | Val | Leu | Phe | Phe | Leu | Cys | Trp | Leu | Pro | Val | Tyr | Ser | Ala | |
| | | | 340 | | | | 345 | | | | | 350 | | | | |

| AAC | ACG | TGG | CGC | GCC | TTT | GAT | GGC | CCG | GGT | GCA | CAC | CGA | GCA | CTC | TCG | 1104 |
|---|---|---|---|---|---|---|---|---|---|---|---|---|---|---|---|---|
| Asn | Thr | Trp | Arg | Ala | Phe | Asp | Gly | Pro | Gly | Ala | His | Arg | Ala | Leu | Ser | |
| | 355 | | | | | 360 | | | | | 365 | | | | | |

| GGT | GCT | CCT | ATC | TCC | TTC | ATT | CAC | TTG | CTG | AGC | TAC | GCC | TCG | GCC | TGT | 1152 |
|---|---|---|---|---|---|---|---|---|---|---|---|---|---|---|---|---|
| Gly | Ala | Pro | Ile | Ser | Phe | Ile | His | Leu | Leu | Ser | Tyr | Ala | Ser | Ala | Cys | |
| 370 | | | | | 375 | | | | | 380 | | | | | | |

| GTC | AAC | CCC | CTG | GTC | TAC | TGC | TTC | ATG | CAC | CGT | CGC | TTT | CGC | CAG | GCC | 1200 |
|---|---|---|---|---|---|---|---|---|---|---|---|---|---|---|---|---|
| Val | Asn | Pro | Leu | Val | Tyr | Cys | Phe | Met | His | Arg | Arg | Phe | Arg | Gln | Ala | |
| 385 | | | | | 390 | | | | | 395 | | | | | 400 | |

| TGC | CTG | GAA | ACT | TGC | GCT | CGC | TGC | TGC | CCC | CGG | CCT | CCA | CGA | GCT | CGC | 1248 |
|---|---|---|---|---|---|---|---|---|---|---|---|---|---|---|---|---|
| Cys | Leu | Glu | Thr | Cys | Ala | Arg | Cys | Cys | Pro | Arg | Pro | Pro | Arg | Ala | Arg | |
| | | | 405 | | | | | 410 | | | | | | 415 | | |

FIG. 12E

```
CCC AGG GCT CTT CCC GAT GAG GAC CCT CCC ACT CCC ATT GCT TCG      1296
Pro Arg Ala Leu Pro Asp Glu Asp Pro Pro Thr Pro Ser Ile Ala Ser
            420                     425                     430

CTG TCC AGG CTT AGC TAC ACC ACC ATC AGC ACA CTG GGC CCT GGC TGAGGAGTAG  1351
Leu Ser Arg Leu Ser Tyr Thr Thr Ile Ser Thr Leu Gly Pro Gly End
            435                     440                     445

AGGGGCCGTG GGGGTTGAGG CAGGGCAAAT GACATGCACT GACCCTTCCA GACATAGAAA       1411

ACACAAACCA CAACTGACAC AGGAAACCAA CACCCAAAGC ATGGACTAAC CCCAACGACA       1471

GGAAAAGGTA GCTTACCTGA CACAAGAGGA ATAAGAATGG AGCAGTACAT GGGAAAGGAG      1531

GCATGCCTCT GATATGGGAC TGAGCCTGGC CCATAGAAAC ATGACACTGA CCTTGGAGAG      1591

ACACAGCGTC CCTAGCAGTG AACTATTTCT ACACAGTGGG AACTCTGACA AGGGCTGACC      1651

TGCCTCTCAC ACACATAGAT TAATGGCACT GATTGTTTTA GAGACTATGG AGCCTGGCAC      1711

AGGACTGACT CTGGGATGCT CCTAGTTTGA CCTCACAGTG ACCCTTCCCA ATCAGCACTG      1771

AAAATACCAT CAGGCCTAAT CTCATACCTC TGACCAACAG GCTGTTCTGC ACTGAAAAGG      1831

TTCTTCATCC CTTTCCAGTT AAGGACCGTG GCCCTGCCCT CTCCTTCCTT CCCAAACTGT      1891

TCAAGAAATA ATAAATTGTT TGGCTTCCTC CTGAAAAAAA AAAAAAAAAA AAAAAAAAAA      1951

AAAAAAAAAA GGAATTCC                                                     1969
```

METHOD OF PURIFYING CHOLECYSTOKININ RECEPTOR PROTEIN

The present application is a continuation in part of U.S. application Ser. No. 07/928,033, filed Aug. 11, 1992, and a continuation in part of U.S. application Ser. No. 07/861,769, filed Apr. 1, 1992, now abandoned, which is a continuation in part of U.S. application Ser. No. 07/831,248, filed Feb. 7, 1992, now abandoned.

BACKGROUND OF THE INVENTION

The present invention relates to the purification of cholecystokinin (CCK) receptor protein to sequenceable-grade homogeneity. The present invention further relates to obtaining and expressing DNAs that code for CCK receptor protein.

A family of cholecystokinin peptides was originally isolated from the mammalian gastrointestinal tract and was one of the first gastrointestinal peptides to be discovered in the brain. The predominant molecular form of CCK peptide is cholecystokinin-octapeptide (CCK-8) which exists in a sulfated and non-sulfated form.

The cholecystokinin family of receptors is widely distributed throughout the gastrointestinal and central nervous systems where they regulate pancreatic and gastric secretion, smooth muscle motility, growth, anxiety and satiety, analgesia and neuroleptic activity. The receptor family includes $CCK_A$ and $CCK_B$/gastrin receptors by virtue of their affinity for a structurally and functionally related family of peptides, including CCK and CCK analogues having identical COOH terminal pentapeptide sequence and varying sulfation at the sixth (gastrin) and seventh (CCK) tyrosyl residues. $CCK_B$ receptors more recently have been designated $CCK_B$/gastrin receptors because of the suspected homology, perhaps even identity, between $CCK_B$ and gastrin receptors. (Kopin et al., PNAS USA 89: 3605 (1992).

Recently, nonpeptide agonists highly selective for each of the CCK receptor subtypes have been developed and further support the subtype classification. The most potent and selective antagonists are L-364,718 for $CCK_A$ and L-365,260 and PD134408 for $CCK_B$/gastrin receptors. The $CCK_A$ receptor differs from $CCK_B$/gastrin receptor particularly in its selectivity for CCK peptide analogues with a sulfate at the seventh position from the COOH terminus.

The $CCK_A$ receptor mediates physiologic gallbladder contraction, pancreatic growth and enzyme secretion, delayed gastric emptying, relaxation of the sphincter of Oddi and potentiation of insulin secretion. The $CCK_A$ receptor also appears in the anterior pituitary, in the myenteric plexus, and in areas of the CNS (midbrain) where CCK interaction with dopaminergic neurons has been implicated in the pathogenesis of Schizophrenia, Parkinson's disease, drug addition and feeding disorders. Experimental rat pancreatic carcinogenesis is promoted by CCK through the $CCK_A$ receptor.

$CCK_A$ receptors in pancreatic acinar cells have been most well characterized because of the ability to prepare a homogeneous preparation of a hormonally responsive effector system in dispersed acini. In pancreatic acinar cells, CCK peptide interacts specifically with its cell surface receptor which is coupled to a quanine nucleotide regulatory protein (G protein) which activates phospholipase C, breakdown of phosphoinositides, mobilization of intracellular calcium and activation of protein kinase C.

$CCK_A$ receptors have been functionally expressed in the plasma membrane of oocytes after injection of rat brain total RNA, and of mRNA from rat pancreatic acinar carcinoma cell line, AR42J. Affinity labeling studies of $CCK_A$ receptors from rat pancreas and partial purification demonstrate an 85–95 kDa, heavily glycosylated, binding subunit with a deglycosylated core protein of 42 kDa.

The $CCK_B$/gastrin receptor is found predominantly throughout the CNS, where it is thought to modulate anxiety and neuroleptic activity. Interaction between CCK peptide and $CCK_B$/gastrin receptors on mesocorticolimbic, dopaminergic neurons influences the physiological states of stress and anxiety. The presence of $CCK_B$/gastrin receptors on peripheral monocytes and monocyte-derived splenic cells suggests that CCK plays a role in the long suspected neuroendocrine modulation of the immune system.

$CCK_B$/gastrin receptors, found on gastric parietal and chief cells, and gastrointestinal smooth muscle cells, regulate acid and pepsinogen secretion, and gastrointestinal motility, respectively. They are also present on some human gastric and colon cancer cells where they may regulate growth. CCK peptide, acting at peripheral $CCK_A$ receptors and at central $CCK_A$ and $CCK_B$/gastrin receptors plays a significant role in the nervous system control of appetite.

Attempts have been made to purify CCK receptor protein to homogeneity, but these efforts were unsuccessful. Duong et al., J. Biol. Chem. 264: 17990–96 (1989), used digitonin-solubilized rat pancreatic receptor to obtain a receptor preparation estimated to be of 80% purity. The Doung purification scheme included a three-step purification process utilizing cation exchange, Ulex europaeus agglutinin-I-agarose, and Sephacryl S-300. Szecowka et al., Regulatory Peptides 24: 215–24 (1989), employed a two-step purification scheme to partially purify digitonin-solubilized rat pancreatic receptor that included lectin and CCK affinity chromatography.

Researchers labored unsuccessfully for years to illuminate the molecular structure of CCK receptor protein, but were limited by the inability to purify receptor protein to a homogeneity sufficient for sequencing purposes. Instead, attempts to obtain a purified preparation yielded a partially purified CCK receptor, along with non-CCK receptor proteins. As a result, the accuracy in studies relating, for example, to binding affinities and electrophysiology, was compromised by the inability to study a particular subtype without contamination by another type. Further, the inability to purify CCK receptor to sequenceable homogeneity prohibited cloning of receptor-encoding DNAs and the recombinant expression of a particular CCK receptor in a transformed cell line.

SUMMARY OF THE INVENTION

It is therefore an object of the present invention to provide a method for obtaining CCK receptor protein, in a homogeneous form suitable for amino acid sequencing.

It is also an object of the present invention to provide DNA molecules that encode CCK receptor protein, as well as host cells that are transformed with such a DNA and that expresses functional CCK receptor protein.

In accomplishing these and other objects, there has been provided, in accordance with one aspect of the present invention, an isolated DNA molecule encoding a CCK receptor protein. In a preferred embodiment, the DNA molecule comprises a first nucleotide sequence that consists of nucleotides 199 to 1485 of FIG. 1A, B, C, D and E (SEQ ID No:13), or a DNA sequence which hybridizes under high stringency conditions to an oligonucleotide probe consisting of nucleotides 199 to 1485. In another preferred embodiment, a DNA molecule can comprise, in addition to the aforementioned first nucleotide sequence, a second nucleotide sequence consisting of nucleotides 154 to 198 of FIG. 1A (SEQ ID NO:13), which second nucleotide sequence is positioned immediately upstream of nucleotide 199 of the first nucleotide sequence.

In another preferred embodiment, an isolated DNA molecule encoding a CCK receptor protein comprises a nucleotide sequence consisting of nucleotides 136 to 1491 of FIG. 2A, B, C, D and E (SEQ ID NO:15) or a DNA sequence which hybridizes under high stringency conditions to an oligonucleotide probe consisting of nucleotides 136 to 1491 of FIG. 2A, B, C, D and E (SEQ ID NO:15).

In another preferred embodiment of the invention, an isolated DNA molecule encoding a CCK receptor protein comprises a nucleotide sequence consisting of nucleotides 1 to 1341 of FIG. 12A, B, C, D and E (SEQ ID NO:28) or a DNA sequence which hybridizes under high stringency conditions to an oligonucleotide probe consisting of nucleotides 1 no 1341 of FIG. 12A, B, C, D and E (SEQ ID NO:28).

In accordance with another aspect of the present invention, an isolated CCK receptor protein is provided that is sufficiently pure to be sequencable. The isolated CCK receptor protein can have the amino acid sequence shown, for example, in any of FIG. 1A, B, C, D and E, 2A, B, C, D and E and 12A, B, C, D and E (SEQ ID NOS. 14, 16 and 29, respectively). In another preferred embodiment, an isolated CCK receptor protein having an amino acid sequence corresponding to that of amino acids 16-444 of FIG. 1A and B (SEQ ID NO:14) is provided.

In accordance with another aspect of the present invention, a cell is provided that is transformed with a DNA molecule encoding a CCK receptor protein, where the cell expresses a heterologous polypeptide that possesses a biological activity characteristic of CCK receptor protein.

In accordance with yet another aspect of the present invention, a method is provided for purifying a cholecystokinin receptor, comprising the steps of (a) solubilizing a biological preparation containing cholecystokinin receptor in 1% digitonin, (b) applying the solubilized receptor preparation to a cationic exchange resin and purifying the eluate of the resin, (c) applying the purified eluate to an agarose-bound lectin, and (d) applying an eluate of step (c) to a cibacron blue sepharose column.

BRIEF DESCRIPTION OF THE DRAWINGS

FIG. 1A, B, C, D and E. Nucleotide and deduced amino acid sequences (SEQ ID NOS. 13 and 14) of the rat pancreatic $CCK_A$ receptor cDNA clone. The solid lines labelled with Roman numerals delineate the putative seven transmembrane domains predicted by Kyte Doolittle criteria, see J. Mol. Biol. 157: 105–32 (1982), and homology with other G-protein receptor superfamily members. Amino acid sequence enclosed within brackets and labelled with Arabic numerals correspond to the five internal peptide sequences obtained following CNBr cleavage or Lys-C digestion of the purified $CCK_A$ receptor protein. The triangles indicate four potential sites of N-linked glycosylation.

FIG. 2A, B, C, D, E and F. Nucleotide and deduced amino acid sequences (SEQ ID NOS. 15 and 16) of the rat brain $CCK_B$ receptor cDNA clone. The solid lines labelled with Roman numerals I-VII delineate the putative transmembrane domains predicted by Kyte-Doolittle criteria and homology with $CCK_A$ type receptor, as well as other G-protein-coupled receptor superfamily members. The solid triangles indicate four potential sites for N-linked glycosylation. The solid bars indicate the three potential sites for serine phosphorylation and the solid circles indicate cysteine residues, which are potential sites for either disulfide bridge formation (residues #127 and #205) or palmitoylation (residue #413).

FIG. 3A and B. Alignment of the rat $CCK_B$ receptor (RCCKBR), SEQ ID NO:16 rat $CCK_A$ receptor (RCCKAR), SEQ ID NO: 14 mouse gastrin-releasing peptide receptor (MGRPR), SEQ ID NO: 17 rat substance K receptor (RSKR), SEQ ID NO:19 rat substance P receptor (RSPR) SEQ ID NO:20 and rat neuromedin B receptor (RNMBR), SEQ ID NO:18 protein sequences. The sequence of rat neuromedin K receptor (RNMKR, SEQ ID NO:21) is also shown in this Figure. Using the Pileup program sequence analysis package of the Genetics Computer Group, see Devereux et al., Nucleic Acids Research. 12: 387, (1984), the $CCK_B$ receptor deduced amino acid sequence (SEQ ID NO:16) was aligned for maximal homology to the deducted protein sequences of the $CCK_A$ receptor (SEQ ID NO:14) and the five sequences (mouse gastrin-releasing peptide, rat neuromedin B rat neuromedin K, rat substance K and rat substance P receptors), SEQ ID NOS. 17, 18 21, 19 and 20, respectively found to be the most be homologous upon searching the Swissprot. release #20 and Pir. release #30 protein data banks. Shown here using single letter abbreviations for amino acids is the result of this alignment with shaded areas denoting conserved amino acids. The number of residues in the variable C terminus not displayed are in parenthesis. Solid lines labelled with Roman numerals indicate the seven putative transmembrane domains.

Figure 4A:
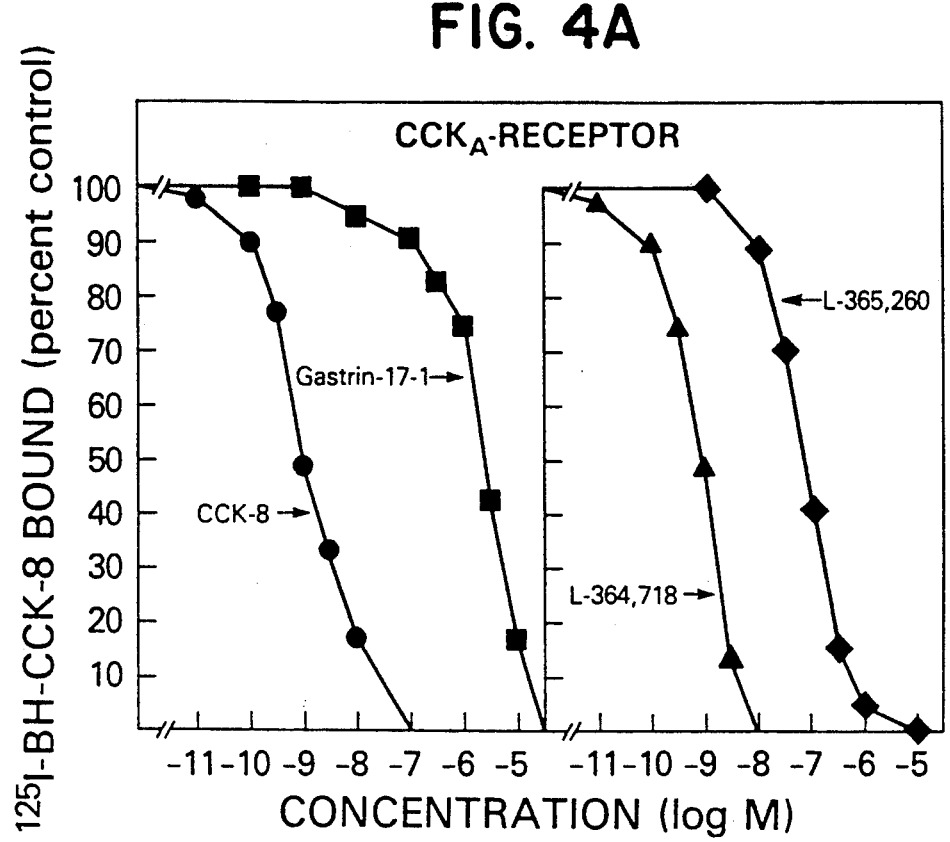
FIG. 4A and B. Ability of CCK receptor agonists and antagonists to inhibit binding of $^{125}$I-BH-CCK-8 to COS-7 cells expressing either $CCK_A$ or $CCK_B$ receptors. COS-7 cells were transfected with the expression vector pCDL-SRα containing either the $CCK_A$ (top panel) or the $CCK_B$ (bottom panel) receptor cDNA sequences. $^{125}$I-BH-CCK8 (50 pM) was incubated either alone or with increasing concentrations of agonists (CCK-8 and gastrin-17-1) (left panel) or antagonists (L-364,718 and L-365,260) (right panel). Data is presented as percent saturable binding (total binding in the presence of radiolabelled hormone alone minus binding in the presence of 1 μM CCK-8). Each experiment was performed in duplicate and the results given are the means from at least two separate experiments.

A. Response to agonists. Application of 1 μM CCK-8 (vertical arrows) elicits a response which desensitizes with repeated applications in the same oocyte. Application of 1 μM gastrin-releasing peptide and 4 μM substance P (diagonal arrows), interspersed between response evoking applications of CCK-8, fail to elicit responses. B. Inhibition by the specific $CCK_A$ receptor antagonist, L-364,718. Application of 1 μM CCK-8 (vertical arrows) to the same oocyte shown in (A) two days after mRNA injection elicits a response which is completely inhibited by the coapplication of 5 μM L-364,718 (diagonal arrow). The response to 1 μM CCK-8 could not be restored following antagonist application despite prolonged washes with buffer. Experiments were repeated several times (n=12 for (A) and n=10 for (B)) in different oocytes, with similar results.

FIG. 6A, B, C, D, E and F. Nucleotide and deduced amino acid sequence (SEQ ID NOS. 22 and 23) of the $CCK_A$ receptor in guinea pig gallbladder and pancreas. The solid lines labelled with Roman numerals delineate the putative seven transmembrane domains predicted by Kyte-Doolittle criteria and homology with the other G-protein coupled receptor superfamily members. The solid triangles indicate the potential sites for N-linked glycosylation. The solid lines indicate potential sites for serine and threonine phosphorylation.

FIG. 7. Alignment of the guinea pig $CCK_A$ receptor (GPCCKAR and rat $CCK_A$ receptor (RTCCKAR) deduced protein sequences (SEQ ID NOS. 24 and 14, respectively). Using the gap program sequence analysis package of the Genetics Research Group the guinea pig $CCK_A$ receptor deduced protein sequence was aligned for maximal homology with the rat $CCK_A$ receptor deduced protein sequence. Solid lines denote amino acid identity, and dotted lines denote conservative substitutions. Solid lines labeled with Roman numerals indicate the seven putative transmembrane domains.

FIG. 8. Ability of CCK receptor agonists and antagonists to inhibit $^{121}$I-BH-CCK-8 to COS-7 cells expressing guinea pig $CCK_A$ receptor. COS-7 cells were transfected with the expression vector pCDL-SRα containing the $CCK_A$ receptor cDNA sequence. $^{125}$I-BH-CCK 8 (50 pM) was incubated either alone or with increasing concentrations of agonists (CCK-8 and Gastrin-17-1) (left panel) or antagonists (L-364,718 and L-365,260) (right panel). Data are presented as percent saturable binding (total binding in presence of radiolabelled hormone alone minus binding in the presence of 1 μM CCK-8). The results given are means of values from at least three experiments performed in duplicate. Vertical bars are standard deviations from the mean.

FIG. 9A, B, C, D, E and F. Nucleotide and deduced amino acid sequence (SEQ ID NOS. 25 and 26) of the $CCK_B$ receptor in guinea pig gallbladder and pancreas. The solid lines labeled with Roman numerals delineate the putative seven transmembrane domains predicted by Kyte-Doolittle criteria and homology with other G-protein coupled receptor superfamily members. The solid triangles indicate the potential sites for N-linked glycoyslation. The solid lines indicate potential sites for serine and threonine phosphorylation.

FIG. 10. Alignment of the guinea pig $CCK_B$ receptor (GPCCKBR), SEQ ID NO:26 with the rat $CCK_B$ receptor (RTCCKBR), SEQ ID NO:16 and the canine gastrin receptor (CANGASR), SEQ ID NO:27 deduced protein sequences. Using the Pileup program sequence analysis package of the Genetics Research Group, the guinea pig $CCK_B$ receptor deduced protein sequence was aligned for maximal homology with the rat $CCK_B$ receptor and canine gastrin receptor deduced protein sequences. Solid lines labeled with Roman numerals indicate the seven putative transmembrane domains. Boxed areas denote amino acids not identical between the guinea pig $CCK_B$ receptor and the rat $CCK_B$ and/or gastrin receptors.

Figure 11:
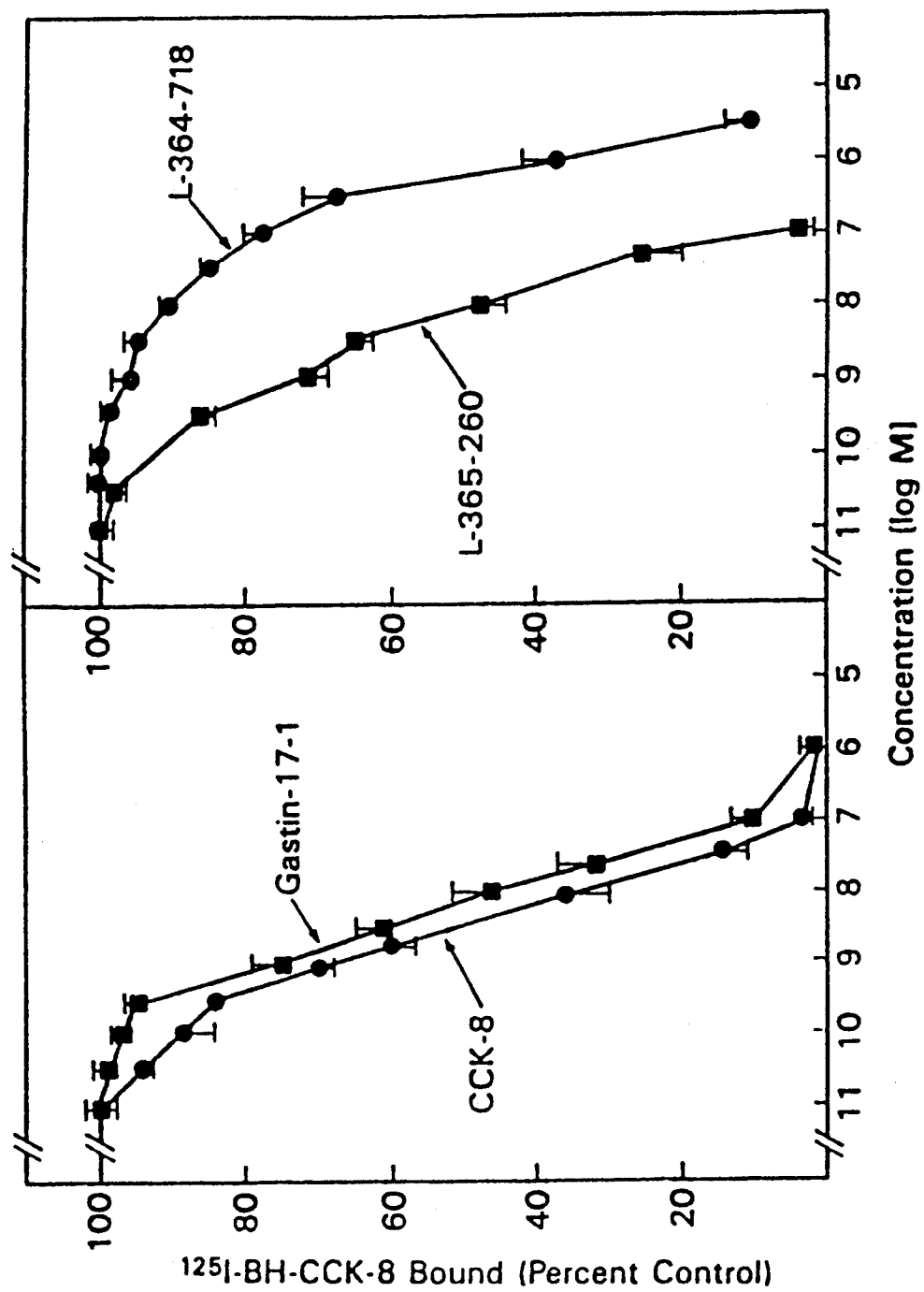

FIG. 11. Ability of CCK receptor agonists and antagonists to inhibit $^{125}$BH-CCK-8 to COS-7 cells expressing the guinea Pig $CCK_B$ receptor. COS-7 cells were transfected with the expression vector pCDL-SRα containing the $CCK_B$ receptor cDNA sequence. $^{125}$I-BH-CCK 8 (50 pM) was incubated either alone or with increasing concentrations of agonists (CCK-8 and Gastrin-17-1) (left panel or antagonists (L-364,718 and L-365,260) (right panel). Data are presented as percent saturable binding (total binding in the presence of radiolabelled hormone alone minus binding in the presence of 1 μM CCK-8). The results given are means of values from at least three experiments performed in duplicate. Vertical bars are standard deviations from the mean.

FIG. 12A, B, C, D and E. The nucleotide and deduced amino acid sequences (SEQ ID NOS. 28 and 29) of the human $CCK_B$ receptor cDNA for both brain and stomach.

DETAILED DESCRIPTION OF PREFERRED EMBODIMENTS

An unconventional approach to purifying CCK receptor protein to sequenceable-grade homogeneity has been discovered. By means of this approach, CCK receptor protein now can be obtained and sequenced routinely from a variety of sources. From the sequence information thus obtained it is possible, pursuant to the present invention, to prepare oligonucleotides suitable for cloning CCK receptor genes.

In this context, "CCK receptor" denotes any from a group of proteins that displays a characteristic CCK binding affinity and that is encoded by a nucleotide sequence which hybridizes an oligonucleotide probe designed in accordance with the criteria elaborated herein.

Examples of CCK receptors proteins obtained and sequenced according to the invention include, but are not limited to, $CCK_A$ and $CCK_B$/gastrin receptors. By means of the present invention, it has been discovered that the $CCK_B$ and gastrin receptors are the same protein and possess identical nucleotide sequences in both dog and rat species. Accordingly, the $CCK_B$/gastrin receptor is designated simply as $CCK_B$ receptor, hereinafter.

With regard to probe design, for example, polymerase chain reaction (PCR) primers can be made utilizing polynucleotide regions common to both the $CCK_A$ gene and the $CCK_B$ gene, such as a portion of the coding sequence which encodes one or more of the seven transmembrane domains (see FIGS. 1A, B, C, D and E and 2A, B, C, D, E and F). PCR primers designed along these lines can be degenerate in order to hybridize to members of the CCK receptor family that are not identical to $CCK_A$ or $CCK_B$ receptor.

A DNA molecule that is a coding sequence for a CCK receptor protein is defined according to the present invention. In preferred embodiments, the DNA molecule comprises a nucleotide sequence consisting of nucleotides 199 to 1485 of FIG. 1A, B, C, D and E (SEQ ID NO:13), or of nucleotides 154 to 1485 of FIG. 1A, B, C, D and E SEQ ID NO:13 or of a DNA sequence which hybridizes under high stringency conditions to an oligonucleotide probe consisting of nucleotides 199 to 1485. In another preferred embodiment, the molecule comprises nucleotides 136 to 1471 of FIG. 2A, B, C, D and E (SEQ ID NO:15) or a DNA sequence which hybridizes under high stringency conditions to an oligonucleotide probe consisting of nucleotides 136 to 1491. In yet another preferred embodiment, the molecule comprises nucleotides 1 to 1341 of FIG. 12A, B, C, D and E (SEQ ID NO:28) or a DNA sequence which hybridizes under high stringency conditions to an oligonucleotide probe consisting of nucleotides 1 to 1341.

The targeted gene is amplified using standard PCR technology, and the product obtained by amplification then is used to probe, under high stringency conditions, a genomic or cDNA library containing a polynucleotide coding for CCK receptor. High stringency conditions are illustrated by 0.1×SSC (0.015 saline sodium citrate, 0.15M NaCl) at a temperature of 55° C. PCR RACE and Anchored methodologies as described, for example, by Frohman et al., *Proc. Nat'l Acad. Sci USA* 85: 8998–9002 (1988), are suitable for use in this context.

Alternatively, an oligonucleotide probe can be designed for use in screening genomic or cDNA libraries that contain polynucleotides coding for CCK receptor. Thus, one would screen for hybridization using a labeled probe which is a full-length or a partial-length $CCK_A$ or $CCK_B$ receptor coding sequence. An exemplary screening process entails screening first under low stringency conditions, then under high stringency, and selecting those plaques which do not hybridize under the latter conditions. Conditions for low stringency include, for example, 2×SSC at a temperature from 37°–420° C. Once a probe is obtained and a library screened, conventional genetic engineering methodologies may be employed to clone and express the receptor gene in a cell line.

The term "CCK binding affinity" is used in this description, with reference to those molecules that have a high affinity for CCK-8, desulfated CCK-8, CCK-33, CCK-4, desulfated or sulfated gastrin 17-1, gastrin 17-2, pentagastrin or other CCK analogues or CCK family members which are non-sulfated or sulfated. A "high affinity" molecule, in this context is one having a binding affinity constant, $K_d$, for CCK or CCK analogues that is within the range of 10 nanomolar or smaller (picomolar).

Essentially similar approaches can be used, pursuant to the present invention, to identify and clone other CCK receptor genes or $CCK_A$ and $CCK_B$ receptor proteins from different mammalian species, such as human, mouse, rabbit, dog, cat, ferret, goat, pig and monkey. That is, other CCK receptors can be obtained by PCR cloning or library-hybridization screening, or by purification from natural sources. CCK receptor purified to homogeneity from a natural source also can be sequenced. The sequence information in turn is applied to design a probe, as described above, for use in a cloning or hybridization-screening regimen.

Cells which can be transformed with a vector containing receptor DNA of the present invention include eukaryotic cells which can accommodate post-translational processing, such as glycosylation and palmitoylation, and which preferably do not express CCK receptor protein naturally. Illustrative of such eukaryotic cells are Xenopus oocytes, COS-7 and other COS cells, CHO and Swiss 3T3 cells. It is particularly preferred that the host cell possess a "second messenger" pathway, such as a G protein/protein kinase C pathway as found in pancreatic acinar cells, which is relevant to the activity of the CCK receptor in the native cell.

Transformed eukaryotic cell lines are useful for studying the receptor in an environment similar to its native environment, for example, in the context of studying the electrophysiology or binding properties of the receptor. Additionally, a prokaryotic or an insect host cell can be used for expressing CCK receptor, thereby to produce large amounts of receptor for immunological purposes or for studying protein structure, for example, crystallographically.

To confirm that a clone encodes a particular CCK receptor, ligand dose inhibition studies can be performed in cells transfected with the specific receptor cDNA insert. Examples of inhibition studies along these lines are described by Knapp et al., *J. Pharm. Exp. Ther.* 265: 3 (1990), by Grider et al. *Gastrointest. Liver Physiol.* 22: 184–90 (1990), and by Roche et al., *Gastrointest. Liver Physiol.* 23: 182–88 (1991), the respective contents of which are hereby incorporated by reference.

As mentioned previously, the present invention relates to obtaining CCK receptor protein in a form that is sufficiently homogeneous to permit sequencing of the receptor. CCK receptor protein is obtained from smooth muscle cells of the gastrointestinal tract, such as stomach or gall bladder. Other gastrointestinal cells which express CCK receptor include gastric mucosal isolates, containing a mixture of parietal, chief, ECL and D cells. Cells of the central or peripheral nervous system are another source of CCK receptors. In addition to natural tissue, CCK receptor protein can be obtained from cultured cell lines, such as AR42-J, CHP212 and NCI-H209, or from COS-7 cells transfected with either the $CCK_A$ or the $CCK_B$ receptor encoding-DNA (see Example 3).

CCK receptors isolated from such sources can be purified by a regimen which includes the steps of (a) solubilizing a biological preparation containing cholecystokinin receptor in 1% digitonin, (b) applying said solubilized receptor preparation to a cationic exchange resin, and purifying the eluate of said resin (c) applying said purified eluate to a agarose-bound lectin column, preferably a wheat-germ agglutinin agarose column, (d) applying eluate of step (c) to a cibacron blue sepharose column, (e) trace-labeling and subjecting purified receptor to SDS-PAGE gel electrophoresis (reducing conditions) to obtain purified receptor electroeluted from the gel. In connection with this purification process, other affinity columns having similar properties, for example, *Ulex europaeus* agglutinin-I-agarose, can be used.

The amino acid sequence of an isolated CCK receptor purified by the above method can be determined, hence the term "isolated CCK receptor protein", in this context, refers to a CCK receptor protein of sufficient purity to be sequencable via the modified Edman degradation methodology (mixture sequencing and OPA blocking) as described in Example 1. A nucleotide probe can be synthesized which corresponds to the amino acid sequence of the isolated CCK protein or fragments thereof. This nucleotide probe can be used to isolate other CCK proteins in the manner described above.

Isolated CCK receptor proteins or fragments thereof are useful for obtaining antibodies which can recognize CCK-expressing cells. Although the length of a CCK receptor polypeptide or fragment thereof used to stimulate antibody production is not critical, the requirement for immunogenicity may require that the polypeptide be attached to a immunogenicity-imparting carrier, e.g., a particulate carrier like a liposome or a soluble macromolecule (protein or polysaccharide) with a molecular weight in the range of about 10,000 to 1,000,000, or be administered with an adjuvant, such as complete Freund's adjuvant. For artificial polypeptides, as distinguished from CCK fragments, maximum length is determined largely by the limits of techniques readily available for peptide synthesis, that being about fifty amino acids. Thus, a synthetic polypeptide of the present invention is preferably between four and about fifty amino acids in length.

In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes of an animal which has been sensitized with $CCK_A$ or the $CCK_B$ receptor polypeptide, and fusing them with myeloma cells, producing hybridomas. The cloned hybridomas are then screened for production of antibodies the bind preferentially to either the $CCK_A$ or the $CCK_B$ receptor.

"Antibody" also encompasses fragments, like Fab and F(ab')$_2$, of anti-$CCK_A$ or anti-$CCK_B$ antibodies, and conjugates of such fragments, and so-called "antigen binding proteins" (single-chain antibodies) which are based on anti-$CCK_A$ or anti-$CCK_B$ antibodies, in accordance, for example, with U.S. Pat. No. 4,704,692, the contents of which are hereby incorporated by reference. Alternatively, Mabs or a fragment thereof within the present invention can be produced using conventional procedures via the expression of isolated DNA which codes for variable regions of such an Mab in host cells like E. coli, see, e.g., Ward, et al., Nature, 341:544-546 (1989), or transfected murine myeloma cells. See Gillies, et al., Biotechnol. 7: 799-804 (1989); Nakatani, et al., Biotechnol. 7: 805-10 (1989).

Diagnostic applications of these antibodies are exemplified, according to the present invention, by the use of a kit containing an anti-$CCK_A$ or an anti-$CCK_B$ antibody, which undergoes a reaction with a biological sample to determine the extent of $CCK_A$ or $CCK_B$ protein expression. Such a reaction involves the binding of anti-$CCK_A$ antibody to $CCK_A$ antigen or the binding of anti-$CCK_B$ antibody to $CCK_B$ antigen. The observation of an antibody-antigen complex in a biological sample would indicate a positive result. A kit of this sort could be used to detect the extent of expression of CCK receptor in a particular biological sample from an individual, animal, or cell line.

Pursuant to another aspect of the present invention, a CCK receptor-antagonist or agonist can be site-directed to CCK-expressing cells. This is accomplished by conjugating such a compound to a monoclonal antibody, such as an anti-$CCK_A$ or anti-$CCK_B$ antibody. In a preferred embodiment, a CCK inhibitory compound, such as the specific $CCK_A$ receptor-antagonist, L-364,718 or the specific $CCK_B$ receptor-antagonist, L-365,260, is conjugated to an antibody. Conjugation is accomplished by conventional methods for antibody-toxin linkage, such as described by Hertler et al., J. Clin. Oncol. 7(12): 1932 (1989), which is incorporated by reference herein. The antibody conjugates described according to the invention can be used to target CCK-expressing cells, which are present in colon, gastric, and pancreatic tumors, as well as in small cell lung carcinomas.

The present invention is further described with reference to the following, illustrative examples.

EXAMPLE 1

ISOLATION AND CLONING OF $CCK_A$ RECEPTOR

Purification of $CCK_A$ receptors from rat pancreas

Rat pancreatic membranes were prepared from 250 male Sprague-Dawley rat pancreata and solubilized in 2.5 liters of buffer (10 mM HEPES (pH 6.5), 1 mM EGTA, 5 mM $MgCl_2$, 1 $\mu$M dithiothreitol (DTT), 1 $\mu$M leupeptin, 1 $\mu$M pepstatin, 0.5 mM phenylmethylsulfonyl fluoride (PMSF), 140 $\mu$g/ml bacitracin, 200 $\mu$g/ml benzamidine and soybean trypsin inhibitor 0.1 mg/ml at 4° C.) with 1% (weight/volume) digitonin using similar methods, as described by Szecowka et al., Reg. Pep. 10: 71 (1985), and Chang et al., Biochem J. 3: 1709 (1987). Soluble extract was applied to a S-Sepharose (Pharmacia) cationic exchange column (4×15 cm), washed with 600 ml of buffer containing 100 mM NaCl and 0.2% digitonin and eluted with buffer containing 300 mM NaCl and 0.2% digitonin. Receptor purification was followed by a radiolabelled antagonist ([$^3$H]L-364,718) binding assay until final purification by SDS-PAGE. Elution fractions containing [$^3$H]L-364,718 binding activity were pooled, diluted with ⅓ volume of buffer and applied to a wheat-germ agglutinin agarose (Vector Labs) affinity column (1.7 ml packed volume in a Bio-Rad Econo Column), washed overnight with 100 column volumes of buffer containing 150 mM NaCl and 0.1% digitonin and eluted stepwise with 3×1.4 ml volumes of wash buffer plus 16 mM N,N',N"-triacetylchitotriose. The pooled elutions were then applied to a Cibacron Blue Sepharose (Pharmacia) column (0.5 ml packed volume in a Bio-Rad Econo Column), washed and eluted with five 0.5 ml volumes of buffer with 1 mM Cibacron F3GA in a method similar to the above wheat-germ affinity chromatography. Purified receptor was then trace labelled with $^{125}$I by the chloramine T method and subjected to preparative SDS-PAGE (11%) under reducing conditions (50 mM DTT). The major Coomassie brilliant blue stained band corresponding to >90% of the radioactivity was cut, electroeluted, ethanol precipitated and submitted for amino acid analysis and sequencing. Each step of the receptor purification was assayed for protein either by the method of Bradford, Anal. Biochem. 72: 248 (1976), and corrected for the presence of digitonin, or on the basis of amino acid compositional analysis (Beckman analyzer).

Automated protein sequence analysis

Ten micrograms of intact purified rat pancreatic $CCK_A$ receptor was subjected to automated sequence analysis on an Applied Biosystems model 475A gas phase sequencer.

Chemical and enzymatic cleavage of the CCK receptor

Cyanogen bromide (CNBr) cleavage of the CCK receptor was performed on the sequencer filter after five cycles of Edman degradation of the intact receptor using standard methods. The chemically cleaved receptor was then resequenced.

Lysyl Endopeptidase (Wako Chemicals, Osaka, Japan) digestion was performed on 10 $\mu$g of the purified CCK$_A$ receptor in 150 μl of 0.1M Tris HCL, pH 9.0. Enzyme (1:20 relative to the receptor weight) was added at 0 and 2 hours and the reaction was continued for a total of 16 hours at 37° C. and then fractionated by HPLC.

Sequencing of the mixture of peptides was performed on chemical and enzymatic digests to determine the cycle at which proline appeared at the amino terminus. Primary amines of the mixture of peptides were blocked in subsequent sequencing runs where prolines appeared using o-phthalaldehyde (Pierce Chem. Co.) 0.2% (w/v) in n-butyl chloride containing 0.6% (w/v) β-mercaptoethanol delivered through the S1 reservoir instead of R1 (phenylisothiocyanate) at predetermined cycles.

HPLC separation of CCK receptor peptides

CCK receptor products were fractionated on a 2.1 mm×3 cm C$_4$ reverse phase column (Aquapore Bu-300, Brownlee Labs).

Construction of a rat pancreatic cDNA library and isolation of cDNA clones

Messenger RNA was isolated from male, Sprague-Dawley rat pancreas. Oligo dT-primed cDNA of greater than 2 Kb in size was size selected by electrophoresis on an agarose gel. A library was constructed in lambda Zap II (Stratagene) and in vitro packaged according to established methods. Approximately 7.5×10$^5$ plaques were screened with a $^{32}$p labelled, randomly primed probe using a 527 basepair product of the MOPAC PCR described below. Samples on duplicate filters were hybridized at 42° C. overnight, washed once at room temperature for 5 minutes in 300 nM NaCl, 3 mM NaCitrate (2×SSC), 0.1% sodium dodecyl sulfate (SDS) and twice at 45° C. for 20 minutes in 0.1×SSC, and 0.1% SDS, dried and autoradiographed for one to two days. Positive clones were plaque purified and the phagemid pBluescript containing the insert was in vivo excised using the helper phage R408 according to standard protocol (Stratagene).

DNA sequencing

Sequencing of both DNA strands was done by the dideoxy chain-termination method of Sanger with Sequenase version 2 (United States Biochemical).

cDNA cloning using the polymerase chain reaction (PCR)

Mixed oligonucleotides primed amplification of cDNA (MOPAC) was performed using two groups of degenerate primers based on the amino acid sequence from peptides 1 and 3 (FIG. 1B and C SEQ ID NO:13). The sense group of primers, based on peptide 1, was 72 fold degenerate, included two inosines and had the following sequence: (SEQ ID NO:1) 5'-ATGCCIAT/(CG)AAC/TCTIATC/(AT)-CCA/(GCT)AA-3'. The antisense group of primers, based on peptide 3, was 80 fold degenerate and consisted of two groups of 32 and 48 fold degenerate primers with the following sequences respectively: 5'(SEQ ID NO:2)-CCA/GTCA/GCTA/GTCT/CTCA/G-TA-3' and 5'(SEQ ID NO:3)-CCA/GTCA/(TG)GAA/GTCT/CTCA/GTA-3'. One hundred picomoles of each group of primers were used in the PCR reaction. Four percent of the cDNA reversed transcribed from 1 μg of rat pancreatic mRNA was used as a template. The conditions for the PCR were as follows: denaturation for 1 minute at 94° C., annealing for 1.5 minutes at 50° C. and extension for 1 minute at 72° C. The reaction was carried out for 36 cycles. Two percent of the PCR product served as a template for asymmetric PCR using either the sense or antisense group of primers under otherwise same reaction conditions for an additional 25 cycles. The product of the asymmetric PCR was sequenced to confirm its specificity and to provide sequence needed to generate nondegenerate primers for subsequent PCR.

The remaining 3' coding and untranslated sequence was obtained using the methods of rapid amplification of cDNA ends (RACE) and anchored PCR. RACE PCR was performed using 25 pmoles of the gene specific primers, 5'(SEQ ID NO:4)-GCCAGC-CAGAAGAAATCTGCC-3' for the first round and the nested primer (SEQ ID NO:5) 5'-AGCCGAG-CACTGGCAGCAGCA-3' for the second round. The RACE PCR conditions were as follows. First round: denaturation for 7 minutes at 95° C., annealing for 2 minutes at 58° C. and extension for 40 minutes at 72° C. for first cycle; denaturation for 45 seconds at 94° C., annealing for 25 seconds at 58° C., and extension for 3 minutes at 72° C. for 19 cycles and a final similar cycle except extension was for 15 minutes. Second round RACE utilized 2% of the first round product, the nested primer above and the same conditions as the first round except for the omission of the first cycle and a total of 25 cycles. Anchored PCR utilized the unamplified cDNA library constructed in lambda Zap II described above as template DNA, the gene specific primer containing an Xba 1 site and 9 bp cap on the (SEQ ID NO:6) 5' end, 5'-ACTGACTAGTCTAGAT-CAGCTG CCAACCTGATAGCC-3' and the anchored primer from the vector also with an Xba 1 site and 9 pb cap, (SEQ ID NO:7) 5'ACTGACTAGT-CTAGATAATACGACTCACTATAGGGCG-3'. PCR conditions were as follows: denaturation for 3 minutes at 94° C., annealing for 25 seconds at 61° C., extension for 2 minutes at 72° C. for the first cycle, followed by 33 similar cycles except for denaturation for 45 seconds and a final similar cycle except for extension for 15 minutes. The PCR product was digested with Xba 1, subcloned into pGEM (Promega) and sequenced using standard methods.

The CCK$_A$ receptor open reading frame with 5' and partial 3' flanking sequence (nucleotides 5 to 1506 FIG. 1A, B, C, D and E), was cloned using PCR. The sense primer (SEQ ID NO:8) 5'-ACTGACTAGT-CTAGAAATGCTTGCCCAGATGCTCTG-3' (excluding a 5'Xba 1 site and 9 bp cap) was obtained from sequence of a plaque purified clone resulting from cDNA library hybridization screening described above. The antisense primer (SEQ ID NO:9) 5'ACTGAC-TAGTCTAGACAGTGGACCAGGTGGAGTT-CA-31' (excluding the 5'Xba 1 site and 9 bp cap) was obtained from sequence of the product of anchored PCR described above. Single stranded cDNA reversed transcribed from rat pancreatic mRNA served as DNA template. The PCR conditions were the same as those used for anchored PCR described above. The PCR product was digested with Xba 1 and subcloned into the expression vector pcDNA-1 (Invitrogen) and sequenced.

Northern Blot analysis of mRNAs

PolyA+ mRNA was isolated from tissue or cell culture lines, electrophoretically separated on a 1.4% agarose/formaldehyde gel, blotted onto Nytran (Schleicher and Schuell), hybridized with $CCK_A$ receptor cDNA probe labelled with $^{32}P$ by random priming, washed and autoradiographed for 4 days.

In vitro transcription of the CCK receptor and Expression in Xenopus oocytes

DNA was in vitro transcribed using T7 RNA polymerase from a CCK receptor clone template (5 to 1506, FIG. 1A, B, C, D and E, SEQ ID NO:13) in pcDNA-1 (5 μg linearized with Apa 1) in the presence of the cap analog m$^7$G(5')ppp(5')G as recommended by the manufacturer (Promega). Xenopus oocytes were injected with 50 nl of approximately 25 ng of transcribed RNA. At 1-2 days, oocytes were voltage clamped at −70 mV, ligands were applied rapidly and directly to the constantly perfused bath and the ligand dependent Cl$^-$ current measured.

Pharmacological studies clearly demonstrate that the rat pancreas contains CCK receptors which are of the $CCK_A$ subtype. (See, Jensen et al., *Trends Pharmacol. Sci.* 10: 418 (1989). Biochemical studies provide strong evidence on the basis of affinity crosslinking experiments with radiolabelled ligand that the receptors are highly glycosylated and have a molecular weight of 85-95 kDa. With this knowledge, 250 rat pancreases were used to purify the $CCK_A$ receptor to homogeneity. A crude membrane preparation derived from the whole organ was solubilized in 1% digitonin and sequentially purified over three chromatographic columns, cationic exchange resin, wheat-germ agglutinin agarose and Blue sepharose. Starting with 11.7 gms of membrane protein this resulted in an approximately 14,600 fold increase in specific radiolabelled antagonist, [$^3$H]L-364,718, binding activity in 260 μg of purified receptor protein. Radiolabelling of the purified receptor was $^{125}I$ by the chloramine T method followed by SDS-PAGE under denaturing conditions resulted in a single, broad band (suggesting heavy glycosylation) with molecular weight of 85-95 kDA. Purification on preparative SDS-PAGE and electroelution yielded 200 μg of homogeneous receptor for amino acid sequencing.

Initial attempts to obtain sequence on 10 μg of purified intact $CCK_A$ receptor were unsuccessful and indicated that the amino terminus of the receptor was blocked to Edman degradation. Treatment of the intact $CCK_A$ receptor on the filter with CNBr after 5 sequencer cycles resulted in the generation of multiple signals upon resequencing which further suggested that the amino terminus was blocked. One of the signals generated on the first sequencing cycle after CNBr cleavage was a proline. Therefore, a second 10 μg of $CCK_A$ receptor was handled similarly, except that a blocking step using O-phthaldehyde (OPA) was performed at the 1st cycle after CNBr cleavage. A single major signal was generated in the next cycle resulting in the sequence of peptide 1 (FIG. 1, SEQ ID NO:13). This same technique of mixture sequencing and OPA blocking of proline residues was also applied to a lysyl endoproteinase (Lys-C) digest of the intact $CCK_A$ receptor where a proline was observed at cycle 2 of the mixture sequence. This resulted in the sequence of peptide 3 (FIG. 1B and C), SEQ ID NO:13. Further sequence analysis was performed on peptides obtained from Lys-C digestion of intact $CCK_A$ receptor followed by HPLC separation on a C$_4$ column. This resulted in peptides 2, 4, and 5(FIG. 1B C, and D, SEQ ID NO:13).

Based on the sequences of peptides 1, SEQ ID NO:13 and 3 (FIG. 1B and C). two groups of mixed degenerate oligonucleotides were synthesized and MOPAC PCR was used on single stranded cDNA reversed transcribed from rat pancreatic mRNA. This resulted in a 527 bp product (corresponding to sequence 481-1007, FIG. 1B, C and D), SEQ ID NO:13, which, after $^{32}P$ random prime labelling, was used for hybridization screening of an oligo (dT) primed cDNA library constructed from rat pancreas in the vector Lambda Zap II. Twenty-six strongly hybridizing clones were identified on initial screening of approximately $7.5 \times 10^5$ clones. However, after three rounds of plaque purification, only 6 clones remained. The six clones were in vivo excised with R408 helper phage into pBluescript and sequenced. All 6 of these clones contained various mutational deletions of the entire 3' end of the hybridizing sequence. Repeat screening of the library using other bacterial species including phenotypically Rec A and B positive Sure cells (Stratagene) gave similar results. Therefore, only partial sequence corresponding to the 5' untranslated and partial 5' coding region (sequence 1-985, FIG. 1A, B C, and D), SEQ ID NO:13 was obtained.

The remainder of the $CCK_A$ receptor sequence was obtained using PCR cloning methods to circumvent the high rate of mutation during amplification in bacteria. With knowledge of the 5' end of the $CCK_A$ receptor cDNA sequence, gene specific primers were synthesized corresponding to sequences 928-948 and 959-979 (FIG. 1D), SEQ ID NO:13 and used in the first and second rounds, respectively, of the RACE protocol. This resulted in only an additional 366 bp of sequence (sequence 986-1351, FIG. 1D and E), SEQ ID NO:13 because the PCR preferentially amplified truncated products. The remaining 3' sequence was then obtained by the method of "anchored" PCR using a gene specific primer corresponding to sequence 1102-1122 (FIG. 1D). SEQ ID NO:13 and the Lambda Zap II, vector-specific T7 primer/promoter. An additional 155 bp of sequence completed the 3' coding and part of the 3' untranslated sequence to give a total of 1506 bp. The first in frame ATG consistent with a consensus translation initiation site represents the start codon of a single long open reading frame encoding a unique 444 amino acid protein with predicted molecular weight of 49.6 kDa. The five independent peptide sequences obtained from the CNBr cleavage and Lys-C digestion of the purified $CCK_A$ receptor protein are present within the predicted protein sequence (FIG. 1A, B, C, D and E), SEQ ID NO:13 and confirm that the combined DNA sequence derived from cDNA cloning by library hybridization of PCR codes for the purified protein having high affinity for the specific antagonist, L-364,718. The sequence allows for four potential N-linked glycosylation sites, three in the amino terminus and one in the extracellular fourth loop (FIG. 1A, B, C, D and E), SEQ ID NO:13 which is consistent with the heavily glycosylated 85-95 kDa band seen on Coomassie staining and subsequent four step reduction to a final molecular weight of approximately 42 kDa following deglycosylation with Endogylcosidase F (FIG. 1A, B, C, D and E), SEQ ID NO:13. There are four potential sites for protein kinase C phosphorylation, 3 on serine in the large intracellular fifth loop (residues 260, 264 and 275) and one on threonine in the cytoplasmic tail (residue 424) which is consistent with previous data indicating predominately serine, minor threonine and no tyrosine phosphorylation of the $CCK_A$ receptor in rat pancreas following CCK and phorbol 12-myristate 13-acetate stimulation and inhibition of phosphorylation by staurosporine.

A hydropathy plot of the predicted amino acid sequence, using the criteria of Kyte and Doolittle and homology to other G-protein receptor superfamily members, identifies seven regions of hydrophobic residues corresponding to putative transmembrane domains expected for members of the G protein-coupled superfamily of receptors. This is consistent with evidence that G proteins couple $CCK_A$ receptors to phospholipase C in exocrine pancreas. A comparison of the $CCK_A$ receptor deduced protein sequence with all protein sequences in available databanks found that the five most homologous proteins (rat neuromedin K, bovine substance K, mouse gastrin-releasing peptide, rat substance P and rat beta-1 adrenergic receptors) having 27–30% amino acid identity and 50–54% similarity were all members of the G-protein receptor superfamily.

High stringency northern blot analysis of organ- and tissue-specific polyadenylated RNA using a full coding region probe revealed a 2.7 kb hybridizing transcript in rat pancreas and a rat pancreatic acinar carcinoma cell line, AR42J. No hybridization was observed in rat brain or guinea pig gallbladder, organs known to posses CCK receptors, presumably because of low level expression and/or low amount of expressing cell representation in these organs or different receptor subtypes unable to hybridize under the stringent conditions employed. As expected, no signal was observed in liver, muscle or kidney. The size of the hybridizing transcript in consistent with the cloned cDNA size, and the 3 kb size estimated from sucrose gradient fractionation of AR42J mRNA functionally expressed in Xenopus oocytes.

Figure 5A:
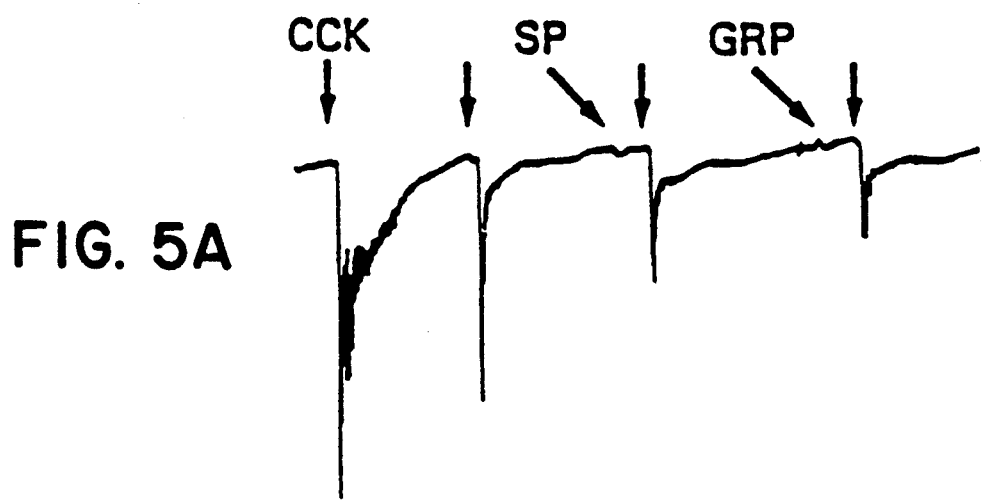
FIG. 5A and B. Expression of the $CCK_A$ receptor in Xenopus oocytes. Ligand induced chloride currents measured in the same oocytes one (A) and two (B) days after injection of mRNA (25 ng) in vitro transcribed from $CCK_A$ receptor cDNA cloned from rat pancreas.
Figure 5B:
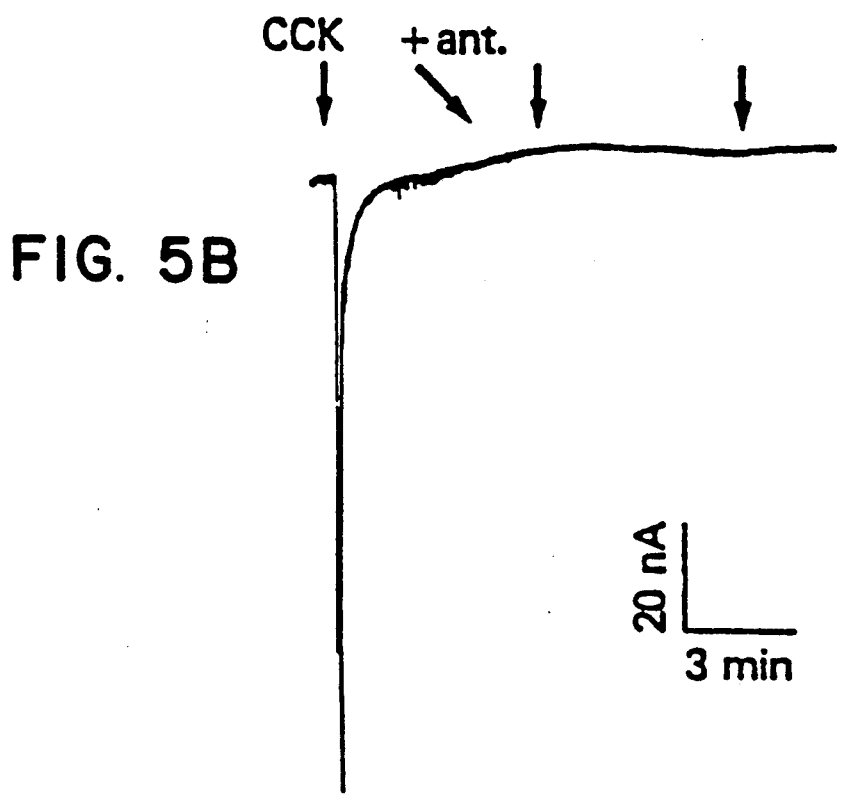

To further demonstrate that the protein sequence encoded by the cDNA represents a functional $CCK_A$ receptor, a capped in vitro transcript of a cDNA clone containing the entire coding region and 5' untranslated sequence (5 to 1506 bp FIG. 1A, B, C, D and E), SEQ ID NO: 13 was injected into Xenopus oocytes and assayed for specific, cell surface, functional expression 1 and 2 days later (FIG. 5A and B). The oocytes responded to CCK octapeptide (CCK-8) (FIG. 5A) but not to gastrin-releasing peptide (GRP), substance P (SP) nor acetylcholine (ACh). Repeated challenges with CCK-8 caused only a moderate desensitization of the response (FIG. 5A) and allowed an internal positive control for the effect of the specific $CCK_A$ receptor antagonist, L-364,718. Application of the specific, $CCK_A$ receptor antagonist, L-364,718, after an initial response to CCK-8 inhibited any further response to repeated applications of CCK-8 (FIG. 5B). Inhibition was specific for $CCK_A$ receptors (i.e., there was no inhibition of SP or ACh response in oocytes injected with their respective receptor mRNAs). Oocytes injected with rat pancreatic total mRNA showed a typical CCK-8 evoked response. Coinjection of the same mRNA with an antisense oligo (reverse complement of nucleotides 265 to 295) completely abolished the response to CCK-8.

EXAMPLE 2

CLONING OF $CCK_B$ RECEPTOR cDNA construction and isolation of cDNA clones

Total RNA was isolated from the rat pancreatic carcinoma cultured cell line, AR42-J and rat brain cortex using a low temperature GITC/GnHCl extraction procedure as described by Han et al., *Biochem.* 26: 1617 (1987), and poly (A)+ RNA was isolated using oligo dT cellulose. Separate cDNA libraries were constructed from each source of poly (A)+ RNA. Oligo dT primed cDNA greater than 2 kilobases was size-selected by agarose gel electrophoresis, electroeluted, adapted with Eco RI, ligated into lambda gt10 arms, and in vitro packaged according to methods described by Davis et al., BASIC METHODS IN MOLECULAR BIOLOGY (1988). Each library ($7.5 \times 10^5$ plaques) was screened with a $^{32}P$ labelled, randomly primed probe corresponding to the coding region of the $CCK_A$ receptor cDNA isolated from rat pancreas initially under conditions of low and later high stringency (three 20-min washes at 42° C. with $2 \times SSC/0.1\%$ SDS for low stringency screening and three 20-min washes at 55° C. with $0.1 \times SSC/0.1\%$ SDS for high stringency washes ($1 \times SSC = 150$ mM NaCl/15 mM sodium citrate, PH 7.0)). Several clones that hybridized at low stringency were plaque-purified from the AR42-J cell library and subcloned into pCDL-SRα at the Xba I site. A $^{32}p$-labelled, randomly primed probe corresponding to the open reading frame of the AR42-J cDNA clones was used to screen another $7.5 \times 10^5$ plaques from the rat brain cortex library under conditions of high stringency. Several purified and subcloned into the vector pCDL-SRα at the Xba I site.

DNA sequencing

Both strands of two cDNA clones isolated from the AR42-J cell library were sequenced by the dideoxy chain termination method of Sanger using Sequenase 2.0 (U.S. Biochemical). One of the cDNA clones isolated from the rat brain cortex library and the product of PCR cloning from the rat brain subcortex cDNA were cycle sequenced (Bethesda Research Labs).

DNA and Protein sequence analysis

Nucleotide and amino acid sequences were analyzed with the Wisconsin Genetics Computer Group software package, by means of the Gap program, as described by Devereux et al., *Nucleic Acids Res.* 12:387 (1984).

Northern blot analysis of mRNAs

Poly (A)+ RNA was isolated using a low temperature GITC/GnHCl extraction, according to the method of Han et al., supra, from rat pancreas, brain cortex and subcortex, striated muscle, liver, kidney, the rat pancreatic acinar carcinoma cell line AR42-J, and guinea pig gallbladder. (Rats do not have gallbladders.) Four micrograms of Poly (A)+ RNA per lane were electrophoretically separated on a 1.4% agarose/formaldehyde gel and blotted onto Nytran (Schleicher and Schuell, Keene, N.H.). The blot was hybridized separately with $CCK_A$ AND $CCK_B$ full length coding region probes, which had been $^{32}P$-labelled (random-primed). The blot was washed under conditions of high stringency (three 20-minute washes at 55% C with $0.1 \times SSC/0.1\%$ SDS) and exposed for 24 hours in a phosphorimager (Molecular Dynamics) to prepare an autoradiograph.

To obtain the rat brain $CCK_B$ receptor cDNA, the $^{32}P$ labelled, randomly primed full length coding region of the $CCK_A$ receptor isolated from rat pancreas was used. Approximately $7.5 \times 10^5$ plaques from two rat brain cDNA libraries constructed from cortex and subcortex were screened under conditions of low and high stringency to isolate clones corresponding to pharmacologically described CCK$_B$ receptors, as described by Saito et al., *Science* 1155 (1980). When this approach did not yield any hybridizing plaques, a cDNA library was constructed from AR42-J cells, a rat pancreatic acinar carcinoma cell line known to express predominantly (80%) CCK$_B$ type CCK receptors. Several candidate clones were isolated only under low stringency conditions, two of which contained a long open reading frame highly homologous to the CCK$_A$ receptor cDNA.

To confirm that the CCK$_B$ receptor isolated from the AR42-J cells was the same CCK$_B$ receptor pharmacologically identified in rat brain (Lambert et al., *Reg. Pept.* 322: 151 (1991), 7.5×10$^5$ plaques were screened from the cortex cDNA library using the new CCK$_B$ open reading frame sequence as a $^{32}$P labelled, randomly-primed probe. Only high stringency hybridizing clones were isolated, one of which was a 2,243 bp clone containing identical cDNA sequence to the two clones isolated from the AR42-J cell cDNA library (FIG. 2A, B, C, D, E and F), SEQ ID NO:15.

A comparison of the nucleotide sequence of the CCK$_B$ receptor cDNA to the CCK$_A$ receptor cDNA sequence (SEQ ID NOS. 15 and 13, respectively reveals a 54% homology, higher than any other sequence reported to date. The first in frame ATG consistent with a consensus translation initiation site initiates a single long open reading frame encoding a unique 452 amino acid protein with predicted molecular weight of 48,954 Da. Similar to the CCK$_A$ receptor, the sequence contains four potential N-linked glycosylation sites, three in the amino terminus and one in the fourth extracellular loop, which would account for the larger than predicted molecular weight of 90 kDa reported in affinity crosslinking studies. There is one potential site for protein kinase C phosphorylation on serine in the first intracellular loop (serine residue #82) and two potential sites for protein kinase A phosphorylation on serine-154 in the second intracellular loop and serine-442 in the cytoplasmic tail and none in the third intracellular loop, unlike the CCK$_A$ receptor.

The predicted amino acid sequences of the CCK$_A$ and CCK$_B$ receptors (SEQ ID NOS. 14 and 16, respectively have a 48% identity which is in the expected range for receptors within the same family and is higher than any other reported protein. A hydropathy plot of the predicted amino acid sequence using criteria of Kyte and Doolittle and homology to the other G-protein receptor superfamily members identifies seven regions of hydrophobic residues corresponding to putative transmembrane domains. Cysteine residues in the first and second extracellular domains are conserved in both receptors as well as other G protein-coupled receptors and may form a disulfide bridge. A cysteine residue in the C-terminal region (residue #377) conserved in most of the G protein coupled receptors may be a membrane anchoring palmitoylation site. An aspartate commonly found in the third transmembrane domain of charged amine ligand binding receptors is absent as expected for these peptide hormone receptors.

Figure 3B:
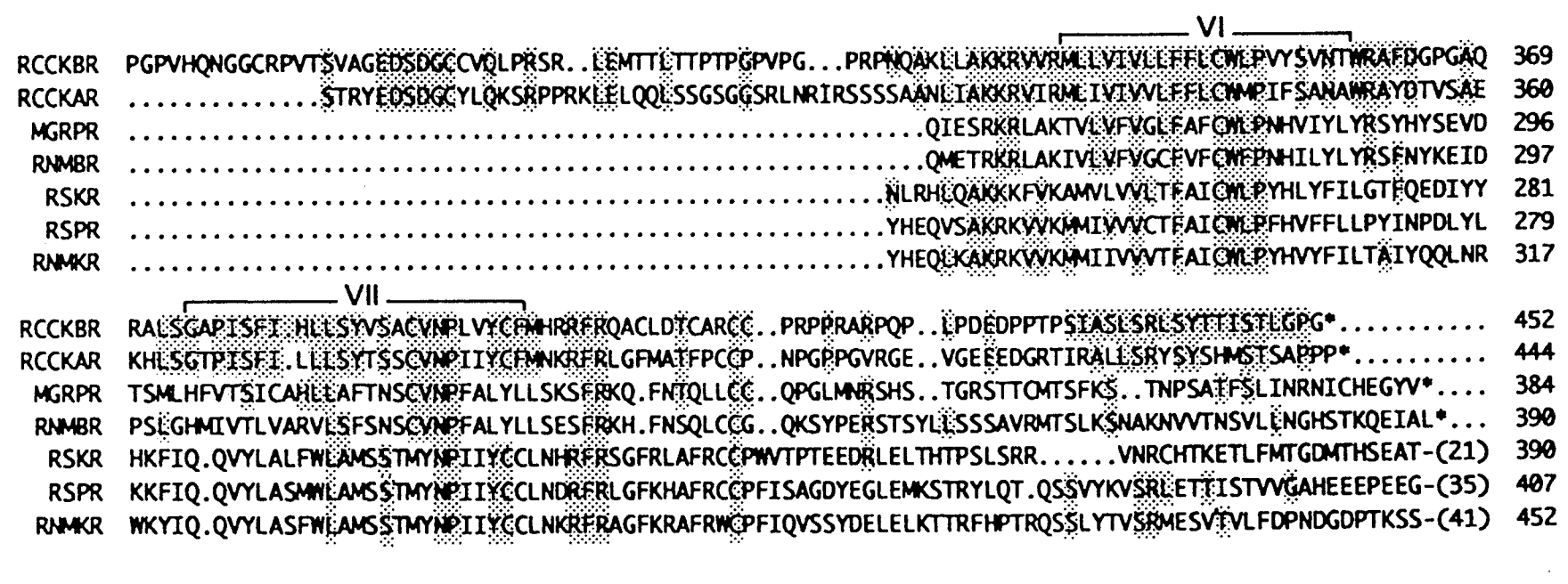

Several other areas of CCK$_A$ and CCK$_B$ amino acid sequence homology also are commonly conserved among other G protein-coupled receptors, indicating their common membership in the G protein-coupled receptor superfamily. The five most similar proteins were mouse gastrin-releasing peptide receptor, rat neuromedin B receptor, rat substance K receptor, rat substance P receptor, and rat neuromedin K receptor, which further supports their suspected membership in the G-protein coupled receptor superfamily (FIG. 3A and B), SEQ ID NOS. 16, 14, 17, 19, 20, 18 and 21). The homology between the two CCK receptor amino acid sequences diverge most notably in the length and composition of their third intracellular loops. This difference may contribute to a difference in G protein coupling specificity since this region has been shown to be important in G protein coupling specificity of other receptors. Cysteines in the first and second extracellular domains are conserved in both receptors and may form a disulfide bridge required for stabilization of a functional tertiary structure as demonstrated for rhodopsin, $\beta$-adrenergic and muscarinic receptors. A cysteine in the C-terminal region conserved in many of the G protein coupled receptors may be a membrane anchoring palmitoylation site as demonstrated for rhodopsin and the $\beta_2$-adrenergic receptors. An aspartate commonly found in the third transmembrane domain of charged amine-binding receptors is absent, as expected in these peptide hormone receptors.

Northern blot analysis reveals that the CCK$_A$ receptor cDNA hybridizes to a single poly A+ RNA of 2.7 Kb from pancreas and AR42-J cells and 4.4 Kb from guinea pig gallbladder, but not to rat brain, striated muscle, liver, and kidney. The absence of Northern blot hybridization to rat brain is not surprising for such a diverse cellular organ with CCK$_A$ receptors localized to only small discreet areas and is consistent with the need to use PCR cloning methods when a large but limited plaque hybridization screening method failed to identify any positive plaques. High stringency Northern blot hybridization to poly A+ RNA from the same tissues using a CCK$_B$ receptor cDNA probe revealed a single hybridizing transcript of 2.4 kB with the expected intensity and distribution in rat brainstem, cortex, and AR42-J cells, and absence of hybridization to rat pancreas, striated muscle, liver, and kidney, tissues and cells expressing either rare or no CCK$_B$ receptors. The size of the hybridizing transcript was in close agreement with the cloned CCK$_B$ receptor cDNA isolated from AR42-J cells.

EXAMPLE 3

EXPRESSION OF CCK$_A$ AND CCK$_B$ RECEPTOR cDNAS IN MAMMALIAN CELLS AND LIGAND INHIBITION STUDIES

Two micrograms of PCDL-SRα containing either the CCK$_A$ coding region insert subcloned at an Xba 1 site in the sense orientation or the CCK$_B$ insert subcloned at an Eco R1 site in the sense orientation were transfected into a near confluent 100 mm tissue culture plate containing approximately 1×10$^6$ COS-7 cells using a DEAE/dextran method. Approximately 48 hours post transfection, the cells were washed twice with phosphate buffered saline (PBS), pH 7.4, 0.1% BSA at 4° C., scraped from the plate in Dulbecco's Modified Eagle's Medium (DMEM), 0.1% BSA, 4° C., centrifuged at 400×G, and resuspended at approximately 3×10$^5$ cells per ml in DMEM, 0.1% BSA, 4° C. Five hundred microliters of resuspended cells were incubated for 60 minutes at 37° C. with 50 pM of the radiolabelled hormone $^{125}$I-Bolton-Hunter- CCK-8 (2200 Ci/mmole) either with or without varying concentrations of unlabelled agonist or antagonist. Cells were subsequently washed three times with 2 ml PBS, 0.1% BSA, 4° C. by filtration on glass filters (Whatman GF/B) using a suction manifold (Millipore). Filters were assayed for gamma radioactivity (Packard, Auto-Gamma).

To confirm that the two receptors cloned from rat brain correspond to the $CCK_A$ and $CCK_B$ receptor subtypes, ligand binding dose inhibition studies were performed. COS-7 cells transfected with the full length cDNA inserts of either $CCK_A$ (FIG. 1A, B, C, D, and E), SEQ ID NO:13 or $CCK_B$ (FIG. 2A, B, D, D, E and F), SEQ ID NO:15 subcloned into the vector, PCDL-SRα (at the Xbal site), were incubated with the radiolabelled ligand, $^{125}$I-BH-CCK-8, alone or in the presence of increasing concentrations of unlabelled CCK receptor agonists or antagonists. Studies with COS-7 cells transfected with the vector containing the $CCK_A$ receptor cDNA insert showed that radiolabelled $^{125}$I-CCK-8 binding inhibition by CCK-8 was about 1000-10,000 fold, or preferably about 3000 fold more potent than gastrin-17-I, and that the $CCK_A$ receptor specific antagonist, L-364,718 was about equally potent to CCK-8, and about 30-100 fold more potent than the $CCK_B$ receptor specific antagonist, L-365,260.

Studies with COS-7 cells transfected with the vector containing the $CCK_B$ receptor cDNA insert showed that CCK-8 was only about 3-10 fold more potent than Gastrin-17-I, and that the $CCK_B$ receptor specific antagonist, L-365,260 was about 10-100 fold more potent than the $CCK_A$ receptor specific antagonist, L-364,718 at inhibiting $^{121}$I-BH-CCK-8 binding. These results agree closely with previous pharmacological binding studies of $CCK_A$ and $CCK_B$ receptors from rat brain and support the classification of these cloned receptors from rat brain as $CCK_A$ and $CCK_B$ subtypes.

It was demonstrated that DNA molecules encoding CCK receptor proteins can be obtained by employing nucleotide sequences encoding $CCK_A$ and $CCK_B$ receptor proteins as identified by the present invention as probes to isolate from other species such nucleotide molecules encoding CCK receptor protein. Using the methods described above, DNA molecules encoding guinea pig $CCK_A$ and $CCK_B$ receptor proteins were isolated, whose sequences are provided in FIGS. 6A, B, C, D, E and F (SEQ ID NOS. 22 and 23) and 9A, B, C, D, E and F (SEQ ID NOS. 25 and 26) respectively.

EXAMPLE 4

CONSTRUCTION OF A GUINEA PIG GALLBLADDER cDNA LIBRARY AND ISOLATION OF $CCK_A$ AND $CCK_B$ RECEPTOR cDNA CLONES

Male Hartley guinea pigs (150-175 g) were obtained from the Small animal section, Veterinary Resources Branch, National Institutes of Health, Bethesda, Md. Guinea pig pancreases and gallbladders were immediately snap frozen in liquid nitrogen. Total RNA was extracted using a low temperature guanidine isothiocyanate/guanidine hydrochloride method (Han et al., supra). Poly (A)+ RNA was isolated using oligo dT cellulose. Oligo dT primed cDNA>2 kb was size selected by agarose gel electrophoresis, electroeluted, adapted with Eco Rl, ligated into lambda gt 10 arms and in vitro packaged using established methods. Approximately $8 \times 10^5$ plaques were screened under high stringency conditions with a $^{32}$P-labelled, randomly primed probe generated from the rat $CCK_A$ or the rat $CCK_B$ receptor coding regions to obtain the guinea pig $CCK_A$ or $CCK_B$ receptors, respectively. Duplicate filters were washed once at room temperature for 5 minutes in 2× standard saline citrate (SSC; 2×SSC=300 mM NaCl/3 mM sodium citrate and 0.1% SDS) and three times at 55° C. for 20 minutes in 0.1×SSC and 0.1% SDS, dried and autoradiographed for 2 days using. Positive hybridizing clones were plaque purified using established methods.

EXAMPLE 5

ISOLATION OF HUMAN $CCK_B$ RECEPTOR cDNA

The nucleotide and deduced amino acid sequences of the human $CCK_B$ receptor cDNA (FIG. 12A, B, C, D and E) SEQ ID NOS. 28 and 29 found to be identical for both brain and stomach, were obtained according to the following method. A human temporal cortex oligo d(T)/random-primed cDNA library, in λ-phage vector, DR 2 (Clontech, Palo Alto, Calif.; catalogue #HL1143), was screened under low stringency conditions (three 30-minute washes in 2×SSC (0.015 saline sodium citrate, 0.15M NaCl), 0.1% SDS (sodium dodecyl sulfate) at 37° C.) with a $^{32}$p-labelled, random-primed probe derived from the rat $CCK_B$ receptor cDNA. The longest clone, Hu-B-10, provided the sequence of nucleotides 281-1969.

The initial portion of the sequence, nucleotides 1-280, was obtained by the polymerase chain reaction using the degenerate sense primer, (SEQ ID NO:10) 5'-GGAG/CC/TTCA/GG/CA/TGGA/GGCCATG-GA-3'. This degenerate primer was derived from the rat and guinea pig $CCK_B$ receptor cDNA sequences. The antisense primer used, (SEQ ID NO:11), 5'-GGGCCAGCGATGCACGCACTG-3', was obtained from the Hu-B-10 cDNA sequence described above. The target DNA for PCR was human stomach cDNA prepared from oligo d(T)-primed mRNA, according to the method described by Wank et al., PNAS USA 89: 3125 (1992).

Figure 4B:
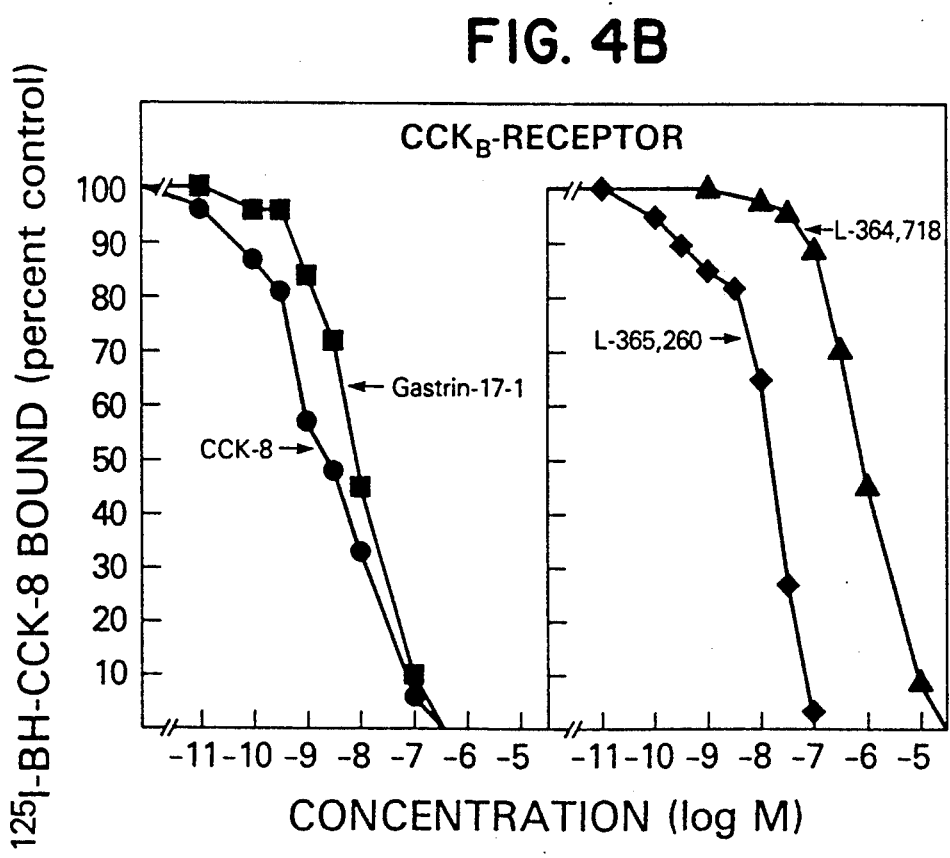

A full-length cDNA coding region sequence and partial 3' untranslated sequence of the human $CCK_B$ receptor was obtained as a single PCR product using the above degenerate sense primer (SEQ ID NO:10) (5'-GGAG/CC/TTCA/GG/CA/TGGA/GG-CCATGGA-3') plus an additional 5'-15-basepair sequence and a different antisense primer, 5'-ACTGAC-TAGTCTAGAGCTTTGGGTGTTGGTTTCCTG-3' (containing a 5' cap sequence and a Xbal restriction sequence). The 5'-15-basepair sequence was comprised of a cap sequence followed by an Xbal restriction sequence. The full-length sequence and partial 3' untranslated sequence was made from these primers, digested with Xbal endonuclease, and subcloned into PCDL-SRα vector and subcloned into COS-7 cells. The pharmacology exhibited by the expressed $hCCK_B$ protein was similar to that of guinea pig and rat $CCK_B$ receptors, as discussed above (see FIG. 4B, bottom panel and FIG. 11).

The CCK family of peptides interact with at least two receptor subtypes widely distributed throughout the gastrointestinal and nervous systems with some cells possessing both subtypes. The present results should allow better assignment of CCK receptor subtype distribution and function on the basis of such studies as in situ hybridization, cloning of other subtypes using low stringency hybridization methods, production of large quantities of pure receptor for immunization and screening of new more potent and selective agonists and antagonists. This should ultimately allow targeting of therapy to diseased organs of the gastrointestinal and nervous systems while sparing uninvolved organs which possess different CCK subtypes.

As will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the foregoing examples.

---

What is claimed is:

1. A method for purifying a cholecystokinin receptor comprising the steps of
   (a) solubilizing a biological preparation containing cholecystokinin receptor in 1% digitonin,
   (b) applying said solubilized receptor preparation to a cationic exchange resin, and purifying the eluate of said resin,
   (c) applying said purified eluate to an agarose-bound lectin, and eluting the receptor containing fraction from the agarose bound lectin, and
   (d) applying an eluate of step (c) to a cibacron blue sepharose column, and eluting the receptor containing fraction.

2. A method according to claim 1, wherein said lectin is a wheat-germ agglutinin.

3. A method according to claim 1, further comprising the step (e) of trace-labeling and subjecting the cholecystokinin receptor from step (d) to SDS-PAGE gel electrophoresis under reducing conditions to obtain purified receptor.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i x ) FEATURE:
        ( A ) NAME/KEY: miscdifference
        ( B ) LOCATION: replace(6, "")
        ( D ) OTHER INFORMATION: /note="N at position 6 represents Inosine"

( i x ) FEATURE:
        ( A ) NAME/KEY: miscdifference
        ( B ) LOCATION: replace(14, "")
        ( D ) OTHER INFORMATION: /note="N at position 14 represents Inosine"

( x i ) SEQUENCE DESCRIPTION: SEQ ID NO:1:

ATGCCNABAA YCTNATHCCN AA                    22

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:2:

CCRTCRCTRT CYTCRTA                        17

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:3:

CCRTCDGART CYTCRTA                        17

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCCAGCCAGA AGAAATCTGC C                    21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:5:

AGCCGAGCAC TGGCAGCAGC A                            21

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:6:

ACTGACTAGT CTAGATCAGC TGCCAACCTG ATAGCC          36

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (x i) SEQUENCE DESCRIPTION: SEQ ID NO:7:

ACTGACTAGT CTAGATAATA CGACTCACTA TAGGGCG          37

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:8:

ACTGACTAGT CTAGAAATGC TTGCCCAGAT GCTCTG          36

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i v) ANTI-SENSE: YES (x i) SEQUENCE DESCRIPTION: SEQ ID NO:9:

ACTGACTAGT CTAGACAGTG GACCAGGTGG AGTTCA          36

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:10:

GGASYTCRSW GGRGCCATGG A                            21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:11:

```
GGGCCAGCGA TGCACGCACT G                                              21
```

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:12:

```
ACTGACTAGT CTAGAGCTTT GGGTGTTGGT TTCCTG                              36
```

( 2 ) INFORMATION FOR SEQ ID NO:13:

( i ) SEQUENCE CHARACTERISTICS:
        ( A ) LENGTH: 1506 base pairs
        ( B ) TYPE: nucleic acid
        ( C ) STRANDEDNESS: double
        ( D ) TOPOLOGY: linear ( i i ) MOLECULE TYPE: cDNA ( v i i ) IMMEDIATE SOURCE:
        ( B ) CLONE: rat pancreatic CCKA receptor ( i x ) FEATURE:
        ( A ) NAME/KEY: CDS
        ( B ) LOCATION: 154..1488

( x i ) SEQUENCE DESCRIPTION: SEQ ID NO:13:

```
CCGCAATGCT TGCCCAGATG CTCTGAGAAT GGCGAACTCA AGTTGCCTTT AGGAATGGCT    60

GCAAAGCCCA CACCTGGAAA TCTCCCCCTC CCTGCTCCTC CACGGCAGGT TGCATTTGGG   120

AGACCCTGTG ATCATTAGAG GAGAGAGACA GGA ATG AGC CAT TCA CCA GCT CGC   174
                                    Met Ser His Ser Pro Ala Arg
                                      1               5

CAG CAC TTG GTA GAA AGC AGC AGG ATG GAC GTG GTC GAC AGC CTT CTT    222
Gln His Leu Val Glu Ser Ser Arg Met Asp Val Val Asp Ser Leu Leu
         10                  15                  20

ATG AAT GGG AGC AAC ATC ACT CCC CCC TGT GAA CTC GGA CTG GAA AAT    270
Met Asn Gly Ser Asn Ile Thr Pro Pro Cys Glu Leu Gly Leu Glu Asn
     25                  30                  35

GAG ACG CTT TTC TGC TTG GAT CAA CCT CAA CCT TCA AAA GAG TGG CAG    318
Glu Thr Leu Phe Cys Leu Asp Gln Pro Gln Pro Ser Lys Glu Trp Gln
 40                  45                  50                  55

TCT GCA CTG CAG ATT CTC CTG TAC TCC ATC ATA TTC CTT CTC AGT GTG    366
Ser Ala Leu Gln Ile Leu Leu Tyr Ser Ile Ile Phe Leu Leu Ser Val
             60                  65                  70

CTG GGG AAC ACG CTG GTT ATA ACG GTG CTG ATT CGA AAC AAG AGG ATG    414
Leu Gly Asn Thr Leu Val Ile Thr Val Leu Ile Arg Asn Lys Arg Met
         75                  80                  85

CGG ACG GTC ACC AAC ATC TTC CTG CTG TCC CTG GCT GTC AGT GAC CTC    462
Arg Thr Val Thr Asn Ile Phe Leu Leu Ser Leu Ala Val Ser Asp Leu
         90                  95                 100
```

-continued

| | | | | | | | | | | | | | | | | |
|---|---|---|---|---|---|---|---|---|---|---|---|---|---|---|---|---|
| ATG | CTC | TGC | CTC | TTC | TGC | ATG | CCG | TTC | AAC | CTC | ATC | CCC | AAC | CTG | CTC | 510 |
| Met | Leu | Cys | Leu | Phe | Cys | Met | Pro | Phe | Asn | Leu | Ile | Pro | Asn | Leu | Leu | |
| | 105 | | | | 110 | | | | | 115 | | | | | | |
| AAG | GAT | TTC | ATC | TTC | GGA | AGT | GCC | GTG | TGC | AAG | ACT | ACC | ACC | TAC | TTC | 558 |
| Lys | Asp | Phe | Ile | Phe | Gly | Ser | Ala | Val | Cys | Lys | Thr | Thr | Thr | Tyr | Phe | |
| 120 | | | | | 125 | | | | | 130 | | | | | 135 | |
| ATG | GGC | ACT | TCC | GTG | AGC | GTT | TCC | ACC | TTC | AAC | CTG | GTA | GCC | ATC | TCT | 606 |
| Met | Gly | Thr | Ser | Val | Ser | Val | Ser | Thr | Phe | Asn | Leu | Val | Ala | Ile | Ser | |
| | | | | 140 | | | | | 145 | | | | | 150 | | |
| CTG | GAG | AGA | TAT | GGC | GCC | ATC | TGC | AGA | CCC | CTA | CAG | TCC | CGC | GTC | TGG | 654 |
| Leu | Glu | Arg | Tyr | Gly | Ala | Ile | Cys | Arg | Pro | Leu | Gln | Ser | Arg | Val | Trp | |
| | | | 155 | | | | 160 | | | | | 165 | | | | |
| CAA | ACA | AAG | TCC | CAT | GCT | TTG | AAG | GTC | ATC | GCT | GCC | ACC | TGG | TGC | CTC | 702 |
| Gln | Thr | Lys | Ser | His | Ala | Leu | Lys | Val | Ile | Ala | Ala | Thr | Trp | Cys | Leu | |
| | | 170 | | | | | 175 | | | | | 180 | | | | |
| TCC | TTT | ACC | ATC | ATG | ACT | CCG | TAC | CCC | ATT | TAC | AGC | AAC | TTG | GTG | CCT | 750 |
| Ser | Phe | Thr | Ile | Met | Thr | Pro | Tyr | Pro | Ile | Tyr | Ser | Asn | Leu | Val | Pro | |
| | 185 | | | | 190 | | | | | 195 | | | | | | |
| TTT | ACT | AAA | AAT | AAT | AAC | CAG | ACG | GCG | AAC | ATG | TGC | CGC | TTC | CTG | TTG | 798 |
| Phe | Thr | Lys | Asn | Asn | Asn | Gln | Thr | Ala | Asn | Met | Cys | Arg | Phe | Leu | Leu | |
| 200 | | | | | 205 | | | | | 210 | | | | | 215 | |
| CCA | AGT | GAC | GCT | ATG | CAG | CAG | TCC | TGG | CAA | ACA | TTC | CTG | CTA | CTC | ATC | 846 |
| Pro | Ser | Asp | Ala | Met | Gln | Gln | Ser | Trp | Gln | Thr | Phe | Leu | Leu | Leu | Ile | |
| | | | | 220 | | | | | 225 | | | | | 230 | | |
| CTC | TTT | CTT | CTC | CCT | GGG | ATT | GTG | ATG | GTG | GTG | GCC | TAC | GGG | TTG | ATC | 894 |
| Leu | Phe | Leu | Leu | Pro | Gly | Ile | Val | Met | Val | Val | Ala | Tyr | Gly | Leu | Ile | |
| | | | 235 | | | | | 240 | | | | | 245 | | | |
| TCT | CTG | GAA | CTC | TAC | CAA | GGA | ATC | AAA | TTT | GAT | GCC | AGC | CAG | AAG | AAA | 942 |
| Ser | Leu | Glu | Leu | Tyr | Gln | Gly | Ile | Lys | Phe | Asp | Ala | Ser | Gln | Lys | Lys | |
| | | 250 | | | | | 255 | | | | | 260 | | | | |
| TCT | GCC | AAA | GAG | AAG | AAG | CCG | AGC | ACT | GGC | AGC | AGC | ACC | CGA | TAT | GAG | 990 |
| Ser | Ala | Lys | Glu | Lys | Lys | Pro | Ser | Thr | Gly | Ser | Ser | Thr | Arg | Tyr | Glu | |
| | 265 | | | | 270 | | | | | 275 | | | | | | |
| GAT | AGT | GAT | GGC | TGT | TAC | TTG | CAG | AAG | TCC | CGG | CCC | CCG | AGG | AAG | CTG | 1038 |
| Asp | Ser | Asp | Gly | Cys | Tyr | Leu | Gln | Lys | Ser | Arg | Pro | Pro | Arg | Lys | Leu | |
| 280 | | | | | 285 | | | | | 290 | | | | | 295 | |
| GAG | CTT | CAG | CAG | CTG | TCT | AGC | GGC | AGC | GGT | GGC | AGC | AGA | CTC | AAC | CGG | 1086 |
| Glu | Leu | Gln | Gln | Leu | Ser | Ser | Gly | Ser | Gly | Gly | Ser | Arg | Leu | Asn | Arg | |
| | | | | 300 | | | | | 305 | | | | | 310 | | |
| ATC | AGG | AGC | AGC | AGT | TCA | GCT | GCC | AAC | CTG | ATA | GCC | AAG | AAG | CGC | GTG | 1134 |
| Ile | Arg | Ser | Ser | Ser | Ser | Ala | Ala | Asn | Leu | Ile | Ala | Lys | Lys | Arg | Val | |
| | | | 315 | | | | | 320 | | | | | 325 | | | |
| ATC | CGC | ATG | CTC | ATT | GTC | ATC | GTG | GTC | CTC | TTC | TTC | CTG | TGC | TGG | ATG | 1182 |
| Ile | Arg | Met | Leu | Ile | Val | Ile | Val | Val | Leu | Phe | Phe | Leu | Cys | Trp | Met | |
| | | 330 | | | | | 335 | | | | | 340 | | | | |
| CCC | ATC | TTC | AGC | GCC | AAC | GCC | TGG | CGG | GCA | TAT | GAC | ACG | GTT | TCT | GCC | 1230 |
| Pro | Ile | Phe | Ser | Ala | Asn | Ala | Trp | Arg | Ala | Tyr | Asp | Thr | Val | Ser | Ala | |
| | 345 | | | | 350 | | | | | 355 | | | | | | |
| GAG | AAG | CAC | CTC | TCA | GGG | ACT | CCC | ATC | TCC | TTC | ATC | CTC | CTC | CTC | TCC | 1278 |
| Glu | Lys | His | Leu | Ser | Gly | Thr | Pro | Ile | Ser | Phe | Ile | Leu | Leu | Leu | Ser | |
| 360 | | | | | 365 | | | | | 370 | | | | | 375 | |
| TAC | ACC | TCC | TCC | TGT | GTT | AAC | CCC | ATC | ATC | TAT | TGC | TTC | ATG | AAC | AAA | 1326 |
| Tyr | Thr | Ser | Ser | Cys | Val | Asn | Pro | Ile | Ile | Tyr | Cys | Phe | Met | Asn | Lys | |
| | | | | 380 | | | | | 385 | | | | | 390 | | |
| CGC | TTT | CGC | CTG | GGC | TTC | ATG | GCC | ACC | TTC | CCT | TGT | TGC | CCG | AAT | CCC | 1374 |
| Arg | Phe | Arg | Leu | Gly | Phe | Met | Ala | Thr | Phe | Pro | Cys | Cys | Pro | Asn | Pro | |
| | | | 395 | | | | | 400 | | | | | 405 | | | |
| GGT | CCC | CCA | GGG | GTG | AGA | GGA | GAG | GTG | GGA | GAG | GAG | GAG | GAT | GGG | AGG | 1422 |
| Gly | Pro | Pro | Gly | Val | Arg | Gly | Glu | Val | Gly | Glu | Glu | Glu | Asp | Gly | Arg | |
| | | 410 | | | | | 415 | | | | | 420 | | | | |
| ACC | ATA | AGG | GCA | TTG | CTG | TCC | AGG | TAT | TCC | TAC | AGC | CAC | ATG | AGC | ACC | 1470 |
| Thr | Ile | Arg | Ala | Leu | Leu | Ser | Arg | Tyr | Ser | Tyr | Ser | His | Met | Ser | Thr | |

```
                    425                    430                  435
TCT  GCT  CCA  CCC  CCC  TGAACTCCAC  CTGGTCCACT  G                            1506
Ser  Ala  Pro  Pro  Pro
440                      445
```

( 2 ) INFORMATION FOR SEQ ID NO:14:

( i ) SEQUENCE CHARACTERISTICS:
( A ) LENGTH: 444 amino acids
( B ) TYPE: amino acid
( D ) TOPOLOGY: linear ( i i ) MOLECULE TYPE: protein ( x i ) SEQUENCE DESCRIPTION: SEQ ID NO:14:

```
Met  Ser  His  Ser  Pro  Ala  Arg  Gln  His  Leu  Val  Glu  Ser  Ser  Arg  Met
 1              5                        10                       15

Asp  Val  Val  Asp  Ser  Leu  Leu  Met  Asn  Gly  Ser  Asn  Ile  Thr  Pro  Pro
              20                       25                       30

Cys  Glu  Leu  Gly  Leu  Glu  Asn  Glu  Thr  Leu  Phe  Cys  Leu  Asp  Gln  Pro
              35                       40                       45

Gln  Pro  Ser  Lys  Glu  Trp  Gln  Ser  Ala  Leu  Gln  Ile  Leu  Leu  Tyr  Ser
         50                       55                       60

Ile  Ile  Phe  Leu  Leu  Ser  Val  Leu  Gly  Asn  Thr  Leu  Val  Ile  Thr  Val
 65                       70                       75                       80

Leu  Ile  Arg  Asn  Lys  Arg  Met  Arg  Thr  Val  Thr  Asn  Ile  Phe  Leu  Leu
                   85                       90                       95

Ser  Leu  Ala  Val  Ser  Asp  Leu  Met  Leu  Cys  Leu  Phe  Cys  Met  Pro  Phe
                 100                      105                      110

Asn  Leu  Ile  Pro  Asn  Leu  Leu  Lys  Asp  Phe  Ile  Phe  Gly  Ser  Ala  Val
              115                      120                      125

Cys  Lys  Thr  Thr  Thr  Tyr  Phe  Met  Gly  Thr  Ser  Val  Ser  Val  Ser  Thr
         130                      135                      140

Phe  Asn  Leu  Val  Ala  Ile  Ser  Leu  Glu  Arg  Tyr  Gly  Ala  Ile  Cys  Arg
145                      150                      155                      160

Pro  Leu  Gln  Ser  Arg  Val  Trp  Gln  Thr  Lys  Ser  His  Ala  Leu  Lys  Val
                 165                      170                      175

Ile  Ala  Ala  Thr  Trp  Cys  Leu  Ser  Phe  Thr  Ile  Met  Thr  Pro  Tyr  Pro
              180                      185                      190

Ile  Tyr  Ser  Asn  Leu  Val  Pro  Phe  Thr  Lys  Asn  Asn  Asn  Gln  Thr  Ala
         195                      200                      205

Asn  Met  Cys  Arg  Phe  Leu  Leu  Pro  Ser  Asp  Ala  Met  Gln  Gln  Ser  Trp
210                      215                      220

Gln  Thr  Phe  Leu  Leu  Leu  Ile  Leu  Phe  Leu  Leu  Pro  Gly  Ile  Val  Met
225                      230                      235                      240

Val  Val  Ala  Tyr  Gly  Leu  Ile  Ser  Leu  Glu  Leu  Tyr  Gln  Gly  Ile  Lys
              245                      250                      255

Phe  Asp  Ala  Ser  Gln  Lys  Lys  Ser  Ala  Lys  Glu  Lys  Lys  Pro  Ser  Thr
              260                      265                      270

Gly  Ser  Ser  Thr  Arg  Tyr  Glu  Asp  Ser  Asp  Gly  Cys  Tyr  Leu  Gln  Lys
              275                      280                      285

Ser  Arg  Pro  Pro  Arg  Lys  Leu  Glu  Leu  Gln  Gln  Leu  Ser  Ser  Gly  Ser
         290                      295                      300

Gly  Gly  Ser  Arg  Leu  Asn  Arg  Ile  Arg  Ser  Ser  Ser  Ser  Ala  Ala  Asn
305                      310                      315                      320

Leu  Ile  Ala  Lys  Lys  Arg  Val  Ile  Arg  Met  Leu  Ile  Val  Ile  Val  Val
                 325                      330                      335

Leu  Phe  Phe  Leu  Cys  Trp  Met  Pro  Ile  Phe  Ser  Ala  Asn  Ala  Trp  Arg
```

|   |   |   |   |   |   | 340 |   |   |   |   | 345 |   |   |   |   | 350 |   |   |
|---|---|---|---|---|---|---|---|---|---|---|---|---|---|---|---|---|---|---|
| Ala | Tyr | Asp<br>355 | Thr | Val | Ser | Ala | Glu<br>360 | Lys | His | Leu | Ser | Gly<br>365 | Thr | Pro | Ile |
| Ser | Phe<br>370 | Ile | Leu | Leu | Leu | Ser<br>375 | Tyr | Thr | Ser | Ser | Cys<br>380 | Val | Asn | Pro | Ile |
| Ile<br>385 | Tyr | Cys | Phe | Met | Asn<br>390 | Lys | Arg | Phe | Arg | Leu<br>395 | Gly | Phe | Met | Ala | Thr<br>400 |
| Phe | Pro | Cys | Cys | Pro<br>405 | Asn | Pro | Gly | Pro | Pro<br>410 | Gly | Val | Arg | Gly | Glu<br>415 | Val |
| Gly | Glu | Glu | Glu<br>420 | Asp | Gly | Arg | Thr | Ile<br>425 | Arg | Ala | Leu | Leu | Ser<br>430 | Arg | Tyr |
| Ser | Tyr | Ser<br>435 | His | Met | Ser | Thr | Ser<br>440 | Ala | Pro | Pro | Pro |

( 2 ) INFORMATION FOR SEQ ID NO:15:

( i ) SEQUENCE CHARACTERISTICS:
        ( A ) LENGTH: 2243 base pairs
        ( B ) TYPE: nucleic acid
        ( C ) STRANDEDNESS: double
        ( D ) TOPOLOGY: linear ( i i ) MOLECULE TYPE: cDNA ( v i i ) IMMEDIATE SOURCE:
        ( B ) CLONE: rat brain CCKB receptor ( i x ) FEATURE:
        ( A ) NAME/KEY: CDS
        ( B ) LOCATION: 136..1494

( x i ) SEQUENCE DESCRIPTION: SEQ ID NO:15:

TGACCCTGCT TGCTCAACTC TACGTCTTGT TTCGTTTTCT GTTCTGCGCC GTTACAGATC    60

CAAGCTCCTC GAGCCCGGGC TGCAGGAATT CTGCGGCCGC CGCTTAGCAG AGCTAAGTGG    120

GACTTCACTG GAGCC ATG GAG CTG CTC AAG CTG AAC CGC AGC GTG CAG GGA    171

Met Glu Leu Leu Lys Leu Asn Arg Ser Val Gln Gly
                 1             5                    10

CCA GGA CCC GGG TCG GGG TCT TCT TTG TGC CGC CCG GGT GTC TCC CTT    219
Pro Gly Pro Gly Ser Gly Ser Ser Leu Cys Arg Pro Gly Val Ser Leu
       15                 20                25

CTC AAC AGC AGT AGT GCC GGG AAC CTC AGC TGT GAC CCC CCT CGT ATC    267
Leu Asn Ser Ser Ser Ala Gly Asn Leu Ser Cys Asp Pro Pro Arg Ile
    30                   35                   40

CGC GGA ACC GGG ACC AGA GAA TTG GAG ATG GCG ATT AGA ATC ACC CTT    315
Arg Gly Thr Gly Thr Arg Glu Leu Glu Met Ala Ile Arg Ile Thr Leu
45                    50                55                  60

TAT GCA GTG ATC TTT CTG ATG AGT GTT GGC GGA AAC GTG CTC ATC ATC    363
Tyr Ala Val Ile Phe Leu Met Ser Val Gly Gly Asn Val Leu Ile Ile
            65                   70                    75

GTG GTC CTG GGA CTG AGC CGA CGC CTA AGA ACG GTC ACC AAC GCC TTC    411
Val Val Leu Gly Leu Ser Arg Arg Leu Arg Thr Val Thr Asn Ala Phe
              80                    85                    90

CTG CTC TCC CTG GCA GTC AGC GAC CTC CTG CTG GCC GTG GCT TGC ATG    459
Leu Leu Ser Leu Ala Val Ser Asp Leu Leu Leu Ala Val Ala Cys Met
           95                    100                105

CCC TTC ACA CTC CTG CCC AAC CTC ATG GGC ACA TTC ATC TTC GGC ACA    507
Pro Phe Thr Leu Leu Pro Asn Leu Met Gly Thr Phe Ile Phe Gly Thr
    110                     115                   120

GTC ATC TGC AAG GCC ATT TCC TAC CTC ATG GGG GTA TCA GTG AGT GTA    555
Val Ile Cys Lys Ala Ile Ser Tyr Leu Met Gly Val Ser Val Ser Val
125                    130                135                140

TCC ACT CTA AAT CTC GTG GCC ATA GCC CTG GAG CGA TAC AGC GCC ATC    603

|     |     |     |     |     |     |     |     |     |     |     |     |     |     |     |     |
|-----|-----|-----|-----|-----|-----|-----|-----|-----|-----|-----|-----|-----|-----|-----|-----|
| Ser | Thr | Leu | Asn | Leu | Val | Ala | Ile | Ala | Leu | Glu | Arg | Tyr | Ser | Ala | Ile |
|     |     |     |     | 145 |     |     |     |     | 150 |     |     |     |     | 155 |     |

| TGC | CGA | CCA | CTG | CAA | GCA | CGA | GTA | TGG | CAA | ACA | CGC | TCC | CAC | GCA | GCT | 651 |
|-----|-----|-----|-----|-----|-----|-----|-----|-----|-----|-----|-----|-----|-----|-----|-----|-----|
| Cys | Arg | Pro | Leu | Gln | Ala | Arg | Val | Trp | Gln | Thr | Arg | Ser | His | Ala | Ala |     |
|     |     |     | 160 |     |     |     |     | 165 |     |     |     |     | 170 |     |     |     |

| CGG | GTG | ATC | TTA | GCC | ACG | TGG | CTG | CTG | TCT | GGA | CTG | CTT | ATG | GTA | CCC | 699 |
| Arg | Val | Ile | Leu | Ala | Thr | Trp | Leu | Leu | Ser | Gly | Leu | Leu | Met | Val | Pro |     |
|     |     | 175 |     |     |     |     | 180 |     |     |     |     | 185 |     |     |     |     |

| TAC | CCT | GTG | TAC | ACC | ATG | GTA | CAG | CCA | GTG | GGA | CCT | CGA | GTG | CTG | CAG | 747 |
| Tyr | Pro | Val | Tyr | Thr | Met | Val | Gln | Pro | Val | Gly | Pro | Arg | Val | Leu | Gln |     |
|     | 190 |     |     |     |     | 195 |     |     |     |     | 200 |     |     |     |     |     |

| TGC | ATG | CAT | CGC | TGG | CCC | AGT | GCA | CGT | GTC | CAA | CAA | ACC | TGG | TCC | GTG | 795 |
| Cys | Met | His | Arg | Trp | Pro | Ser | Ala | Arg | Val | Gln | Gln | Thr | Trp | Ser | Val |     |
| 205 |     |     |     |     | 210 |     |     |     |     | 215 |     |     |     |     | 220 |     |

| CTA | CTG | CTA | CTG | CTT | TTG | TTC | TTC | ATC | CCG | GGT | GTG | GTT | ATT | GCG | GTG | 843 |
| Leu | Leu | Leu | Leu | Leu | Leu | Phe | Phe | Ile | Pro | Gly | Val | Val | Ile | Ala | Val |     |
|     |     |     |     | 225 |     |     |     |     | 230 |     |     |     |     | 235 |     |     |

| GCC | TAT | GGA | CTC | ATC | TCC | CGC | GAA | CTC | TAC | CTA | GGA | CTC | CAC | TTT | GAT | 891 |
| Ala | Tyr | Gly | Leu | Ile | Ser | Arg | Glu | Leu | Tyr | Leu | Gly | Leu | His | Phe | Asp |     |
|     |     |     |     | 240 |     |     |     |     | 245 |     |     |     |     | 250 |     |     |

| GGT | GAA | AAT | GAC | AGC | GAG | ACC | CAA | AGC | CGG | GCC | CGA | AAC | CAA | GGG | GGC | 939 |
| Gly | Glu | Asn | Asp | Ser | Glu | Thr | Gln | Ser | Arg | Ala | Arg | Asn | Gln | Gly | Gly |     |
|     |     |     |     | 255 |     |     |     |     | 260 |     |     |     |     | 265 |     |     |

| CTG | CCG | GGT | GGG | GCA | GCA | CCA | GGG | CCT | GTC | CAC | CAG | AAC | GGG | GGC | TGC | 987 |
| Leu | Pro | Gly | Gly | Ala | Ala | Pro | Gly | Pro | Val | His | Gln | Asn | Gly | Gly | Cys |     |
|     |     | 270 |     |     |     |     | 275 |     |     |     |     | 280 |     |     |     |     |

| CGG | CCT | GTA | ACC | AGC | GTA | GCT | GGG | GAA | GAC | AGT | GAT | GGC | TGC | TGT | GTG | 1035 |
| Arg | Pro | Val | Thr | Ser | Val | Ala | Gly | Glu | Asp | Ser | Asp | Gly | Cys | Cys | Val |      |
| 285 |     |     |     |     | 290 |     |     |     |     | 295 |     |     |     |     | 300 |      |

| CAA | CTT | CCG | CGT | TCC | CGA | CTG | GAG | ATG | ACA | ACG | CTA | ACC | ACA | CCC | ACT | 1083 |
| Gln | Leu | Pro | Arg | Ser | Arg | Leu | Glu | Met | Thr | Thr | Leu | Thr | Thr | Pro | Thr |      |
|     |     |     |     | 305 |     |     |     |     | 310 |     |     |     |     | 315 |     |      |

| CCT | GGG | CCA | GTC | CCT | GGC | CCT | CGG | CCC | AAC | CAG | GCC | AAG | CTG | CTG | GCT | 1131 |
| Pro | Gly | Pro | Val | Pro | Gly | Pro | Arg | Pro | Asn | Gln | Ala | Lys | Leu | Leu | Ala |      |
|     |     |     | 320 |     |     |     |     | 325 |     |     |     |     | 330 |     |     |      |

| AAG | AAG | CGG | GTG | GTG | CGA | ATG | CTG | CTA | GTG | ATT | GTT | TTG | CTT | TTC | TTC | 1179 |
| Lys | Lys | Arg | Val | Val | Arg | Met | Leu | Leu | Val | Ile | Val | Leu | Leu | Phe | Phe |      |
|     |     | 335 |     |     |     |     | 340 |     |     |     |     | 345 |     |     |     |      |

| CTG | TGT | TGG | CTG | CCA | GTG | TAC | AGC | GTC | AAC | ACG | TGG | CGC | GCC | TTC | GAT | 1227 |
| Leu | Cys | Trp | Leu | Pro | Val | Tyr | Ser | Val | Asn | Thr | Trp | Arg | Ala | Phe | Asp |      |
| 350 |     |     |     |     | 355 |     |     |     |     | 360 |     |     |     |     |     |      |

| GGC | CCA | GGC | GCA | CAA | CGA | GCA | CTC | TCA | GGG | GCC | CCT | ATC | TCT | TTC | ATC | 1275 |
| Gly | Pro | Gly | Ala | Gln | Arg | Ala | Leu | Ser | Gly | Ala | Pro | Ile | Ser | Phe | Ile |      |
| 365 |     |     |     |     | 370 |     |     |     |     | 375 |     |     |     |     | 380 |      |

| CAC | TTG | CTG | AGC | TAC | GTC | TCT | GCT | TGT | GTC | AAC | CCC | CTG | GTC | TAC | TGT | 1323 |
| His | Leu | Leu | Ser | Tyr | Val | Ser | Ala | Cys | Val | Asn | Pro | Leu | Val | Tyr | Cys |      |
|     |     |     |     | 385 |     |     |     |     | 390 |     |     |     |     | 395 |     |      |

| TTC | ATG | CAC | CGC | CGC | TTC | CGC | CAG | GCC | TGC | CTG | GAC | ACA | TGT | GCC | CGC | 1371 |
| Phe | Met | His | Arg | Arg | Phe | Arg | Gln | Ala | Cys | Leu | Asp | Thr | Cys | Ala | Arg |      |
|     |     |     | 400 |     |     |     | 405 |     |     |     |     | 410 |     |     |     |      |

| TGT | TGC | CCA | CGC | CCT | CCA | CGA | GCT | CGC | CCA | CAG | CCT | CTT | CCA | GAT | GAG | 1419 |
| Cys | Cys | Pro | Arg | Pro | Pro | Arg | Ala | Arg | Pro | Gln | Pro | Leu | Pro | Asp | Glu |      |
|     |     | 415 |     |     |     |     | 420 |     |     |     |     | 425 |     |     |     |      |

| GAT | CCT | CCT | ACC | CCC | TCC | ATC | GCT | TCG | CTG | TCC | AGG | CTA | AGC | TAT | ACC | 1467 |
| Asp | Pro | Pro | Thr | Pro | Ser | Ile | Ala | Ser | Leu | Ser | Arg | Leu | Ser | Tyr | Thr |      |
|     | 430 |     |     |     |     | 435 |     |     |     |     | 440 |     |     |     |     |      |

| ACC | ATC | AGC | ACA | CTG | GGG | CCT | GGC | TGAGGGGTTG | GGAGATTGGA | GAAAGAGACA |     |     |     |     |     | 1521 |
| Thr | Ile | Ser | Thr | Leu | Gly | Pro | Gly |            |            |            |     |     |     |     |     |      |
| 445 |     |     |     |     | 450 |     |     |            |            |            |     |     |     |     |     |      |

AGATACATAA TTACTATCAA ATGACCCATC CAAACACATA AGAAACAAAA TTCAGAATTA  1581

ATCAGGTGAA CACCCAACAC CATGGACAGA CCCCTACACA CAGAAAATAG TATCTTTGCT  1641

```
GCCCTACCTG AAACAGATAG GAGTCTCATA GGAAAGGAGG CTCACTTCTG ATAAGGGGCT    1701
GAGTCCCTTC CTAGACATCT TGCACTGACC CCATTACATG GACAGACACA AGGTCCGTAG    1761
CAGTAAACTT TACCTATAAA GGGGAACTCT GACAAGGGCT GATTGGCTCC TCATATGAAC    1821
ATATTACTGA CACTATTCTG TAGTGCCCAT AGCCTAGTGC AGAAGTGACT TAGGACATTG    1881
TGGCTGTTCC CGTTTGACTT CATTATTGCC TTCCTCATCC AGCACTGAAA TTATCAACCA    1941
CACGCCTTTC ACCTTTCGGA GCTGCCGATC GTTCAGCACT GAAAAGTCCC CCCCCCCAC    2001
TCCTTTCCAT TGGAGACTGT GGAAAGTCCT CTTCCCTCCT GCCTCTCCTC CCTCACCAGA    2061
CCACATCATA AAAGGATAAG TGACTTAGTG TCCTCCTGGA CTTCTTGAGG TAGGTGAACA    2121
GGTGTGGTTT ATGGGAAGCT TCTTCATTTA TTGGCTCCCA TGACTAATCT ACCCCATATC    2181
CAACCTTGTG CAAAAAGGCC AGGGTATGAA GATAGGGATG AGCGTACCCT CTCTTGGTTG    2241
TC                                                                   2243
```

( 2 ) INFORMATION FOR SEQ ID NO:16:

( i ) SEQUENCE CHARACTERISTICS:
       ( A ) LENGTH: 452 amino acids
       ( B ) TYPE: amino acid
       ( D ) TOPOLOGY: linear ( i i ) MOLECULE TYPE: protein ( x i ) SEQUENCE DESCRIPTION: SEQ ID NO:16:

```
Met Glu Leu Leu Lys Leu Asn Arg Ser Val Gln Gly Pro Gly Pro Gly
 1               5                  10                  15
Ser Gly Ser Ser Leu Cys Arg Pro Gly Val Ser Leu Leu Asn Ser Ser
                20                  25                  30
Ser Ala Gly Asn Leu Ser Cys Asp Pro Pro Arg Ile Arg Gly Thr Gly
            35                  40                  45
Thr Arg Glu Leu Glu Met Ala Ile Arg Ile Thr Leu Tyr Ala Val Ile
     50                  55                  60
Phe Leu Met Ser Val Gly Gly Asn Val Leu Ile Ile Val Val Leu Gly
 65                  70                  75                  80
Leu Ser Arg Arg Leu Arg Thr Val Thr Asn Ala Phe Leu Leu Ser Leu
                85                  90                  95
Ala Val Ser Asp Leu Leu Leu Ala Val Ala Cys Met Pro Phe Thr Leu
                100                 105                 110
Leu Pro Asn Leu Met Gly Thr Phe Ile Phe Gly Thr Val Ile Cys Lys
            115                 120                 125
Ala Ile Ser Tyr Leu Met Gly Val Ser Val Ser Val Ser Thr Leu Asn
    130                 135                 140
Leu Val Ala Ile Ala Leu Glu Arg Tyr Ser Ala Ile Cys Arg Pro Leu
145                 150                 155                 160
Gln Ala Arg Val Trp Gln Thr Arg Ser His Ala Ala Arg Val Ile Leu
                165                 170                 175
Ala Thr Trp Leu Leu Ser Gly Leu Leu Met Val Pro Tyr Pro Val Tyr
            180                 185                 190
Thr Met Val Gln Pro Val Gly Pro Arg Val Leu Gln Cys Met His Arg
    195                 200                 205
Trp Pro Ser Ala Arg Val Gln Gln Thr Trp Ser Val Leu Leu Leu Leu
210                 215                 220
Leu Leu Phe Phe Ile Pro Gly Val Val Ile Ala Val Ala Tyr Gly Leu
225                 230                 235                 240
Ile Ser Arg Glu Leu Tyr Leu Gly Leu His Phe Asp Gly Glu Asn Asp
                245                 250                 255
```

```
Ser Glu Thr Gln Ser Arg Ala Arg Asn Gln Gly Gly Leu Pro Gly Gly
            260                 265                 270
Ala Ala Pro Gly Pro Val His Gln Asn Gly Gly Cys Arg Pro Val Thr
            275                 280                 285
Ser Val Ala Gly Glu Asp Ser Asp Gly Cys Cys Val Gln Leu Pro Arg
        290                 295                 300
Ser Arg Leu Glu Met Thr Thr Leu Thr Thr Pro Thr Pro Gly Pro Val
305                 310                 315                 320
Pro Gly Pro Arg Pro Asn Gln Ala Lys Leu Ala Lys Lys Arg Val
                    325                 330                 335
Val Arg Met Leu Leu Val Ile Val Leu Leu Phe Phe Leu Cys Trp Leu
            340                 345                 350
Pro Val Tyr Ser Val Asn Thr Trp Arg Ala Phe Asp Gly Pro Gly Ala
            355                 360                 365
Gln Arg Ala Leu Ser Gly Ala Pro Ile Ser Phe Ile His Leu Leu Ser
        370                 375                 380
Tyr Val Ser Ala Cys Val Asn Pro Leu Val Tyr Cys Phe Met His Arg
385                 390                 395                 400
Arg Phe Arg Gln Ala Cys Leu Asp Thr Cys Ala Arg Cys Cys Pro Arg
                405                 410                 415
Pro Pro Arg Ala Arg Pro Gln Pro Leu Pro Asp Glu Asp Pro Pro Thr
            420                 425                 430
Pro Ser Ile Ala Ser Leu Ser Arg Leu Ser Tyr Thr Thr Ile Ser Thr
        435                 440                 445
Leu Gly Pro Gly
450
```

( 2 ) INFORMATION FOR SEQ ID NO:17:

( i ) SEQUENCE CHARACTERISTICS:
        ( A ) LENGTH: 384 amino acids
        ( B ) TYPE: amino acid
        ( D ) TOPOLOGY: linear ( v i i ) IMMEDIATE SOURCE:
        ( B ) CLONE: mouse gastrin-releasing peptide receptor ( x i ) SEQUENCE DESCRIPTION: SEQ ID NO:17:

```
Met Ala Pro Asn Asn Cys Ser His Leu Asn Leu Asp Val Asp Pro Phe
1               5                   10                  15
Leu Ser Cys Asn Asp Thr Phe Asn Gln Ser Leu Ser Pro Pro Lys Met
            20                  25                  30
Asp Asn Trp Phe His Pro Gly Phe Ile Tyr Val Ile Pro Ala Val Tyr
            35                  40                  45
Gly Leu Ile Ile Val Ile Gly Leu Ile Gly Asn Ile Thr Leu Ile Lys
        50                  55                  60
Ile Phe Cys Thr Val Lys Ser Met Arg Asn Val Pro Asn Leu Phe Ile
65                  70                  75                  80
Ser Ser Leu Ala Leu Gly Asp Leu Leu Leu Leu Val Thr Cys Ala Pro
                85                  90                  95
Val Asp Ala Ser Lys Tyr Leu Ala Asp Arg Trp Leu Phe Gly Arg Ile
            100                 105                 110
Gly Cys Lys Leu Ile Pro Phe Ile Gln Leu Thr Ser Val Gly Val Ser
            115                 120                 125
Val Phe Thr Leu Thr Ala Leu Ser Ala Asp Arg Tyr Lys Ala Ile Val
        130                 135                 140
Arg Pro Met Asp Ile Gln Ala Ser His Ala Leu Met Lys Ile Cys Leu
145                 150                 155                 160
```

```
Lys  Ala  Ala  Leu  Ile  Trp  Ile  Val  Ser  Met  Leu  Leu  Ala  Ile  Pro  Glu
               165                      170                      175
Ala  Val  Phe  Ser  Asp  Leu  His  Pro  Phe  His  Val  Lys  Asp  Thr  Asn  Gln
               180                      185                      190
Thr  Phe  Ile  Ser  Cys  Ala  Pro  Tyr  Pro  His  Ser  Asn  Glu  Leu  His  Pro
               195                      200                      205
Lys  Ile  His  Ser  Met  Ala  Ser  Phe  Leu  Val  Phe  Tyr  Val  Ile  Pro  Leu
     210                      215                      220
Ala  Ile  Ile  Ser  Val  Tyr  Tyr  Phe  Ile  Ala  Arg  Asn  Leu  Ile  Gln
225                      230                      235                      240
Ser  Ala  Tyr  Asn  Leu  Pro  Val  Glu  Gly  Asn  Ile  His  Val  Lys  Lys  Gln
                    245                      250                      255
Ile  Glu  Ser  Arg  Lys  Arg  Leu  Ala  Lys  Thr  Val  Leu  Val  Phe  Val  Gly
               260                      265                      270
Leu  Phe  Ala  Phe  Cys  Trp  Leu  Pro  Asn  His  Val  Ile  Tyr  Leu  Tyr  Arg
          275                      280                      285
Ser  Tyr  His  Tyr  Ser  Glu  Val  Asp  Thr  Ser  Met  Leu  His  Phe  Val  Thr
     290                      295                      300
Ser  Ile  Cys  Ala  His  Leu  Leu  Ala  Phe  Thr  Asn  Ser  Cys  Val  Asn  Pro
305                      310                      315                      320
Phe  Ala  Leu  Tyr  Leu  Leu  Ser  Lys  Ser  Phe  Arg  Lys  Gln  Phe  Asn  Thr
                    325                      330                      335
Gln  Leu  Leu  Cys  Cys  Gln  Pro  Gly  Leu  Met  Asn  Arg  Ser  His  Ser  Thr
               340                      345                      350
Gly  Arg  Ser  Thr  Thr  Cys  Met  Thr  Ser  Phe  Lys  Ser  Thr  Asn  Pro  Ser
          355                      360                      365
Ala  Thr  Phe  Ser  Leu  Ile  Asn  Arg  Asn  Ile  Cys  His  Glu  Gly  Tyr  Val
     370                      375                      380
```

( 2 ) INFORMATION FOR SEQ ID NO:18:

( i ) SEQUENCE CHARACTERISTICS:
    ( A ) LENGTH: 390 amino acids
    ( B ) TYPE: amino acid
    ( D ) TOPOLOGY: linear ( v i i ) IMMEDIATE SOURCE:
    ( B ) CLONE: rat neuromedin B receptor ( x i ) SEQUENCE DESCRIPTION: SEQ ID NO:18:

```
Met  Pro  Pro  Arg  Ser  Leu  Pro  Asn  Leu  Ser  Leu  Pro  Thr  Glu  Ala  Ser
1                   5                        10                       15
Glu  Ser  Glu  Leu  Glu  Pro  Glu  Val  Trp  Glu  Asn  Asp  Phe  Leu  Pro  Asp
               20                       25                       30
Ser  Asp  Gly  Thr  Thr  Ala  Glu  Leu  Val  Ile  Arg  Cys  Val  Ile  Pro  Ser
          35                       40                       45
Leu  Tyr  Leu  Ile  Ile  Ile  Ser  Val  Gly  Leu  Leu  Gly  Asn  Ile  Met  Leu
     50                       55                       60
Val  Lys  Ile  Phe  Leu  Thr  Asn  Ser  Thr  Met  Arg  Ser  Val  Pro  Asn  Ile
65                       70                       75                       80
Phe  Ile  Ser  Asn  Leu  Ala  Ala  Gly  Asp  Leu  Leu  Leu  Leu  Leu  Thr  Cys
                    85                       90                       95
Val  Pro  Val  Asp  Ala  Ser  Arg  Tyr  Phe  Phe  Asp  Glu  Trp  Val  Phe  Gly
               100                      105                      110
Lys  Leu  Gly  Cys  Lys  Leu  Ile  Pro  Ala  Ile  Gln  Leu  Thr  Ser  Val  Gly
          115                      120                      125
Val  Ser  Val  Phe  Thr  Leu  Thr  Ala  Leu  Ser  Ala  Asp  Arg  Tyr  Arg  Ala
     130                      135                      140
```

| | | | | | | | | | | | | | | |
|---|---|---|---|---|---|---|---|---|---|---|---|---|---|---|
| Ile 145 | Val | Asn | Pro | Met | Asp 150 | Met | Gln | Thr | Ser | Gly 155 | Val | Val | Leu | Trp | Thr 160 |
| Ser | Leu | Lys | Ala | Val 165 | Gly | Ile | Trp | Val | Val 170 | Ser | Val | Leu | Leu | Ala 175 | Val |
| Pro | Glu | Ala | Val 180 | Phe | Ser | Glu | Val | Ala 185 | Arg | Ile | Gly | Ser | Ser 190 | Asp | Asn |
| Ser | Ser | Phe 195 | Thr | Ala | Cys | Ile | Pro 200 | Tyr | Pro | Gln | Thr | Asp 205 | Glu | Leu | His |
| Pro | Lys 210 | Ile | His | Ser | Val | Leu 215 | Ile | Phe | Leu | Val | Tyr 220 | Phe | Leu | Ile | Pro |
| Leu 225 | Val | Ile | Ile | Ser | Ile 230 | Tyr | Tyr | Tyr | His | Ile 235 | Ala | Lys | Thr | Leu | Ile 240 |
| Arg | Ser | Ala | His | Asn 245 | Leu | Pro | Gly | Glu | Tyr 250 | Asn | Glu | His | Thr | Lys 255 | Lys |
| Gln | Met | Glu | Thr 260 | Arg | Lys | Arg | Leu | Ala 265 | Lys | Ile | Val | Leu | Val 270 | Phe | Val |
| Gly | Cys | Phe 275 | Val | Phe | Cys | Trp | Phe 280 | Pro | Asn | His | Ile | Leu 285 | Tyr | Leu | Tyr |
| Arg | Ser 290 | Phe | Asn | Tyr | Lys | Glu 295 | Ile | Asp | Pro | Ser | Leu 300 | Gly | His | Met | Ile |
| Val 305 | Thr | Leu | Val | Ala | Arg 310 | Val | Leu | Ser | Phe | Ser 315 | Asn | Ser | Cys | Val | Asn 320 |
| Pro | Phe | Ala | Leu | Tyr 325 | Leu | Leu | Ser | Glu | Ser 330 | Phe | Arg | Lys | His | Phe 335 | Asn |
| Ser | Gln | Leu | Cys 340 | Cys | Gly | Gln | Lys | Ser 345 | Tyr | Pro | Glu | Arg | Ser 350 | Thr | Ser |
| Tyr | Leu | Leu 355 | Ser | Ser | Ser | Ala | Val 360 | Arg | Met | Thr | Ser | Leu 365 | Lys | Ser | Asn |
| Ala | Lys 370 | Asn | Val | Val | Thr | Asn 375 | Ser | Val | Leu | Leu | Asn 380 | Gly | His | Ser | Thr |
| Lys 385 | Gln | Glu | Ile | Ala | Leu 390 | | | | | | | | | | |

( 2 ) INFORMATION FOR SEQ ID NO:19:

( i ) SEQUENCE CHARACTERISTICS:
        ( A ) LENGTH: 369 amino acids
        ( B ) TYPE: amino acid
        ( D ) TOPOLOGY: linear ( v i i ) IMMEDIATE SOURCE:
        ( B ) CLONE: rat substance K receptor ( x i ) SEQUENCE DESCRIPTION: SEQ ID NO:19:

| | | | | | | | | | | | | | | |
|---|---|---|---|---|---|---|---|---|---|---|---|---|---|---|
| Met 1 | Gly | Thr | Arg | Ala 5 | Ile | Val | Ser | Asp | Ala 10 | Asn | Ile | Leu | Ser | Gly 15 | Leu |
| Glu | Ser | Asn | Ala 20 | Thr | Gly | Val | Thr | Ala 25 | Phe | Ser | Met | Pro | Gly 30 | Trp | Gln |
| Leu | Ala | Leu 35 | Trp | Ala | Thr | Ala | Tyr 40 | Leu | Ala | Leu | Val | Leu 45 | Val | Ala | Val |
| Thr | Gly 50 | Asn | Ala | Thr | Val | Ile 55 | Trp | Ile | Ile | Leu | Ala 60 | His | Glu | Arg | Met |
| Arg 65 | Thr | Val | Thr | Asn | Tyr 70 | Phe | Ile | Ile | Asn | Leu 75 | Ala | Leu | Ala | Asp | Leu 80 |
| Cys | Met | Ala | Ala | Phe 85 | Asn | Ala | Thr | Phe | Asn 90 | Phe | Ile | Tyr | Ala | Ser 95 | His |
| Asn | Ile | Trp | Tyr | Phe 100 | Gly | Arg | Ala | Phe | Cys 105 | Tyr | Phe | Gln | Asn | Leu 110 | Phe |

```
Pro  Ile  Thr  Ala  Met  Phe  Val  Ser  Ile  Tyr  Ser  Met  Thr  Ala  Ile  Ala
          115                      120                      125

Ala  Asp  Arg  Tyr  Met  Ala  Ile  Val  His  Pro  Phe  Gln  Pro  Arg  Leu  Ser
     130                      135                     140

Ala  Pro  Ser  Thr  Lys  Ala  Ile  Ile  Ala  Gly  Ile  Trp  Leu  Val  Ala  Leu
145                           150                     155                      160

Ala  Leu  Ala  Ser  Pro  Gln  Cys  Phe  Tyr  Ser  Thr  Ile  Thr  Val  Asp  Glu
               165                      170                          175

Gly  Ala  Thr  Lys  Cys  Val  Val  Ala  Trp  Pro  Asn  Asp  Asn  Gly  Gly  Lys
               180                      185                     190

Met  Leu  Leu  Leu  Tyr  His  Leu  Val  Val  Phe  Val  Leu  Ile  Tyr  Phe  Leu
          195                      200                     205

Pro  Leu  Leu  Val  Met  Phe  Gly  Ala  Tyr  Ser  Val  Ile  Gly  Leu  Thr  Leu
     210                      215                     220

Trp  Lys  Arg  Ala  Val  Pro  Arg  His  Gln  Ala  His  Gly  Ala  Asn  Leu  Arg
225                      230                     235                           240

His  Leu  Gln  Ala  Lys  Lys  Lys  Phe  Val  Lys  Ala  Met  Val  Leu  Val  Val
                    245                     250                          255

Leu  Thr  Phe  Ala  Ile  Cys  Trp  Leu  Pro  Tyr  His  Leu  Tyr  Phe  Ile  Leu
               260                      265                     270

Gly  Thr  Phe  Gln  Glu  Asp  Ile  Tyr  Tyr  His  Lys  Phe  Ile  Gln  Gln  Val
               275                      280                     285

Tyr  Leu  Ala  Leu  Phe  Trp  Leu  Ala  Met  Ser  Ser  Thr  Met  Tyr  Asn  Pro
     290                      295                     300

Ile  Ile  Tyr  Cys  Cys  Leu  Asn  His  Arg  Phe  Arg  Ser  Gly  Phe  Arg  Leu
305                      310                     315                           320

Ala  Phe  Arg  Cys  Cys  Pro  Trp  Val  Thr  Pro  Thr  Glu  Glu  Asp  Arg  Leu
                    325                     330                          335

Glu  Leu  Thr  His  Thr  Pro  Ser  Leu  Ser  Arg  Arg  Val  Asn  Arg  Cys  His
               340                      345                     350

Thr  Lys  Glu  Thr  Leu  Phe  Met  Thr  Gly  Asp  Met  Thr  His  Ser  Glu  Ala
          355                      360                     365

Thr
```

( 2 ) INFORMATION FOR SEQ ID NO:20:

( i ) SEQUENCE CHARACTERISTICS:
        ( A ) LENGTH: 372 amino acids
        ( B ) TYPE: amino acid
        ( D ) TOPOLOGY: linear ( v i i ) IMMEDIATE SOURCE:
        ( B ) CLONE: rat substance P receptor ( x i ) SEQUENCE DESCRIPTION: SEQ ID NO:20:

```
Met  Asp  Asn  Val  Leu  Pro  Met  Asp  Ser  Asp  Leu  Phe  Pro  Asn  Ile  Ser
1                   5                        10                      15

Thr  Asn  Thr  Ser  Glu  Ser  Asn  Gln  Phe  Val  Gln  Pro  Thr  Trp  Gln  Ile
               20                       25                      30

Val  Leu  Trp  Ala  Ala  Ala  Tyr  Thr  Val  Ile  Val  Val  Thr  Ser  Val  Val
          35                       40                      45

Gly  Asn  Val  Val  Val  Ile  Trp  Ile  Ile  Leu  Ala  His  Lys  Arg  Met  Arg
     50                       55                      60

Thr  Val  Thr  Asn  Tyr  Phe  Leu  Val  Asn  Leu  Ala  Phe  Ala  Glu  Ala  Cys
65                        70                      75                           80

Met  Ala  Ala  Phe  Asn  Thr  Val  Val  Asn  Phe  Thr  Tyr  Ala  Val  His  Asn
               85                       90                      95
```

| | | | | | | | | | | | | | | |
|---|---|---|---|---|---|---|---|---|---|---|---|---|---|---|
| Val | Trp | Tyr | Tyr<br>100 | Gly | Leu | Phe | Tyr | Cys<br>105 | Lys | Phe | His | Asn | Phe<br>110 | Pro |
| Ile | Ala | Ala<br>115 | Leu | Phe | Ala | Ser | Ile<br>120 | Tyr | Ser | Met | Thr | Ala<br>125 | Val | Ala | Phe |
| Asp | Arg<br>130 | Tyr | Met | Ala | Ile<br>135 | Ile | His | Pro | Leu | Gln<br>140 | Pro | Arg | Leu | Ser | Ala |
| Thr<br>145 | Ala | Thr | Lys | Val<br>150 | Val | Ile | Phe | Val | Ile<br>155 | Trp | Val | Leu | Ala | Leu | Leu<br>160 |
| Leu | Ala | Phe | Pro | Gln<br>165 | Gly | Tyr | Tyr | Ser | Thr<br>170 | Thr | Glu | Thr | Met | Pro<br>175 | Ser |
| Arg | Val | Val | Cys<br>180 | Met | Ile | Glu | Trp | Pro<br>185 | Glu | His | Pro | Asn | Arg<br>190 | Thr | Tyr |
| Glu | Lys | Ala<br>195 | Tyr | His | Ile | Cys | Val<br>200 | Thr | Val | Leu | Ile | Tyr<br>205 | Phe | Leu | Pro |
| Leu | Leu<br>210 | Val | Ile | Gly | Tyr | Ala<br>215 | Tyr | Thr | Val | Val | Gly<br>220 | Ile | Thr | Leu | Trp |
| Ala<br>225 | Ser | Glu | Ile | Pro | Gly<br>230 | Asp | Ser | Ser | Asp | Arg<br>235 | Tyr | His | Glu | Gln | Val<br>240 |
| Ser | Ala | Lys | Arg | Lys<br>245 | Val | Val | Lys | Met | Met<br>250 | Ile | Val | Val | Val | Cys<br>255 | Thr |
| Phe | Ala | Ile | Cys<br>260 | Trp | Leu | Pro | Phe | His<br>265 | Val | Phe | Phe | Leu | Leu<br>270 | Pro | Tyr |
| Ile | Asn | Pro<br>275 | Asp | Leu | Tyr | Leu | Lys<br>280 | Lys | Phe | Ile | Gln | Gln<br>285 | Val | Tyr | Leu |
| Ala | Ser<br>290 | Met | Trp | Leu | Ala | Met<br>295 | Ser | Ser | Thr | Met | Tyr<br>300 | Asn | Pro | Ile | Ile |
| Tyr<br>305 | Cys | Cys | Leu | Asn | Asp<br>310 | Arg | Phe | Arg | Leu | Gly<br>315 | Phe | Lys | His | Ala | Phe<br>320 |
| Arg | Cys | Cys | Pro | Phe<br>325 | Ile | Ser | Ala | Gly | Asp<br>330 | Tyr | Glu | Gly | Leu | Glu | Met<br>335 |
| Lys | Ser | Thr | Arg<br>340 | Tyr | Leu | Gln | Thr | Gln<br>345 | Ser | Ser | Val | Tyr | Lys<br>350 | Val | Ser |
| Arg | Leu | Glu | Thr<br>355 | Thr | Ile | Ser | Thr | Val<br>360 | Val | Gly | Ala | His | Glu<br>365 | Glu | Glu |
| Pro | Glu | Glu | Gly<br>370 | | | | | | | | | | | | |

(2) INFORMATION FOR SEQ ID NO:21:

(i) SEQUENCE CHARACTERISTICS:
(A) LENGTH: 411 amino acids
(B) TYPE: amino acid
(D) TOPOLOGY: linear (xi) SEQUENCE DESCRIPTION: SEQ ID NO:21:

| | | | | | | | | | | | | | | |
|---|---|---|---|---|---|---|---|---|---|---|---|---|---|---|
| Met<br>1 | Ala | Ser | Val | Pro<br>5 | Arg | Gly | Glu | Asn | Trp<br>10 | Thr | Asp | Gly | Thr | Val<br>15 | Glu |
| Val | Gly | Thr | His<br>20 | Thr | Gly | Asn | Leu | Ser<br>25 | Ser | Ala | Leu | Gly | Leu<br>30 | Val | Thr | Glu |
| Trp | Leu | Ala<br>35 | Leu | Gln | Ala | Gly | Asn<br>40 | Phe | Ser | Ser | Ala | Leu<br>45 | Gly | Leu | Pro |
| Ala | Thr<br>50 | Thr | Gln | Ala | Pro<br>55 | Ser | Gln | Val | Arg | Ala<br>60 | Asn | Leu | Thr | Asn | Gln |
| Phe<br>65 | Val | Gln | Pro | Ser | Trp<br>70 | Arg | Ile | Ala | Leu | Trp<br>75 | Ser | Leu | Ala | Tyr | Gly<br>80 |
| Leu | Val | Val | Ala | Val<br>85 | Ala | Val | Phe | Gly | Asn<br>90 | Leu | Ile | Val | Ile | Trp<br>95 | Ile |

|  |  |  |  |  |  |  |  |  |  |  |  |  |  |  |
|---|---|---|---|---|---|---|---|---|---|---|---|---|---|---|
| Ile | Leu | Ala | His | Lys | Arg | Met | Arg | Thr | Val | Thr | Asn | Tyr | Phe | Leu | Val |
|  |  |  | 100 |  |  |  | 105 |  |  |  |  |  | 110 |  |  |
| Asn | Leu | Ala | Phe | Ser | Asp | Ala | Ser | Val | Ala | Ala | Phe | Asn | Thr | Leu | Ile |
|  |  |  | 115 |  |  |  | 120 |  |  |  |  |  | 125 |  |  |
| Asn | Phe | Ile | Tyr | Gly | Leu | His | Ser | Glu | Trp | Tyr | Phe | Gly | Ala | Asn | Tyr |
|  |  | 130 |  |  |  | 135 |  |  |  |  | 140 |  |  |  |  |
| Cys | Arg | Phe | Gln | Asn | Phe | Phe | Pro | Ile | Thr | Ala | Val | Phe | Ala | Ser | Ile |
| 145 |  |  |  |  | 150 |  |  |  |  | 155 |  |  |  |  | 160 |
| Tyr | Ser | Met | Thr | Ala | Ile | Ala | Val | Asp | Arg | Tyr | Met | Ala | Ile | Ile | Asp |
|  |  |  |  | 165 |  |  |  |  | 170 |  |  |  |  | 175 |  |
| Pro | Leu | Lys | Pro | Arg | Leu | Ser | Ala | Thr | Ala | Thr | Lys | Ile | Val | Ile | Gly |
|  |  |  | 180 |  |  |  |  | 185 |  |  |  |  | 190 |  |  |
| Ser | Ile | Trp | Ile | Leu | Ala | Phe | Leu | Leu | Ala | Phe | Pro | Gln | Cys | Leu | Tyr |
|  |  | 195 |  |  |  |  | 200 |  |  |  |  | 205 |  |  |  |
| Ser | Lys | Ile | Lys | Val | Met | Pro | Gly | Arg | Thr | Leu | Cys | Tyr | Val | Gln | Trp |
|  | 210 |  |  |  |  | 215 |  |  |  |  | 220 |  |  |  |  |
| Pro | Glu | Gly | Pro | Lys | Gln | His | Phe | Thr | Tyr | His | Ile | Ile | Val | Ile | Ile |
| 225 |  |  |  |  | 230 |  |  |  |  | 235 |  |  |  |  | 240 |
| Leu | Val | Tyr | Cys | Phe | Pro | Leu | Leu | Ile | Met | Gly | Val | Thr | Tyr | Thr | Ile |
|  |  |  |  | 245 |  |  |  |  | 250 |  |  |  |  | 255 |  |
| Val | Gly | Ile | Thr | Leu | Trp | Gly | Gly | Glu | Ile | Pro | Gly | Asp | Thr | Cys | Asp |
|  |  |  | 260 |  |  |  |  | 265 |  |  |  |  | 270 |  |  |
| Lys | Tyr | His | Glu | Gln | Leu | Lys | Ala | Lys | Arg | Lys | Val | Val | Lys | Met | Met |
|  |  | 275 |  |  |  |  | 280 |  |  |  |  | 285 |  |  |  |
| Ile | Ile | Val | Val | Val | Thr | Phe | Ala | Ile | Cys | Trp | Leu | Pro | Tyr | His | Val |
|  | 290 |  |  |  |  | 295 |  |  |  |  | 300 |  |  |  |  |
| Tyr | Phe | Ile | Leu | Thr | Ala | Ile | Tyr | Gln | Gln | Leu | Asn | Arg | Trp | Lys | Tyr |
| 305 |  |  |  | 310 |  |  |  |  | 315 |  |  |  |  |  | 320 |
| Ile | Gln | Gln | Val | Tyr | Leu | Ala | Ser | Phe | Trp | Leu | Ala | Met | Ser | Ser | Thr |
|  |  |  |  | 325 |  |  |  |  | 330 |  |  |  |  | 335 |  |
| Met | Tyr | Asn | Pro | Ile | Ile | Tyr | Cys | Cys | Leu | Asn | Lys | Arg | Phe | Arg | Ala |
|  |  |  | 340 |  |  |  |  | 345 |  |  |  |  | 350 |  |  |
| Gly | Phe | Lys | Arg | Ala | Phe | Arg | Trp | Cys | Pro | Phe | Ile | Gln | Val | Ser | Ser |
|  |  | 355 |  |  |  |  | 360 |  |  |  |  | 365 |  |  |  |
| Tyr | Asp | Glu | Leu | Glu | Leu | Lys | Thr | Thr | Arg | Phe | His | Pro | Thr | Arg | Gln |
|  | 370 |  |  |  |  | 375 |  |  |  |  | 380 |  |  |  |  |
| Ser | Ser | Leu | Tyr | Thr | Val | Ser | Arg | Met | Glu | Ser | Val | Thr | Val | Leu | Phe |
| 385 |  |  |  |  | 390 |  |  |  |  | 395 |  |  |  |  | 400 |
| Asp | Pro | Asn | Asp | Gly | Asp | Pro | Thr | Lys | Ser | Ser |  |  |  |  |  |
|  |  |  |  | 405 |  |  |  |  | 410 |  |  |  |  |  |  |

( 2 ) INFORMATION FOR SEQ ID NO:22:

( i ) SEQUENCE CHARACTERISTICS:
        ( A ) LENGTH: 1621 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: guinea pig gallbladder and pancreas CCKA
            receptor ( i x ) FEATURE:
        ( A ) NAME/KEY: CDS
        ( B ) LOCATION: 205..1497

( x i ) SEQUENCE DESCRIPTION: SEQ ID NO:22:

| CGCAGGATGC | GTGCCCAGCT | GGACGGAGGG | TAGTGAACTC | CAGGTGCCTT | TAGGAATGGC | 60 |
| TGCAAAAGCC | CACACCTGGC | AATCACTCTC | TGCCTGCCTC | TCCCCGGCAG | GTTGCATTTG | 120 |

```
GGAGGCGCTC TGGTCATCAG AGGAATGAGC GTGGAGAGAG CTGTTTGCCA GCCCGCCAGC        180

CCCTGGTGGG AAGCAGAGGC GAGG ATG GAC GTG GTA GAC AGC CTT TTT GTG          231
                             Met Asp Val Val Asp Ser Leu Phe Val
                              1               5

AAT GGG AGC AAC ATC ACT TCT GCC TGC GAG CTC GGC TTT GAA AAT GAG         279
Asn Gly Ser Asn Ile Thr Ser Ala Cys Glu Leu Gly Phe Glu Asn Glu
 10              15              20              25

ACA CTT TTC TGC TTG GAT CGG CCC CGG CCT TCC AAA GAG TGG CAG CCG         327
Thr Leu Phe Cys Leu Asp Arg Pro Arg Pro Ser Lys Glu Trp Gln Pro
             30              35              40

GCG GTG CAG ATT CTC TTG TAT TCC TTG ATA TTC CTG CTC AGC GTG CTG         375
Ala Val Gln Ile Leu Leu Tyr Ser Leu Ile Phe Leu Leu Ser Val Leu
                 45              50              55

GGA AAC ACG CTG GTA ATC ACG GTG CTG ATT CGG AAC AAG AGG ATG AGG         423
Gly Asn Thr Leu Val Ile Thr Val Leu Ile Arg Asn Lys Arg Met Arg
         60              65              70

ACG GTC ACT AAC ATC TTC CTG CTC TCA CTG GCT GTC AGT GAC CTC ATG         471
Thr Val Thr Asn Ile Phe Leu Leu Ser Leu Ala Val Ser Asp Leu Met
     75              80              85

CTC TGC CTC TTC TGC ATG CCC TTC AAC CTC ATC CCC AGC CTG CTC AAG         519
Leu Cys Leu Phe Cys Met Pro Phe Asn Leu Ile Pro Ser Leu Leu Lys
 90              95             100             105

GAT TTC ATC TTC GGG AGT GCC GTG TGC AAG ACC ACC ACC TAC TTC ATG         567
Asp Phe Ile Phe Gly Ser Ala Val Cys Lys Thr Thr Thr Tyr Phe Met
             110             115             120

GGC ACC TCT GTG AGT GTA TCC ACC TTT AAT CTG GTG GCC ATA TCG CTG         615
Gly Thr Ser Val Ser Val Ser Thr Phe Asn Leu Val Ala Ile Ser Leu
                 125             130             135

GAG AGA TAC GGA GCA ATT TGC AAA CCC TTA CAG TCC CGC GTC TGG CAA         663
Glu Arg Tyr Gly Ala Ile Cys Lys Pro Leu Gln Ser Arg Val Trp Gln
         140             145             150

ACA AAG TCG CAT GCT TTG AAG GTG ATT GCT GCT ACC TGG TGC CTC TCC         711
Thr Lys Ser His Ala Leu Lys Val Ile Ala Ala Thr Trp Cys Leu Ser
     155             160             165

TTT ACC ATC ATG ACC CCC TAC CCC ATC TAC AGC AAC CTG GTG CCT TTT         759
Phe Thr Ile Met Thr Pro Tyr Pro Ile Tyr Ser Asn Leu Val Pro Phe
170             175             180             185

ACC AAA AAT AAC AAC CAG ACC GGG AAC ATG TGC CGC TTC CTA CTG CCA         807
Thr Lys Asn Asn Asn Gln Thr Gly Asn Met Cys Arg Phe Leu Leu Pro
             190             195             200

AAC GAT GTT ATG CAG CAG ACC TGG CAC ACT TTC CTG TTA CTC ATC CTC         855
Asn Asp Val Met Gln Gln Thr Trp His Thr Phe Leu Leu Leu Ile Leu
                 205             210             215

TTT CTT ATT CCC GGA ATT GTG ATG ATG GTG GCA TAT GGA CTG ATT TCT         903
Phe Leu Ile Pro Gly Ile Val Met Met Val Ala Tyr Gly Leu Ile Ser
         220             225             230

CTG GAA CTT TAC CAA GGA ATA AAA TTC GAT GCT ATC CAG AAG AAA TCT         951
Leu Glu Leu Tyr Gln Gly Ile Lys Phe Asp Ala Ile Gln Lys Lys Ser
     235             240             245

GCT AAA GAA AGG AAG ACA AGC ACT GGC AGC AGT GGC CCG ATG GAG GAC         999
Ala Lys Glu Arg Lys Thr Ser Thr Gly Ser Ser Gly Pro Met Glu Asp
250             255             260             265

AGT GAT GGG TGT TAC CTG CAG AAG TCC AGG CAC CCC AGA AAG CTG GAG        1047
Ser Asp Gly Cys Tyr Leu Gln Lys Ser Arg His Pro Arg Lys Leu Glu
             270             275             280

CTT CGG CAG CTG TCC CCC AGC AGC AGT GGC AGC AAC AGG ATC AAT CGT        1095
Leu Arg Gln Leu Ser Pro Ser Ser Ser Gly Ser Asn Arg Ile Asn Arg
                 285             290             295

ATC CGG AGC AGC AGC TCC ACC GCC AAC TTG ATG GCC AAA AAG CGG GTG        1143
Ile Arg Ser Ser Ser Ser Thr Ala Asn Leu Met Ala Lys Lys Arg Val
```

| | | | | | | | | | | | | | | | | |
|---|---|---|---|---|---|---|---|---|---|---|---|---|---|---|---|---|
| | | | 300 | | | | | 305 | | | | | 310 | | | |
| ATC | CGC | ATG | CTC | ATC | GTC | ATT | GTG | GTC | CTC | TTC | TTC | CTG | TGC | TGG | ATG | 1191 |
| Ile | Arg | Met | Leu | Ile | Val | Ile | Val | Val | Leu | Phe | Phe | Leu | Cys | Trp | Met | |
| | 315 | | | | 320 | | | | | 325 | | | | | | |
| CCC | ATC | TTC | AGC | GCC | AAT | GCC | TGG | CGG | GCA | TAC | GAC | ACC | GTC | TCT | GCC | 1239 |
| Pro | Ile | Phe | Ser | Ala | Asn | Ala | Trp | Arg | Ala | Tyr | Asp | Thr | Val | Ser | Ala | |
| 330 | | | | | 335 | | | | | 340 | | | | | 345 | |
| GAG | CGC | CAC | CTC | TCT | GGG | ACA | CCT | ATC | TCC | TTC | ATC | CTC | CTG | CTC | TCT | 1287 |
| Glu | Arg | His | Leu | Ser | Gly | Thr | Pro | Ile | Ser | Phe | Ile | Leu | Leu | Leu | Ser | |
| | | | | 350 | | | | | 355 | | | | | 360 | | |
| TAC | ACC | TCC | TCC | TGC | GTC | AAC | CCC | ATC | ATC | TAC | TGC | TTC | ATG | AAC | AAA | 1335 |
| Tyr | Thr | Ser | Ser | Cys | Val | Asn | Pro | Ile | Ile | Tyr | Cys | Phe | Met | Asn | Lys | |
| | | | 365 | | | | | 370 | | | | | 375 | | | |
| CGA | TTC | CGT | CTT | GGC | TTC | ATG | GCC | ACC | TTC | CCC | TGC | TGT | CCC | AAC | CCA | 1383 |
| Arg | Phe | Arg | Leu | Gly | Phe | Met | Ala | Thr | Phe | Pro | Cys | Cys | Pro | Asn | Pro | |
| | | 380 | | | | | 385 | | | | | 390 | | | | |
| GGT | ACC | CCT | GGG | GTG | AGA | GGA | GAG | ATG | GGA | GAG | GAG | GAG | GAA | GGC | AGG | 1431 |
| Gly | Thr | Pro | Gly | Val | Arg | Gly | Glu | Met | Gly | Glu | Glu | Glu | Glu | Gly | Arg | |
| 395 | | | | | 400 | | | | | 405 | | | | | | |
| ACC | ACA | GGG | GCG | TCT | TTG | TCC | AGA | TAC | TCC | TAC | AGC | CAC | ATG | AGC | ACC | 1479 |
| Thr | Thr | Gly | Ala | Ser | Leu | Ser | Arg | Tyr | Ser | Tyr | Ser | His | Met | Ser | Thr | |
| 410 | | | | | 415 | | | | | 420 | | | | | 425 | |
| TCT | GCT | CCG | CCC | CCG | TGAGCTGGGC | | CCGGGGCTAC | | ACAGTACAGC | | AGGAAGGAGG | | | | | 1534 |
| Ser | Ala | Pro | Pro | Pro | | | | | | | | | | | | |
| | | | | 430 | | | | | | | | | | | | |

CCACGGGAGG AGGAGGAGAA AAGAAAGGAA AGGAGAAAGC AGGAGAAGCA GGAGGAGGCA  1594

GAAGCAAAAG AGAAGGAAGG CCCAGGT  1621

( 2 ) INFORMATION FOR SEQ ID NO:23:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Met | Asp | Val | Val | Asp | Ser | Leu | Phe | Val | Asn | Gly | Ser | Asn | Ile | Thr | Ser |
| 1 | | | | 5 | | | | | 10 | | | | | 15 | |
| Ala | Cys | Glu | Leu | Gly | Phe | Glu | Asn | Glu | Thr | Leu | Phe | Cys | Leu | Asp | Arg |
| | | | 20 | | | | | 25 | | | | | 30 | | |
| Pro | Arg | Pro | Ser | Lys | Glu | Trp | Gln | Pro | Ala | Val | Gln | Ile | Leu | Leu | Tyr |
| | | 35 | | | | | 40 | | | | | 45 | | | |
| Ser | Leu | Ile | Phe | Leu | Leu | Ser | Val | Leu | Gly | Asn | Thr | Leu | Val | Ile | Thr |
| | 50 | | | | | 55 | | | | | 60 | | | | |
| Val | Leu | Ile | Arg | Asn | Lys | Arg | Met | Arg | Thr | Val | Thr | Asn | Ile | Phe | Leu |
| 65 | | | | | 70 | | | | | 75 | | | | | 80 |
| Leu | Ser | Leu | Ala | Val | Ser | Asp | Leu | Met | Leu | Cys | Leu | Phe | Cys | Met | Pro |
| | | | | 85 | | | | | 90 | | | | | 95 | |
| Phe | Asn | Leu | Ile | Pro | Ser | Leu | Leu | Lys | Asp | Phe | Ile | Phe | Gly | Ser | Ala |
| | | | 100 | | | | | 105 | | | | | 110 | | |
| Val | Cys | Lys | Thr | Thr | Thr | Tyr | Phe | Met | Gly | Thr | Ser | Val | Ser | Val | Ser |
| | | 115 | | | | | 120 | | | | | 125 | | | |
| Thr | Phe | Asn | Leu | Val | Ala | Ile | Ser | Leu | Glu | Arg | Tyr | Gly | Ala | Ile | Cys |
| | 130 | | | | | 135 | | | | | 140 | | | | |
| Lys | Pro | Leu | Gln | Ser | Arg | Val | Trp | Gln | Thr | Lys | Ser | His | Ala | Leu | Lys |
| 145 | | | | | 150 | | | | | 155 | | | | | 160 |
| Val | Ile | Ala | Ala | Thr | Trp | Cys | Leu | Ser | Phe | Thr | Ile | Met | Thr | Pro | Tyr |
| | | | | 165 | | | | | 170 | | | | | 175 | |

```
Pro  Ile  Tyr  Ser  Asn  Leu  Val  Pro  Phe  Thr  Lys  Asn  Asn  Gln  Thr
               180                 185                 190

Gly  Asn  Met  Cys  Arg  Phe  Leu  Leu  Pro  Asn  Asp  Val  Met  Gln  Gln  Thr
          195                      200                 205

Trp  His  Thr  Phe  Leu  Leu  Leu  Ile  Leu  Phe  Leu  Ile  Pro  Gly  Ile  Val
     210                      215                      220

Met  Met  Val  Ala  Tyr  Gly  Leu  Ile  Ser  Leu  Glu  Leu  Tyr  Gln  Gly  Ile
225                      230                 235                           240

Lys  Phe  Asp  Ala  Ile  Gln  Lys  Lys  Ser  Ala  Lys  Glu  Arg  Lys  Thr  Ser
               245                      250                      255

Thr  Gly  Ser  Ser  Gly  Pro  Met  Glu  Asp  Ser  Asp  Gly  Cys  Tyr  Leu  Gln
               260                 265                      270

Lys  Ser  Arg  His  Pro  Arg  Lys  Leu  Glu  Leu  Arg  Gln  Leu  Ser  Pro  Ser
          275                      280                      285

Ser  Ser  Gly  Ser  Asn  Arg  Ile  Asn  Arg  Ile  Arg  Ser  Ser  Ser  Ser  Thr
     290                      295                      300

Ala  Asn  Leu  Met  Ala  Lys  Lys  Arg  Val  Ile  Arg  Met  Leu  Ile  Val  Ile
305                           310                 315                      320

Val  Val  Leu  Phe  Phe  Leu  Cys  Trp  Met  Pro  Ile  Phe  Ser  Ala  Asn  Ala
               325                      330                      335

Trp  Arg  Ala  Tyr  Asp  Thr  Val  Ser  Ala  Glu  Arg  His  Leu  Ser  Gly  Thr
               340                      345                      350

Pro  Ile  Ser  Phe  Ile  Leu  Leu  Leu  Ser  Tyr  Thr  Ser  Ser  Cys  Val  Asn
               355                      360                 365

Pro  Ile  Ile  Tyr  Cys  Phe  Met  Asn  Lys  Arg  Phe  Arg  Leu  Gly  Phe  Met
     370                      375                 380

Ala  Thr  Phe  Pro  Cys  Cys  Pro  Asn  Pro  Gly  Thr  Pro  Gly  Val  Arg  Gly
385                           390                 395                      400

Glu  Met  Gly  Glu  Glu  Glu  Glu  Gly  Arg  Thr  Thr  Gly  Ala  Ser  Leu  Ser
               405                      410                      415

Arg  Tyr  Ser  Tyr  Ser  His  Met  Ser  Thr  Ser  Ala  Pro  Pro  Pro
               420                      425                 430
```

( 2 ) INFORMATION FOR SEQ ID NO:24:

( i ) SEQUENCE CHARACTERISTICS:
        ( A ) LENGTH: 450 amino acids
        ( B ) TYPE: amino acid
        ( D ) TOPOLOGY: linear ( v i i ) IMMEDIATE SOURCE:
        ( B ) CLONE: guinea pig CCKA receptor ( x i ) SEQUENCE DESCRIPTION: SEQ ID NO:24:

```
Met  Ser  Val  Glu  Arg  Ala  Val  Cys  Gln  Pro  Ala  Ser  Pro  Trp  Trp  Glu
1                   5                   10                      15

Ala  Glu  Ala  Arg  Met  Asp  Val  Val  Asp  Ser  Leu  Phe  Val  Asn  Gly  Ser
               20                  25                      30

Asn  Ile  Thr  Ser  Ala  Cys  Glu  Leu  Gly  Phe  Glu  Asn  Glu  Thr  Leu  Phe
          35                  40                      45

Cys  Leu  Asp  Arg  Pro  Arg  Pro  Ser  Lys  Glu  Trp  Gln  Pro  Ala  Val  Gln
     50                  55                      60

Ile  Leu  Leu  Tyr  Ser  Leu  Ile  Phe  Leu  Leu  Ser  Val  Leu  Gly  Asn  Thr
65                  70                      75                           80

Leu  Val  Ile  Thr  Val  Leu  Ile  Arg  Asn  Lys  Arg  Met  Arg  Thr  Val  Thr
               85                      90                      95

Asn  Ile  Phe  Leu  Leu  Ser  Leu  Ala  Val  Ser  Asp  Leu  Met  Leu  Cys  Leu
               100                     105                     110
```

|     |     |     |     |     |     |     |     |     |     |     |     |     |     |     |
| --- | --- | --- | --- | --- | --- | --- | --- | --- | --- | --- | --- | --- | --- | --- |
| Phe | Cys | Met<br>115 | Pro | Phe | Asn | Leu | Ile<br>120 | Pro | Ser | Leu | Leu | Lys<br>125 | Asp | Phe | Ile |
| Phe | Gly<br>130 | Ser | Ala | Val | Cys | Lys<br>135 | Thr | Thr | Thr | Tyr | Phe<br>140 | Met | Gly | Thr | Ser |
| Val<br>145 | Ser | Val | Ser | Thr | Phe<br>150 | Asn | Leu | Val | Ala | Ile<br>155 | Ser | Leu | Glu | Arg | Tyr<br>160 |
| Gly | Ala | Ile | Cys | Lys<br>165 | Pro | Leu | Gln | Ser | Arg<br>170 | Val | Trp | Gln | Thr | Lys<br>175 | Ser |
| His | Ala | Leu | Lys<br>180 | Val | Ile | Ala | Ala | Thr<br>185 | Trp | Cys | Leu | Ser | Phe<br>190 | Thr | Ile |
| Met | Thr | Pro<br>195 | Tyr | Pro | Ile | Tyr | Ser<br>200 | Asn | Leu | Val | Pro | Phe<br>205 | Thr | Lys | Asn |
| Asn | Asn<br>210 | Gln | Thr | Gly | Asn | Met<br>215 | Cys | Arg | Phe | Leu | Leu<br>220 | Pro | Asn | Asp | Val |
| Met<br>225 | Gln | Gln | Thr | Trp | His<br>230 | Thr | Phe | Leu | Leu | Leu<br>235 | Ile | Leu | Phe | Leu | Ile<br>240 |
| Pro | Gly | Ile | Val | Met<br>245 | Met | Val | Ala | Tyr | Gly<br>250 | Leu | Ile | Ser | Leu | Glu<br>255 | Leu |
| Tyr | Gln | Gly | Ile<br>260 | Lys | Phe | Asp | Ala | Ile<br>265 | Gln | Lys | Lys | Ser | Ala<br>270 | Lys | Glu |
| Arg | Lys | Thr<br>275 | Ser | Thr | Gly | Ser | Ser<br>280 | Gly | Pro | Met | Glu | Asp<br>285 | Ser | Asp | Gly |
| Cys | Tyr<br>290 | Leu | Gln | Lys | Ser | Arg<br>295 | His | Pro | Arg | Lys | Leu<br>300 | Glu | Leu | Arg | Gln |
| Leu<br>305 | Ser | Pro | Ser | Ser | Ser<br>310 | Gly | Ser | Asn | Arg | Ile<br>315 | Asn | Arg | Ile | Arg | Ser<br>320 |
| Ser | Ser | Ser | Thr | Ala<br>325 | Asn | Leu | Met | Ala | Lys<br>330 | Lys | Arg | Val | Ile | Arg<br>335 | Met |
| Leu | Ile | Val | Ile<br>340 | Val | Val | Leu | Phe | Phe<br>345 | Leu | Cys | Trp | Met | Pro<br>350 | Ile | Phe |
| Ser | Ala | Asn<br>355 | Ala | Trp | Arg | Ala | Tyr<br>360 | Asp | Thr | Val | Ser | Ala<br>365 | Glu | Arg | His |
| Leu | Ser<br>370 | Gly | Thr | Pro | Ile | Ser<br>375 | Phe | Ile | Leu | Leu | Leu<br>380 | Ser | Tyr | Thr | Ser |
| Ser<br>385 | Cys | Val | Asn | Pro | Ile<br>390 | Ile | Tyr | Cys | Phe | Met<br>395 | Asn | Lys | Arg | Phe | Arg<br>400 |
| Leu | Gly | Phe | Met | Ala<br>405 | Thr | Phe | Pro | Cys | Cys<br>410 | Pro | Asn | Pro | Gly | Thr<br>415 | Pro |
| Gly | Val | Arg | Gly<br>420 | Glu | Met | Gly | Glu<br>425 | Glu | Glu | Glu | Gly | Arg<br>430 | Thr | Thr | Gly |
| Ala | Ser | Leu<br>435 | Ser | Arg | Tyr | Ser | Tyr<br>440 | Ser | His | Met | Ser | Thr<br>445 | Ser | Ala | Pro |
| Pro | Pro<br>450 |     |     |     |     |     |     |     |     |     |     |     |     |     |     |

( 2 ) INFORMATION FOR SEQ ID NO:25:

( i ) SEQUENCE CHARACTERISTICS:
        ( A ) LENGTH: 2015 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: guinea pig gallbladder and pancreas CCKB
            receptor ( i x ) FEATURE:
        ( A ) NAME/KEY: CDS (B) LOCATION: 13..1374

(xi) SEQUENCE DESCRIPTION: SEQ ID NO:25:

```
CTCGGAGGGG CC ATG GAG CTG CTC AAG CTG AAC CGG AGC CTC CAG GGA          48
              Met Glu Leu Leu Lys Leu Asn Arg Ser Leu Gln Gly
                1               5                   10

CCC GGG CCT GGG CCG GGG GCT CCC CTG TGC CGC CCG GCT GGC CCG CTT         96
Pro Gly Pro Gly Pro Gly Ala Pro Leu Cys Arg Pro Ala Gly Pro Leu
            15                  20                  25

CTC AAC AGC AGC GGT GCA GGC AAC GTC AGC TGC GAA ACC CCT CGC ATC        144
Leu Asn Ser Ser Gly Ala Gly Asn Val Ser Cys Glu Thr Pro Arg Ile
        30                  35                  40

CGA GGC GCC GGG ACG AGA GAA TTG GAG CTG GCC ATC AGA GTC ACC CTT        192
Arg Gly Ala Gly Thr Arg Glu Leu Glu Leu Ala Ile Arg Val Thr Leu
45                  50                  55                  60

TAC GCA GTG ATC TTT CTG ATG AGC GTT GGA GGA AAT GTG CTC ATC ATT        240
Tyr Ala Val Ile Phe Leu Met Ser Val Gly Gly Asn Val Leu Ile Ile
                65                  70                  75

GTG GTC CTG GGA CTG AGC CGC CGC CTG AGA ACT GTG ACC AAT GCT TTC        288
Val Val Leu Gly Leu Ser Arg Arg Leu Arg Thr Val Thr Asn Ala Phe
            80                  85                  90

CTG CTC TCC CTG GCA GTC AGT GAC CTC CTG CTG GCT GTG GCT TGC ATG        336
Leu Leu Ser Leu Ala Val Ser Asp Leu Leu Leu Ala Val Ala Cys Met
        95                  100                 105

CCC TTC ACA CTC CTG CCC AAT CTT ATG GGC ACA TTC ATC TTT GGC ACC        384
Pro Phe Thr Leu Leu Pro Asn Leu Met Gly Thr Phe Ile Phe Gly Thr
    110                 115                 120

GTC ATC TGC AAG GCT GTT TCC TAC CTC ATG GGG GTG TCT GTG AGC GTG        432
Val Ile Cys Lys Ala Val Ser Tyr Leu Met Gly Val Ser Val Ser Val
125                 130                 135                 140

TCC ACG CTC AGC CTT GTG GCC ATC GCC CTG GAG CGG TAC AGC GCC ATC        480
Ser Thr Leu Ser Leu Val Ala Ile Ala Leu Glu Arg Tyr Ser Ala Ile
                145                 150                 155

TGC CGA CCA CTG CAG GCT CGA GTG TGG CAG ACC CGC TCC CAC GCA GCT        528
Cys Arg Pro Leu Gln Ala Arg Val Trp Gln Thr Arg Ser His Ala Ala
            160                 165                 170

CGC GTG ATT TTA GCC ACT TGG CTG CTG TCC GGA TTG CTC ATG GTC CCC        576
Arg Val Ile Leu Ala Thr Trp Leu Leu Ser Gly Leu Leu Met Val Pro
        175                 180                 185

TAC CCT GTG TAC ACT GCT GTG CAG CCG GTA GGG CCT CGT GTG CTG CAG        624
Tyr Pro Val Tyr Thr Ala Val Gln Pro Val Gly Pro Arg Val Leu Gln
    190                 195                 200

TGC GTG CAT CGC TGG CCC AAC GCA CGG GTC CGC CAG ACC TGG TCA GTA        672
Cys Val His Arg Trp Pro Asn Ala Arg Val Arg Gln Thr Trp Ser Val
205                 210                 215                 220

CTG CTG CTC CTG TTG TTC TTC GTC CCC GGA GTG GTT ATG GCA GTG        720
Leu Leu Leu Leu Leu Leu Phe Phe Val Pro Gly Val Val Met Ala Val
                225                 230                 235

GCC TAC GGG CTC ATC TCC CGC GAG CTC TAC TTA GGG CTT CGC TTT GAC        768
Ala Tyr Gly Leu Ile Ser Arg Glu Leu Tyr Leu Gly Leu Arg Phe Asp
            240                 245                 250

GGT GAC GCC GAC AGT GAG AGC CAG AGC AGG GTC CGA GGC CCG GGA GGT        816
Gly Asp Ala Asp Ser Glu Ser Gln Ser Arg Val Arg Gly Pro Gly Gly
        255                 260                 265

CTG TCC GGT TCC GCG CCA GGT CCT GCT CAC CAG AAT GGG CGT TGC CGG        864
Leu Ser Gly Ser Ala Pro Gly Pro Ala His Gln Asn Gly Arg Cys Arg
    270                 275                 280

CCT GAA TCT GGC CTG TCA GGC GAG GAC AGC GAC GGC TGC TAT GTG CAA        912
Pro Glu Ser Gly Leu Ser Gly Glu Asp Ser Asp Gly Cys Tyr Val Gln
285                 290                 295                 300

CTG CCA CGG TCT CGG CCG GCC CTG GAG CTG TCG GCC CTG GCG GCG TCC        960
```

| | | | | | | | | | | | | | | |
|---|---|---|---|---|---|---|---|---|---|---|---|---|---|---|
| Leu | Pro | Arg | Ser<br>305 | Arg | Pro | Ala | Leu | Glu | Leu<br>310 | Ser | Ala | Leu | Ala<br>315 | Ser |

| | | | | | | | | | | | | | | | |
|---|---|---|---|---|---|---|---|---|---|---|---|---|---|---|---|
| ACC | CCT | GCA | CCA | GGA | CCT | GGC | CCC | CGG | CCC | ACC | CAG | GCC | AAG | CTG | CTG |
| Thr | Pro | Ala<br>320 | Pro | Gly | Pro | Gly | Pro | Arg<br>325 | Pro | Thr | Gln | Ala | Lys<br>330 | Leu | Leu |

1008

| GCT | AAG | AAG | CGC | GTG | GTG | CGG | ATG | TTG | CTG | GTC | ATC | GTT | GTG | CTC | TTT |
|---|---|---|---|---|---|---|---|---|---|---|---|---|---|---|---|
| Ala | Lys | Lys<br>335 | Arg | Val | Val | Arg | Met<br>340 | Leu | Leu | Val | Ile | Val<br>345 | Val | Leu | Phe |

1056

| TTC | CTG | TGT | TGG | TTG | CCG | GTG | TAC | AGC | GCC | AAC | ACG | TGG | CGT | GCC | TTC |
|---|---|---|---|---|---|---|---|---|---|---|---|---|---|---|---|
| Phe | Leu<br>350 | Cys | Trp | Leu | Pro | Val | Tyr<br>355 | Ser | Ala | Asn | Thr | Trp<br>360 | Arg | Ala | Phe |

1104

| GAC | GGC | CCG | GGT | GCG | CAT | CGG | GCC | CTC | TCG | GGA | GCT | CCC | ATC | TCT | TTC |
|---|---|---|---|---|---|---|---|---|---|---|---|---|---|---|---|
| Asp<br>365 | Gly | Pro | Gly | Ala | His<br>370 | Arg | Ala | Leu | Ser | Gly<br>375 | Ala | Pro | Ile | Ser | Phe<br>380 |

1152

| ATC | CAT | TTG | CTG | AGC | TAC | GCC | TCC | GCC | TGT | GTC | AAC | CCA | CTG | GTC | TAC |
|---|---|---|---|---|---|---|---|---|---|---|---|---|---|---|---|
| Ile | His | Leu | Leu | Ser<br>385 | Tyr | Ala | Ser | Ala | Cys<br>390 | Val | Asn | Pro | Leu | Val<br>395 | Tyr |

1200

| TGC | TTC | ATG | CAC | CGT | CCG | TTT | CGC | CAG | GCC | TGC | CTG | GAC | ACT | TGC | GCC |
|---|---|---|---|---|---|---|---|---|---|---|---|---|---|---|---|
| Cys | Phe | Met | His<br>400 | Arg | Pro | Phe | Arg | Gln<br>405 | Ala | Cys | Leu | Asp | Thr<br>410 | Cys | Ala |

1248

| CGC | TGC | TGC | CCT | AGG | CCT | CCT | CGA | GCT | CGT | CCC | AGG | CCT | CTC | CCA | GAG |
|---|---|---|---|---|---|---|---|---|---|---|---|---|---|---|---|
| Arg | Cys | Cys<br>415 | Pro | Arg | Pro | Pro | Arg<br>420 | Ala | Arg | Pro | Arg | Pro<br>425 | Leu | Pro | Glu |

1296

| GAG | GAC | CCT | CCC | ACC | CCC | TCC | ATT | CGT | TCG | CTG | TCC | AGG | CTG | AGC | TAC |
|---|---|---|---|---|---|---|---|---|---|---|---|---|---|---|---|
| Glu | Asp<br>430 | Pro | Pro | Thr | Pro | Ser<br>435 | Ile | Arg | Ser | Leu | Ser<br>440 | Arg | Leu | Ser | Tyr |

1344

| ACC | ACC | ATC | AGC | ACG | CTG | GGG | CCC | GGC | TGATGGGGGT | GGTGGGGGCG |
|---|---|---|---|---|---|---|---|---|---|---|
| Thr | Thr | Ile | Ser | Thr | Leu<br>450 | Gly | Pro | Gly | | |

1391

| | |
|---|---|
| CTGAGGCAGC ACAGGCATCC TGTAAGCACA AATACATCCA GACACACAAG AAACACAAAC | 1451 |
| CACACTTGAC AGAGAGACTA ACACTCAACA GCATCGACTA ACCCAACACT CAGGAAACGG | 1511 |
| TGGCATAGTA CACACACACA CACACACACC AGAGCTTTAC ACAGAAAGGA GGCTCCCTGA | 1571 |
| GGGCCTTCCT AGAGACAGGG CACTGATCTT GACAGGCAAA CATAGCATCC TTAGCAGCAT | 1631 |
| CCTTATGCAC TGGGAACTCT GACAGCTGAC CGGTCCTCAT GCCCACATGC ATTAATCACA | 1691 |
| CTGATTCTCT AAGGGCAGCA GACCGTGGCA CAGGACTGAT TTGGGTTATT CCAGGCTGTC | 1751 |
| TTTAGTTTGA CATCACAAGA CACTTCTCCC CACCAGCACT GCCCCTACAA CAGGCCTGAT | 1811 |
| ACCTTCCTGA CCAACAGGCT CTTTAGGACT AAAAACTCTC TCTTCGTCCC TTTCCAGTTA | 1871 |
| AGGACTGCAG CCCTGCCCCC TCATCTTCAC CAGACCTCTT CAAAACACAA TAAATGACTT | 1931 |
| GCTCTCAAAA AAAAAAAAAA AAAAAAAAGC GGNNGCAGAA TTCGAGCTCG GTACCCGGGG | 1991 |
| ATCCTCTAGA GTCGACCTGC AGGC | 2015 |

( 2 ) INFORMATION FOR SEQ ID NO:26:

( i ) SEQUENCE CHARACTERISTICS:
        ( A ) LENGTH: 453 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| Met | Glu | Leu | Leu | Lys | Leu | Asn | Arg | Ser | Leu | Gln | Gly | Pro | Gly | Pro | Gly |
|---|---|---|---|---|---|---|---|---|---|---|---|---|---|---|---|
| 1 | | | | 5 | | | | | 10 | | | | | 15 | |

| Pro | Gly | Ala | Pro | Leu | Cys | Arg | Pro | Ala | Gly | Pro | Leu | Leu | Asn | Ser | Ser |
|---|---|---|---|---|---|---|---|---|---|---|---|---|---|---|---|
| | | | 20 | | | | | 25 | | | | | 30 | | |

| Gly | Ala | Gly | Asn | Val | Ser | Cys | Glu | Thr | Pro | Arg | Ile | Arg | Gly | Ala | Gly |
|---|---|---|---|---|---|---|---|---|---|---|---|---|---|---|---|
| | | 35 | | | | | 40 | | | | | 45 | | | |

```
Thr Arg Glu Leu Glu Leu Ala Ile Arg Val Thr Leu Tyr Ala Val Ile
    50                  55                  60
Phe Leu Met Ser Val Gly Gly Asn Val Leu Ile Ile Val Val Leu Gly
65              70                  75                          80
Leu Ser Arg Arg Leu Arg Thr Val Thr Asn Ala Phe Leu Leu Ser Leu
                85                  90                  95
Ala Val Ser Asp Leu Leu Leu Ala Val Ala Cys Met Pro Phe Thr Leu
            100             105             110
Leu Pro Asn Leu Met Gly Thr Phe Ile Phe Gly Thr Val Ile Cys Lys
        115             120             125
Ala Val Ser Tyr Leu Met Gly Val Ser Val Ser Val Ser Thr Leu Ser
        130             135             140
Leu Val Ala Ile Ala Leu Glu Arg Tyr Ser Ala Ile Cys Arg Pro Leu
145             150             155             160
Gln Ala Arg Val Trp Gln Thr Arg Ser His Ala Ala Arg Val Ile Leu
                165             170             175
Ala Thr Trp Leu Leu Ser Gly Leu Leu Met Val Pro Tyr Pro Val Tyr
            180             185             190
Thr Ala Val Gln Pro Val Gly Pro Arg Val Leu Gln Cys Val His Arg
        195             200             205
Trp Pro Asn Ala Arg Val Arg Gln Thr Trp Ser Val Leu Leu Leu Leu
210             215             220
Leu Leu Phe Phe Val Pro Gly Val Val Met Ala Val Ala Tyr Gly Leu
225             230             235             240
Ile Ser Arg Glu Leu Tyr Leu Gly Leu Arg Phe Asp Gly Asp Ala Asp
            245             250             255
Ser Glu Ser Gln Ser Arg Val Arg Gly Pro Gly Gly Leu Ser Gly Ser
        260             265             270
Ala Pro Gly Pro Ala His Gln Asn Gly Arg Cys Arg Pro Glu Ser Gly
        275             280             285
Leu Ser Gly Glu Asp Ser Asp Gly Cys Tyr Val Gln Leu Pro Arg Ser
        290             295             300
Arg Pro Ala Leu Glu Leu Ser Ala Leu Ala Ala Ser Thr Pro Ala Pro
305             310             315             320
Gly Pro Gly Pro Arg Pro Thr Gln Ala Lys Leu Leu Ala Lys Lys Arg
                325             330             335
Val Val Arg Met Leu Leu Val Ile Val Val Leu Phe Phe Leu Cys Trp
            340             345             350
Leu Pro Val Tyr Ser Ala Asn Thr Trp Arg Ala Phe Asp Gly Pro Gly
        355             360             365
Ala His Arg Ala Leu Ser Gly Ala Pro Ile Ser Phe Ile His Leu Leu
        370             375             380
Ser Tyr Ala Ser Ala Cys Val Asn Pro Leu Val Tyr Cys Phe Met His
385             390             395             400
Arg Pro Phe Arg Gln Ala Cys Leu Asp Thr Cys Ala Arg Cys Cys Pro
                405             410             415
Arg Pro Pro Arg Ala Arg Pro Arg Pro Leu Pro Glu Glu Asp Pro Pro
            420             425             430
Thr Pro Ser Ile Arg Ser Leu Ser Arg Leu Ser Tyr Thr Thr Ile Ser
        435             440             445
Thr Leu Gly Pro Gly
        450
```

( 2 ) INFORMATION FOR SEQ ID NO:27:

( i ) SEQUENCE CHARACTERISTICS:

(A) LENGTH: 453 amino acids
(B) TYPE: amino acid
(D) TOPOLOGY: linear (vii) IMMEDIATE SOURCE:
    (B) CLONE: canine gastrin receptor (xi) SEQUENCE DESCRIPTION: SEQ ID NO:27:

| Met | Glu | Leu | Leu | Lys | Leu | Asn | Arg | Ser | Ala | Gln | Gly | Ser | Gly | Ala | Gly |
|---|---|---|---|---|---|---|---|---|---|---|---|---|---|---|---|
| 1 | | | | 5 | | | | | 10 | | | | | 15 | |

| Pro | Gly | Ala | Ser | Leu | Cys | Arg | Ala | Gly | Gly | Ala | Leu | Leu | Asn | Ser | Ser |
|---|---|---|---|---|---|---|---|---|---|---|---|---|---|---|---|
| | | | 20 | | | | | 25 | | | | | 30 | | |

| Gly | Ala | Gly | Asn | Leu | Ser | Cys | Glu | Pro | Pro | Arg | Leu | Arg | Gly | Ala | Gly |
|---|---|---|---|---|---|---|---|---|---|---|---|---|---|---|---|
| | | 35 | | | | | 40 | | | | | 45 | | | |

| Thr | Arg | Glu | Leu | Glu | Leu | Ala | Ile | Arg | Val | Thr | Leu | Tyr | Ala | Val | Ile |
|---|---|---|---|---|---|---|---|---|---|---|---|---|---|---|---|
| | 50 | | | | | 55 | | | | | | 60 | | | |

| Phe | Leu | Met | Ser | Val | Gly | Gly | Asn | Val | Leu | Ile | Ile | Val | Val | Leu | Gly |
|---|---|---|---|---|---|---|---|---|---|---|---|---|---|---|---|
| 65 | | | | | 70 | | | | | 75 | | | | | 80 |

| Leu | Ser | Arg | Arg | Leu | Arg | Thr | Val | Thr | Asn | Ala | Phe | Leu | Leu | Ser | Leu |
|---|---|---|---|---|---|---|---|---|---|---|---|---|---|---|---|
| | | | | 85 | | | | | 90 | | | | | 95 | |

| Ala | Val | Ser | Asp | Leu | Leu | Leu | Ala | Val | Ala | Cys | Met | Pro | Phe | Thr | Leu |
|---|---|---|---|---|---|---|---|---|---|---|---|---|---|---|---|
| | | | 100 | | | | | 105 | | | | | 110 | | |

| Leu | Pro | Asn | Leu | Met | Gly | Thr | Phe | Ile | Phe | Gly | Thr | Val | Val | Cys | Lys |
|---|---|---|---|---|---|---|---|---|---|---|---|---|---|---|---|
| | | 115 | | | | | 120 | | | | | 125 | | | |

| Ala | Val | Ser | Tyr | Leu | Met | Gly | Val | Ser | Val | Ser | Val | Ser | Thr | Leu | Ser |
|---|---|---|---|---|---|---|---|---|---|---|---|---|---|---|---|
| | 130 | | | | | 135 | | | | | | 140 | | | |

| Leu | Val | Ala | Ile | Ala | Leu | Glu | Arg | Tyr | Ser | Ala | Ile | Cys | Arg | Pro | Leu |
|---|---|---|---|---|---|---|---|---|---|---|---|---|---|---|---|
| 145 | | | | | 150 | | | | | 155 | | | | | 160 |

| Gln | Ala | Arg | Val | Trp | Gln | Thr | Arg | Ser | His | Ala | Ala | Arg | Val | Ile | Ile |
|---|---|---|---|---|---|---|---|---|---|---|---|---|---|---|---|
| | | | | 165 | | | | | 170 | | | | | 175 | |

| Ala | Thr | Trp | Met | Leu | Ser | Gly | Leu | Leu | Met | Val | Pro | Tyr | Pro | Val | Tyr |
|---|---|---|---|---|---|---|---|---|---|---|---|---|---|---|---|
| | | | 180 | | | | | 185 | | | | | 190 | | |

| Thr | Ala | Val | Gln | Pro | Ala | Gly | Gly | Ala | Arg | Ala | Leu | Gln | Cys | Val | His |
|---|---|---|---|---|---|---|---|---|---|---|---|---|---|---|---|
| | | 195 | | | | | 200 | | | | | 205 | | | |

| Arg | Trp | Pro | Ser | Ala | Arg | Val | Arg | Gln | Thr | Trp | Ser | Val | Leu | Leu | Leu |
|---|---|---|---|---|---|---|---|---|---|---|---|---|---|---|---|
| | 210 | | | | | 215 | | | | | 220 | | | | |

| Leu | Leu | Leu | Phe | Phe | Val | Pro | Gly | Val | Val | Met | Ala | Val | Ala | Tyr | Gly |
|---|---|---|---|---|---|---|---|---|---|---|---|---|---|---|---|
| 225 | | | | | 230 | | | | | 235 | | | | | 240 |

| Leu | Ile | Ser | Arg | Glu | Leu | Tyr | Leu | Gly | Leu | Arg | Phe | Asp | Glu | Asp | Ser |
|---|---|---|---|---|---|---|---|---|---|---|---|---|---|---|---|
| | | | | 245 | | | | | 250 | | | | | 255 | |

| Asp | Ser | Glu | Ser | Arg | Val | Arg | Ser | Gln | Gly | Gly | Leu | Arg | Gly | Gly | Ala |
|---|---|---|---|---|---|---|---|---|---|---|---|---|---|---|---|
| | | | 260 | | | | | 265 | | | | | 270 | | |

| Gly | Pro | Gly | Pro | Ala | Pro | Pro | Asn | Gly | Ser | Cys | Arg | Pro | Glu | Gly | Gly |
|---|---|---|---|---|---|---|---|---|---|---|---|---|---|---|---|
| | | 275 | | | | | 280 | | | | | 285 | | | |

| Leu | Ala | Gly | Glu | Asp | Gly | Asp | Gly | Cys | Tyr | Val | Gln | Leu | Pro | Arg | Ser |
|---|---|---|---|---|---|---|---|---|---|---|---|---|---|---|---|
| | 290 | | | | | 295 | | | | | 300 | | | | |

| Arg | Gln | Thr | Leu | Glu | Leu | Ser | Ala | Leu | Thr | Ala | Pro | Thr | Pro | Gly | Pro |
|---|---|---|---|---|---|---|---|---|---|---|---|---|---|---|---|
| 305 | | | | | 310 | | | | | 315 | | | | | 320 |

| Gly | Gly | Gly | Pro | Arg | Pro | Tyr | Gln | Ala | Lys | Leu | Leu | Ala | Lys | Lys | Arg |
|---|---|---|---|---|---|---|---|---|---|---|---|---|---|---|---|
| | | | | 325 | | | | | 330 | | | | | 335 | |

| Val | Val | Arg | Met | Leu | Leu | Val | Ile | Val | Val | Leu | Phe | Phe | Leu | Cys | Trp |
|---|---|---|---|---|---|---|---|---|---|---|---|---|---|---|---|
| | | | 340 | | | | | 345 | | | | | 350 | | |

| Leu | Pro | Leu | Tyr | Ser | Ala | Asn | Thr | Trp | Arg | Ala | Phe | Asp | Ser | Ser | Gly |
|---|---|---|---|---|---|---|---|---|---|---|---|---|---|---|---|
| | | 355 | | | | | 360 | | | | | 365 | | | |

| Ala | His | Arg | Ala | Leu | Ser | Gly | Ala | Pro | Ile | Ser | Phe | Ile | His | Leu | Leu |
|---|---|---|---|---|---|---|---|---|---|---|---|---|---|---|---|
| | 370 | | | | | 375 | | | | | 380 | | | | |

| Ser | Tyr | Ala | Ser | Ala | Cys | Val | Asn | Pro | Leu | Val | Tyr | Cys | Phe | Met | His |
|---|---|---|---|---|---|---|---|---|---|---|---|---|---|---|---|

```
                385                    390                     395                    400
     Arg  Arg  Phe  Arg  Gln  Ala  Cys  Leu  Glu  Thr  Cys  Ala  Arg  Cys  Cys  Pro
                          405                      410                      415

Arg  Pro  Pro  Arg  Ala  Arg  Pro  Arg  Pro  Leu  Pro  Asp  Glu  Asp  Pro  Pro
                          420                      425                      430

Thr  Pro  Ser  Ile  Ala  Ser  Leu  Ser  Arg  Leu  Ser  Tyr  Thr  Thr  Ile  Ser
                          435                      440                      445

Thr  Leu  Gly  Pro  Gly
                          450
```

( 2 ) INFORMATION FOR SEQ ID NO:28:

( i ) SEQUENCE CHARACTERISTICS:
        ( A ) LENGTH: 1969 base pairs
        ( B ) TYPE: nucleic acid
        ( C ) STRANDEDNESS: double
        ( D ) TOPOLOGY: linear ( i i ) MOLECULE TYPE: cDNA ( v i i ) IMMEDIATE SOURCE:
        ( B ) CLONE: human CCKB receptor ( i x ) FEATURE:
        ( A ) NAME/KEY: CDS
        ( B ) LOCATION: 1..1344

( x i ) SEQUENCE DESCRIPTION: SEQ ID NO:28:

```
ATG  GAG  CTG  CTC  AAG  CTG  AAC  CGG  AAC  GTG  CAG  GGA  ACC  GGA  CCC  GGG           48
Met  Glu  Leu  Leu  Lys  Leu  Asn  Arg  Asn  Val  Gln  Gly  Thr  Gly  Pro  Gly
 1                 5                        10                       15

CCG  GGG  GCT  TCC  CTG  TGC  CGC  CCG  GGG  GCG  CCT  CTC  CTC  AAC  AGC  AGC           96
Pro  Gly  Ala  Ser  Leu  Cys  Arg  Pro  Gly  Ala  Pro  Leu  Leu  Asn  Ser  Ser
                    20                       25                       30

AGT  GTG  GGC  AAC  CTC  AGC  TGC  GAG  CCC  CCT  CGC  ATT  CGC  GGA  GCC  GGG          144
Ser  Val  Gly  Asn  Leu  Ser  Cys  Glu  Pro  Pro  Arg  Ile  Arg  Gly  Ala  Gly
          35                       40                       45

ACA  CGA  GAA  TTG  GAG  CTG  GCC  ATT  AGA  ATC  ACT  CTT  TAC  GCA  GTG  ATC          192
Thr  Arg  Glu  Leu  Glu  Leu  Ala  Ile  Arg  Ile  Thr  Leu  Tyr  Ala  Val  Ile
     50                       55                       60

TTC  CTG  ATG  AGC  GTT  GGA  GGA  AAT  ATG  CTC  ATC  ATC  GTG  GTC  CTG  GGA          240
Phe  Leu  Met  Ser  Val  Gly  Gly  Asn  Met  Leu  Ile  Ile  Val  Val  Leu  Gly
65                      70                       75                       80

CTG  AGC  CGC  CGC  CTG  AGG  ACT  GTC  ACC  AAT  GCC  TTC  CTC  CTC  TCA  CTG          288
Leu  Ser  Arg  Arg  Leu  Arg  Thr  Val  Thr  Asn  Ala  Phe  Leu  Leu  Ser  Leu
                    85                       90                       95

GCA  GTC  AGC  GAC  CTC  CTG  CTG  GCT  GTG  GCT  TGC  ATG  CCC  TTC  ACC  CTC          336
Ala  Val  Ser  Asp  Leu  Leu  Leu  Ala  Val  Ala  Cys  Met  Pro  Phe  Thr  Leu
          100                      105                      110

CTG  CCC  AAT  CTC  ATG  GGC  ACA  TTC  ATC  TTT  GGC  ACC  GTC  ATC  TGC  AAG          384
Leu  Pro  Asn  Leu  Met  Gly  Thr  Phe  Ile  Phe  Gly  Thr  Val  Ile  Cys  Lys
     115                      120                      125

GCG  GTT  TCC  TAC  CTC  ATG  GGG  GTG  TCT  GTG  AGT  GTG  TCC  ACG  CTA  AGC          432
Ala  Val  Ser  Tyr  Leu  Met  Gly  Val  Ser  Val  Ser  Val  Ser  Thr  Leu  Ser
130                     135                      140

CTC  GTG  GCC  ATC  GCA  CTG  GAG  CGG  TAC  AGC  GCC  ATC  TGC  CGA  CCA  CTG          480
Leu  Val  Ala  Ile  Ala  Leu  Glu  Arg  Tyr  Ser  Ala  Ile  Cys  Arg  Pro  Leu
145                     150                      155                      160

CAG  GCA  CGA  GTG  TGG  CAG  ACG  CGC  TCC  CAC  GCG  GCT  CGC  GTG  ATT  GTA          528
Gln  Ala  Arg  Val  Trp  Gln  Thr  Arg  Ser  His  Ala  Ala  Arg  Val  Ile  Val
                    165                      170                      175

GCC  ACG  TGG  CTG  CTG  TCC  GGA  CTA  CTC  ATG  GTG  CCC  TAC  CCC  GTG  TAC          576
Ala  Thr  Trp  Leu  Leu  Ser  Gly  Leu  Leu  Met  Val  Pro  Tyr  Pro  Val  Tyr
          180                      185                      190
```

| | | | | | | | | | | | | | | | | |
|---|---|---|---|---|---|---|---|---|---|---|---|---|---|---|---|---|
| ACT | GTC | GTG | CAA | CCA | GTG | GGG | CCT | CGT | GTG | CTG | CAG | TGC | GTG | CAT | CGC | 624 |
| Thr | Val | Val 195 | Gln | Pro | Val | Gly 200 | Pro | Arg | Val | Leu | Gln 205 | Cys | Val | His | Arg | |
| TGG | CCC | AGT | GCG | CGG | GTC | CGC | CAG | ACC | TGG | TCC | GTA | CTG | CTG | CTT | CTG | 672 |
| Trp | Pro | Ser 210 | Ala | Arg | Val | Arg 215 | Gln | Thr | Trp | Ser | Val 220 | Leu | Leu | Leu | Leu | |
| CTC | TTG | TTC | TTC | ATC | CCG | AGT | GTG | GTT | ATG | GCC | GTG | GCC | TAC | GGG | CTT | 720 |
| Leu 225 | Leu | Phe | Phe | Ile | Pro 230 | Ser | Val | Val | Met 235 | Ala | Val | Ala | Tyr | Gly | Leu 240 | |
| ATC | TCT | CGC | GAG | CTC | TAC | TTA | GGG | CTT | CGC | TTT | GAC | GGC | GAC | AGT | GAC | 768 |
| Ile | Ser | Arg | Glu | Leu 245 | Tyr | Leu | Gly | Leu | Arg 250 | Phe | Asp | Gly | Asp | Ser 255 | Asp | |
| AGC | GAC | AGC | CAA | AGC | AGG | GTC | CGA | AAC | CAA | GGC | GGG | CTG | CCA | GGG | GCT | 816 |
| Ser | Asp | Ser | Gln 260 | Ser | Arg | Val | Arg | Asn 265 | Gln | Gly | Gly | Leu | Pro 270 | Gly | Ala | |
| GTT | CAC | CAG | AAC | GGG | CGT | TGC | CGG | CCT | GAG | ACT | GGC | GCG | GTT | GGC | GAA | 864 |
| Val | His | Gln 275 | Asn | Gly | Arg | Cys | Arg 280 | Pro | Glu | Thr | Gly | Ala 285 | Val | Gly | Glu | |
| GAC | AGC | GAT | GGC | TGC | TAC | GTG | CAA | CTT | CCA | CGT | TCC | CGG | CCT | GCC | CTG | 912 |
| Asp | Ser | Asp | Gly 290 | Cys | Tyr | Val | Gln | Leu 295 | Pro | Arg | Ser | Arg | Pro 300 | Ala | Leu | |
| GAG | CTG | ACG | GCG | CTG | ACG | GCT | CCA | GGG | CCG | GGA | TCC | GGC | TCC | CGG | CCC | 960 |
| Glu 305 | Leu | Thr | Ala | Leu | Thr 310 | Ala | Pro | Gly | Pro | Gly 315 | Ser | Gly | Ser | Arg | Pro 320 | |
| ACC | CAG | GCC | AAG | CTG | CTG | GCT | AAG | AAG | CGC | GTG | GTG | CGA | ATG | TTG | CTG | 1008 |
| Thr | Gln | Ala | Lys | Leu 325 | Leu | Ala | Lys | Lys | Arg 330 | Val | Val | Arg | Met | Leu 335 | Leu | |
| GTG | ATC | GTT | GTG | CTT | TTT | TTT | CTG | TGT | TGG | TTG | CCA | GTT | TAT | AGT | GCC | 1056 |
| Val | Ile | Val | Val 340 | Leu | Phe | Phe | Leu | Cys 345 | Trp | Leu | Pro | Val | Tyr 350 | Ser | Ala | |
| AAC | ACG | TGG | CGC | GCC | TTT | GAT | GGC | CCG | GGT | GCA | CAC | CGA | GCA | CTC | TCG | 1104 |
| Asn | Thr | Trp 355 | Arg | Ala | Phe | Asp | Gly 360 | Pro | Gly | Ala | His | Arg 365 | Ala | Leu | Ser | |
| GGT | GCT | CCT | ATC | TCC | TTC | ATT | CAC | TTG | CTG | AGC | TAC | GCC | TCG | GCC | TGT | 1152 |
| Gly 370 | Ala | Pro | Ile | Ser | Phe 375 | Ile | His | Leu | Leu | Ser 380 | Tyr | Ala | Ser | Ala | Cys | |
| GTC | AAC | CCC | CTG | GTC | TAC | TGC | TTC | ATG | CAC | CGT | CGC | TTT | CGC | CAG | GCC | 1200 |
| Val 385 | Asn | Pro | Leu | Val | Tyr 390 | Cys | Phe | Met | His | Arg 395 | Arg | Phe | Arg | Gln | Ala 400 | |
| TGC | CTG | GAA | ACT | TGC | GCT | CGC | TGC | TGC | CCC | CGG | CCT | CCA | CGA | GCT | CGC | 1248 |
| Cys | Leu | Glu | Thr | Cys 405 | Ala | Arg | Cys | Cys | Pro 410 | Arg | Pro | Pro | Arg | Ala 415 | Arg | |
| CCC | AGG | GCT | CTT | CCC | GAT | GAG | GAC | CCT | CCC | ACT | CCC | TCC | ATT | GCT | TCG | 1296 |
| Pro | Arg | Ala | Leu 420 | Pro | Asp | Glu | Asp | Pro 425 | Pro | Thr | Pro | Ser | Ile 430 | Ala | Ser | |
| CTG | TCC | AGG | CTT | AGC | TAC | ACC | ACC | ATC | AGC | ACA | CTG | GGC | CCT | GGC | TGAGGAGT | 1351 |
| Leu | Ser | Arg 435 | Leu | Ser | Tyr | Thr | Thr 440 | Ile | Ser | Thr | Leu | Gly 445 | Pro | Gly | | |

```
AGGGGCCGTG  GGGGTTGAGG  CAGGGCAAAT  GACATGCACT  GACCCTTCCA  GACATAGAAA   1411
ACACAAACCA  CAACTGACAC  AGGAAACCAA  CACCCAAAGC  ATGGACTAAC  CCCAACGACA   1471
GGAAAAGGTA  GCTTACCTGA  CACAAGAGGA  ATAAGAATGG  AGCAGTACAT  GGGAAGGAG    1531
GCATGCCTCT  GATATGGGAC  TGAGCCTGGC  CCATAGAAAC  ATGACACTGA  CCTTGGAGAG   1591
ACACAGCGTC  CCTAGCAGTG  AACTATTTCT  ACACAGTGGG  AACTCTGACA  AGGGCTGACC   1651
TGCCTCTCAC  ACACATAGAT  TAATGGCACT  GATTGTTTTA  GAGACTATGG  AGCCTGGCAC   1711
AGGACTGACT  CTGGGATGCT  CCTAGTTTGA  CCTCACAGTG  ACCCTTCCCA  ATCAGCACTG   1771
AAAATACCAT  CAGGCCTAAT  CTCATACCTC  TGACCAACAG  GCTGTTCTGC  ACTGAAAAGG   1831
TTCTTCATCC  CTTTCCAGTT  AAGGACCGTG  GCCCTGCCCT  CTCCTTCCTT  CCCAAACTGT   1891
```

-continued

```
TCAAGAAATA ATAAATTGTT TGGCTTCCTC CTGAAAAAAA AAAAAAAAAA AAAAAAAAA     1951

AAAAAAAAAA GGAATTCC                                                   1969
```

( 2 ) INFORMATION FOR SEQ ID NO:29:

( i ) SEQUENCE CHARACTERISTICS:
        ( A ) LENGTH: 447 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met Glu Leu Leu Lys Leu Asn Arg Asn Val Gln Gly Thr Gly Pro Gly
 1               5                  10                  15

Pro Gly Ala Ser Leu Cys Arg Pro Gly Ala Pro Leu Leu Asn Ser Ser
                20                  25                  30

Ser Val Gly Asn Leu Ser Cys Glu Pro Pro Arg Ile Arg Gly Ala Gly
             35                  40                  45

Thr Arg Glu Leu Glu Leu Ala Ile Arg Ile Thr Leu Tyr Ala Val Ile
         50                  55                  60

Phe Leu Met Ser Val Gly Gly Asn Met Leu Ile Ile Val Val Leu Gly
 65                  70                  75                  80

Leu Ser Arg Arg Leu Arg Thr Val Thr Asn Ala Phe Leu Leu Ser Leu
                 85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
            115                 120                 125

Ala Val Ser Tyr Leu Met Gly Val Ser Val Ser Val Ser Thr Leu Ser
        130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170                 175

Ala Thr Trp Leu Leu Ser Gly Leu Leu Met Val Pro Tyr Pro Val Tyr
                180                 185                 190

Thr Val Val Gln Pro Val Gly Pro Arg Val Leu Gln Cys Val His Arg
            195                 200                 205

Trp Pro Ser Ala Arg Val Arg Gln Thr Trp Ser Val Leu Leu Leu Leu
210                 215                 220

Leu Leu Phe Phe Ile Pro Ser Val Val Met Ala Val Ala Tyr Gly Leu
225                 230                 235                 240

Ile Ser Arg Glu Leu Tyr Leu Gly Leu Arg Phe Asp Gly Asp Ser Asp
                245                 250                 255

Ser Asp Ser Gln Ser Arg Val Arg Asn Gln Gly Gly Leu Pro Gly Ala
            260                 265                 270

Val His Gln Asn Gly Arg Cys Arg Pro Glu Thr Gly Ala Val Gly Glu
        275                 280                 285

Asp Ser Asp Gly Cys Tyr Val Gln Leu Pro Arg Ser Arg Pro Ala Leu
290                 295                 300

Glu Leu Thr Ala Leu Thr Ala Pro Gly Pro Gly Ser Gly Ser Arg Pro
305                 310                 315                 320

Thr Gln Ala Lys Leu Leu Ala Lys Lys Arg Val Val Arg Met Leu Leu
                325                 330                 335

Val Ile Val Val Leu Phe Phe Leu Cys Trp Leu Pro Val Tyr Ser Ala
            340                 345                 350
```

| Asn | Thr | Trp | Arg | Ala | Phe | Asp | Gly | Pro | Gly | Ala | His | Arg | Ala | Leu | Ser |
|---|---|---|---|---|---|---|---|---|---|---|---|---|---|---|---|
| | | 355 | | | | | 360 | | | | | 365 | | | |
| Gly | Ala | Pro | Ile | Ser | Phe | Ile | His | Leu | Leu | Ser | Tyr | Ala | Ser | Ala | Cys |
| | 370 | | | | | 375 | | | | | 380 | | | | |
| Val | Asn | Pro | Leu | Val | Tyr | Cys | Phe | Met | His | Arg | Arg | Phe | Arg | Gln | Ala |
| 385 | | | | | 390 | | | | | 395 | | | | | 400 |
| Cys | Leu | Glu | Thr | Cys | Ala | Arg | Cys | Cys | Pro | Arg | Pro | Pro | Arg | Ala | Arg |
| | | | | 405 | | | | | 410 | | | | | 415 | |
| Pro | Arg | Ala | Leu | Pro | Asp | Glu | Asp | Pro | Pro | Thr | Pro | Ser | Ile | Ala | Ser |
| | | | 420 | | | | | 425 | | | | | 430 | | |
| Leu | Ser | Arg | Leu | Ser | Tyr | Thr | Thr | Ile | Ser | Thr | Leu | Gly | Pro | Gly | |
| | | 435 | | | | | 440 | | | | | 445 | | | |